(12) United States Patent
Keravala et al.

(10) Patent No.: US 11,510,950 B2
(45) Date of Patent: Nov. 29, 2022

(54) VARIANT AAV CAPSIDS FOR INTRAVITREAL DELIVERY

(71) Applicant: Adverum Biotechnologies, Inc., Redwood City, CA (US)

(72) Inventors: Annahita Keravala, Palo Alto, CA (US); Diana Cepeda, Mountain View, CA (US); Mehdi Gasmi, San Diego, CA (US)

(73) Assignee: ADVERUM BIOTECHNOLOGIES, INC., Redwood City, CA (US)

( * ) Notice: Subject to any disclaimer, the term of this patent is extended or adjusted under 35 U.S.C. 154(b) by 260 days.

(21) Appl. No.: 16/858,042

(22) Filed: Apr. 24, 2020

(65) Prior Publication Data
US 2020/0338146 A1 Oct. 29, 2020

Related U.S. Application Data

(60) Provisional application No. 62/923,924, filed on Oct. 21, 2019, provisional application No. 62/839,548, filed on Apr. 26, 2019.

(51) Int. Cl.
| | | |
|---|---|---|
| C12N 15/86 | (2006.01) | |
| A61K 48/00 | (2006.01) | |
| C07K 14/005 | (2006.01) | |
| C12N 7/00 | (2006.01) | |
| A61K 38/17 | (2006.01) | |
| A61K 35/76 | (2015.01) | |
| A61K 9/00 | (2006.01) | |

(52) U.S. Cl.
CPC ............ *A61K 35/76* (2013.01); *A61K 9/0048* (2013.01); *A61K 48/0008* (2013.01); *C07K 14/005* (2013.01); *C12N 7/00* (2013.01); *C12N 2750/14121* (2013.01); *C12N 2750/14122* (2013.01)

(58) Field of Classification Search
CPC .......... C12N 15/86; C12N 2750/14143; C12N 2750/14122; C12N 7/00; C07K 14/005
See application file for complete search history.

(56) References Cited

U.S. PATENT DOCUMENTS

| | | |
|---|---|---|
| 4,522,811 A | 6/1985 | Eppstein |
| 5,861,484 A | 1/1999 | Kendall et al. |
| 6,054,297 A | 4/2000 | Carter |
| 6,566,118 B1 | 5/2003 | Atkinson |
| 6,723,551 B2 | 4/2004 | Kotin |
| 7,060,269 B1 | 6/2006 | Baca |
| 7,635,474 B2 | 12/2009 | Daly et al. |
| 9,441,244 B2 | 9/2016 | Schaffer et al. |
| 10,035,850 B2 | 7/2018 | Gekkieva et al. |
| 2004/0224411 A1 | 11/2004 | Clark et al. |
| 2007/0261127 A1 | 11/2007 | Boyden et al. |
| 2010/0015095 A1 | 1/2010 | Pan et al. |
| 2011/0301073 A1 | 12/2011 | Gregory |
| 2013/0323302 A1 | 12/2013 | Constable et al. |
| 2018/0127471 A1 | 5/2018 | Keravala |

FOREIGN PATENT DOCUMENTS

| | | |
|---|---|---|
| WO | 2017112868 A1 | 6/2017 |
| WO | 2017192584 A1 | 11/2017 |
| WO | 2017197355 A2 | 11/2017 |
| WO | 2017197355 A3 | 12/2017 |
| WO | 2018075798 A1 | 4/2018 |

OTHER PUBLICATIONS

Akiyama, H. et al. (2006). "Intraocular Injection of an Aptamer That Binds PDGF-B: A Potential Treatment for Proliferative Retinopathies," Journal of Cellular Physiology 207:407-412.
Berge, S.M. et al. (Jan. 1977). "Pharmaceuticals Salts," J. Pharmaceutical Sciences 66(1):1-19.
Booij, J.C. et al. (Jan. 2011) "Simultaneous Mutation Detection in 90 Retinal Disease Genes in Multiple Patients Using a Custom-Designed 300-kb Retinal Resequencing Chip," Ophthalmology 118:160-167.
Boye, S.L. et al. (Apr. 2016, e-pub Feb. 10, 2016). "Impact of Heparan Sulfate Binding on Transduction of Retina by Recombinant Adeno-Associated Virus Vectors," Journal of virology 90(8):4215-4231.
Conway, J.E. et al. (Nov. 1997). "Recombinant Adeno-Associated Virus Type 2 Replication and Packaging is Entirely Supported by a Herpes Simplex Virus Type 1 Amplicon Expressing Rep and Cap," J. Virology 71 (11):8780-8789.
Den Hollander, A.I. et al. (Oct. 1999). "Mutations in a Human Homologue of Drosophila Crumbs Cause Retinitis Pigmentosa (RP12)," Nat. Genet. 23:217-221.
Diester, I. et al. (Mar. 2011, e-pub. Jan. 30, 2011). "An Optogenetic Toolbox Designed for Primates," Nat. Neurolsci. 14(3):387-399.
Donnelly, P. et al. (1994). "Missense Mutation in the Choroideremia Gene," Human Molecular Genetics 3(6):1017.
Genbank Accession No. CAM23328.1. (Jan. 13, 2009). "Crumbs Homolong 1 (Drosophila) [Homo Sapiens]," 2 pages.
Genbank Accession No. NP_000313.2 (Apr. 24, 2022). Peripherin-2 [Homo sapiens], 3 pages.
Genbank Accession No. NP_001289.1. (Jun. 19, 2022). "Cyclic Nucleotide-Gated Cation Channel Alpha-3 Isoform 1 [Homo Sapiens]," 4 pages.
Genbank Accession No. Q93PQ2.1. (May 25, 2022). "RecName: Full=X-Linked Retinitis Pigmentosa GTPase Regulator-Interacting Protein 1; Short=RPGR-lnteracting Protein," 6 pages.
Genbank Accession No. Q96KN7.2. (May 25, 2022). "RecName: Full=X-Linked Retinitis Pigmentosa GTPase Regulator-Interacting Protein 1: Short=RPGR-lnteracting Protein 1," 11 pages.

(Continued)

*Primary Examiner* — Barry A Chestnut
(74) *Attorney, Agent, or Firm* — Morrison & Foerster LLP

(57) ABSTRACT

Provided are variant adeno-associated virus (AAV) capsid proteins and recombinant AAV virions having one or more variant AAV capsid proteins. Also provided are compositions and methods for the use of the recombinant AAV virions, such as for the treatment or prophylaxis of a disease or disorder.

32 Claims, 32 Drawing Sheets

Specification includes a Sequence Listing.

(56) References Cited

OTHER PUBLICATIONS

Genbank Accession No. Q9GLM3.1. (May 25, 2022). "RecName: Full=X-Linked Retinitis Pigmentoda GTPase Regulator-Interacting Protein 1; Short=RPGR-Interacting Protein 1," 4 pages.
Genbank Accession No. AAC39660.1 (Jun. 10, 2016). "Retinal Pigment Epithelium-Specific Protein [Homo Sapiens]," 2 pages.
Good, N.E. et al. (Feb. 1966). "Hydrogen Ion Buffers for Biological Research," Biochemistry 5(2):467-477.
Grainger, S.M. et al. (2005). "Infectious Titer Assay for Recombinant Adeno-Associated Virus Vectors Using Direct Cell Lysis and Endpoint Taqman PCR," Mol. Ther 11(Supp 1):S337, Abstract 869, 1 page.
Groth, A.C. et al. (May 23, 2000). "A Phage Integrase Directs Efficient Site-Specific Integration in Human Cells," Proc Natl Acad Sci. 97(11):5995-6000.
International Report on Patentability, dated Nov. 4, 2021, for International Patent Application No. PCT/US2020/029895, filed Apr. 24, 2020, 7 pages.
International Search report and Written Opinion from the International Searching Authority dated Jul. 17, 2020, for International Patent Application No. PCT/US2020/029895, filed Apr. 24, 2020, 15 pages.
Kendall, R.L. et al. (Nov. 1993). "Inhibition of Vascular Endothelial Cell Growth Factor Activity by an Endogenously Encoded Soluble Receptor," Proc Natl Acad. Sci 90(22): 10705-10709.
Kim, T.K. et al. (2010). "Mammalian Cell Transfection: The Present and the Future," Anal. Bioanal Chem. 397:3173-3178.
Kohl, S. et al. (Mar. 2005, e-pub. Dec. 15, 2004). "CNGB3 Mutations Account for 50% of all Cases With Autosomal Recessive Achromatopsia," Eur. J. Hum Genet 13(3):302-308.
Krysan, P.J. et al. (Mar. 1989). "Isolation of Human Sequences That Replicate Autonomously in Human Cells," Mol. Cell Biol. 9(3): 1026-1033.
Lai, C-M. et al. (Oct. 2005, e-pub. Jul. 14, 2005). "Long-Term Evaluation of AAV-Mediated sFlt-1 Gene Therapy for Ocular Neovascularization in Mice and Monkeys," Mol. Ther. 12(4):659-668.
Lee, J-H. et al. (Dec. 27, 2005, e-pub. Dec. 15, 2005). "A Therapeutic Aptamer Inhibits Angiogenesis by Specifically Targeting the Heparin Binding Domain of VEGF165," Proc Natl. Acad. Sci. USA 102(52):18902-18907.
Li, H. et al. (Jun. 2011). "In Vivo Genome Editing Restores Haemostasis in a Mouse Model of Haemophilia," Nature 175(7355):217-221.
Liu, X. L. et al. (Feb. 5, 1999). "Production Of Recombinant Adeno-Associated Virus Vectors Using A Packaging Cell Line And A Hybrid Recombinant Adenovirus," Gene Therapy 6(2):293-299.

Mancuso, K. et al. (Oct. 8, 2009). "Gene therapy for Red-Green Colour Blindness in Adult Primates," Nature 461 (7265):784-787.
Martin, J. et al. (Aug. 2013, e-pub. Aug. 9, 2013). "Generation and Characterization of Adeno-Associated Virus Producer Cell Lines for Research and Preclinical Vector Production," Human Gene Therapy Methods 24(4):253-269.
Morimura, H. et al. (Mar. 1998). "Mutations in the RPE65 Gene in Patients With Autosomal Recessive Tetinitis Pigmentosa or Leber Congenital Amaurosis," Proc. Natl. Acad. Sci. USA 95:3088-3093.
Mount, D. (Dec. 2004). "Bioinformatics: Sequence and Genome Analysis, 2nd ed.," Briefing In Bioinformatics 5 (4):391-396.
Ng, E.W.M. et al. (Feb. 2006). "Pegaptanib, A Targeted Anti-VEGF Aptamer for Ocular Vascular Disease," Nat. Rev. Drug Discovery 5(2):123-132.
Ni, Z. et al. (2009, e-pub. Jul. 20, 2009). "Emerging Pharmacologic Therapies for Wet Age-Related Macular Degeneration," Ophthalmologica 223:401-410.
Nicoud, M. et al. (2007) "Development of Photoreceptor-Specific Promoters and Their Utility to Investigate EIAV Lentiviral Vector Mediated Gene Transfer to Photoreceptors," The Journal of Gene Medicine 9(12): 1015-1023.
O'Gorman, S. et al. (Mar. 15, 1991). "Recombinase-Mediated Gene Activation and Site-Specific Integration in Mammalian Cells," Science 251:1351-1355.
Pechan, P. et al. (Jan. 2009, e-pub. Jul. 17, 2008). "Novel Anti-VEGF Chimeric Molecules Delivered by AAV Vectors for Inhibition of Retinal Neovascularization," Gene Ther. 16(1): 10-16.
Sauer, B. et al. (Jul. 1988). "Site-Specific DNA Recombination in Mammalian Cells by the Cre Recombinase of Bacteriophage P1," Proc. Natl. Acad. Sci. USA 85:5166-5170.
Travis, G.H. et al. (Jul. 1991). "The Human Retinal Degeneration Slow (RDS) Gene: Chromosome Assignment and Structure of the mRNA," Genomics 10(3):733-739.
Van Bokhoven, H. et al. (Jul. 1994). "Cloning and Characterization of the Human Choroideremia Gene," Hum. Mol. Genet. 3(7):1041-1046.
Wiesmann, C. et al. (Nov. 28, 1997). "Crystal Structure at 1.7 A Resolution of VEGF in Complex with Domain 2 of the Flt-1 Receptor," Cell 91:695-704.
Woodard, K.T. et al. (Nov. 2016). "Heparan Sulfate Binding Promotes Accumulation of Intravitreally Delivered Adena-associated Viral Vectors at the Retina for Enhanced Transduction but Weakly Influences Tropism," Journal of Virology 90(21):9878-9888.
Yokoyama, T. et al. (Aug. 1992). "Photoreceptor-Specific Activity of the Human Interphotoreceptor Retinoid-Binding Protein (IRBP) Promoter in Transgenic Mice," Exp. Eye Res. 55(2):225-233.
Young, J.E. et al. (Sep. 2003). "A Short, Highly Active Photoreceptor-Specific Enhancer/Promoter Region Upstream of the Human Rhodopsin Kinase Gene," Ophthalmol. Vis. Sci. 44(9):4076-4085.
Zolotukhin, S. et al. (1999). "Recombinant Adeno-Associated Virus Purification using Novel Methods Improves Infectious Titer and Yield," Gene Therapy 6(6):973-985.

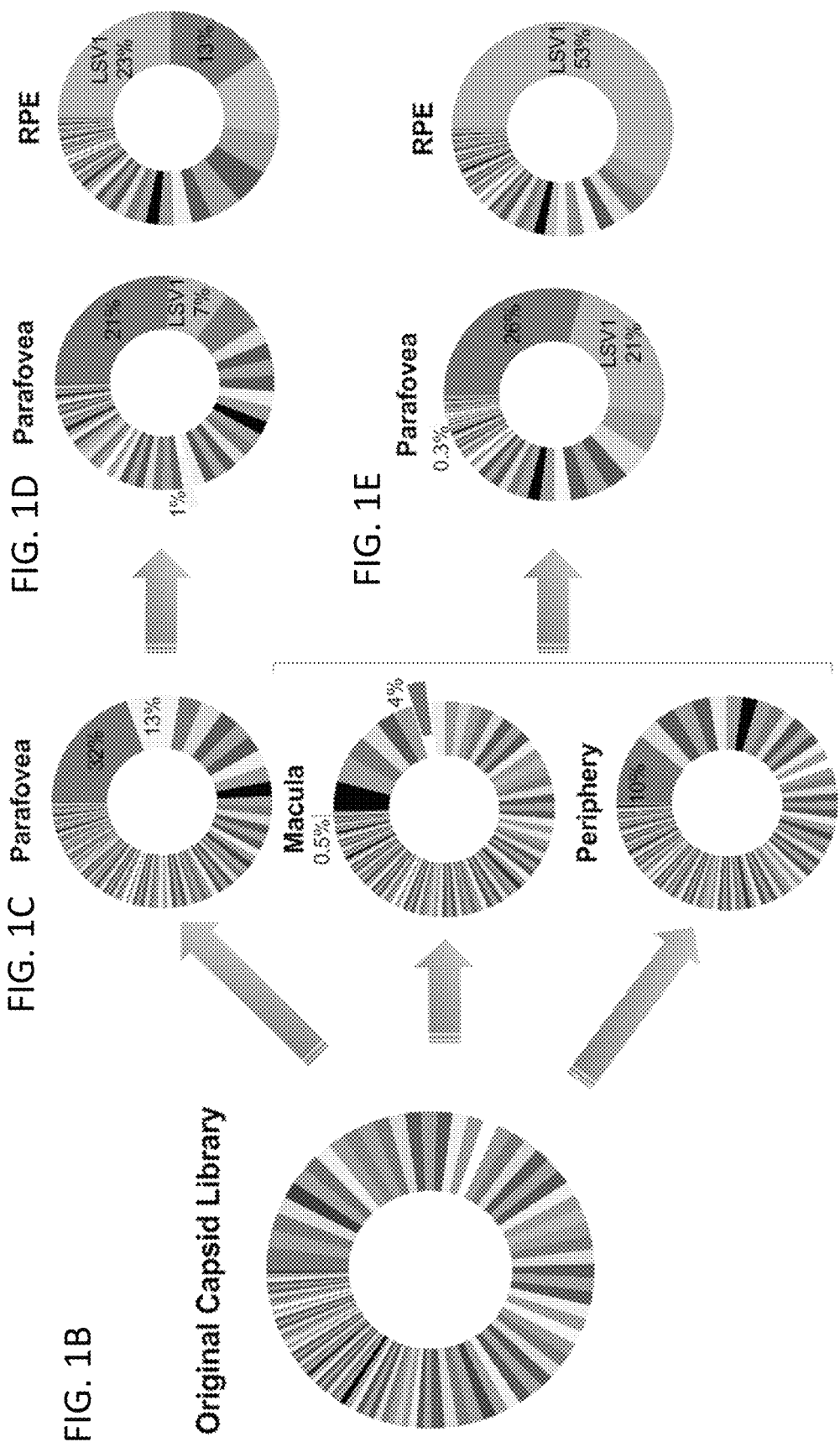

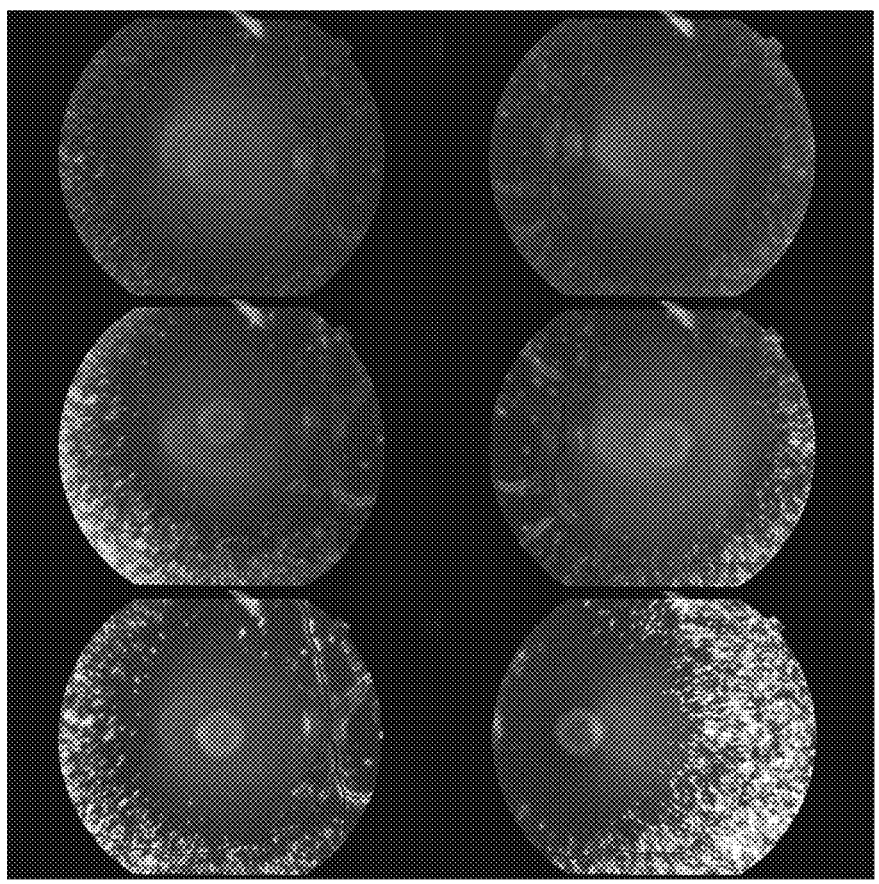
FIG. 4A Day 14
FIG. 4B Day 21
FIG. 4C Day 28

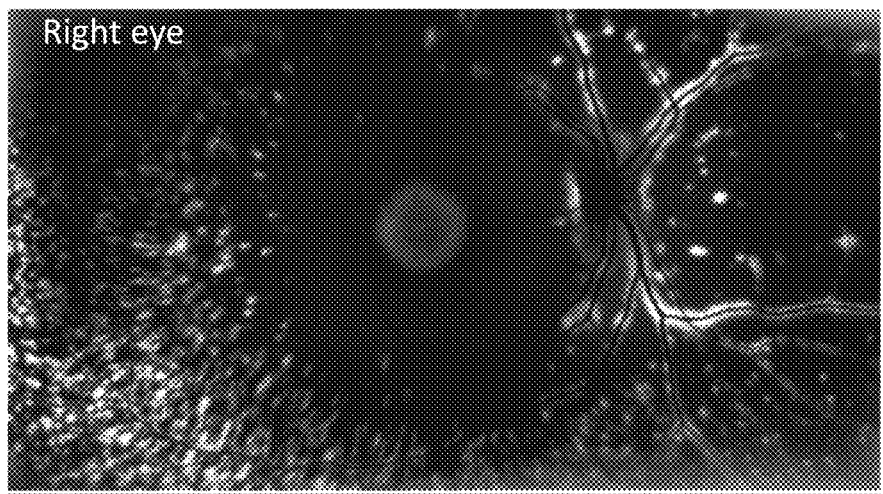
FIG. 4D Right eye Day 28
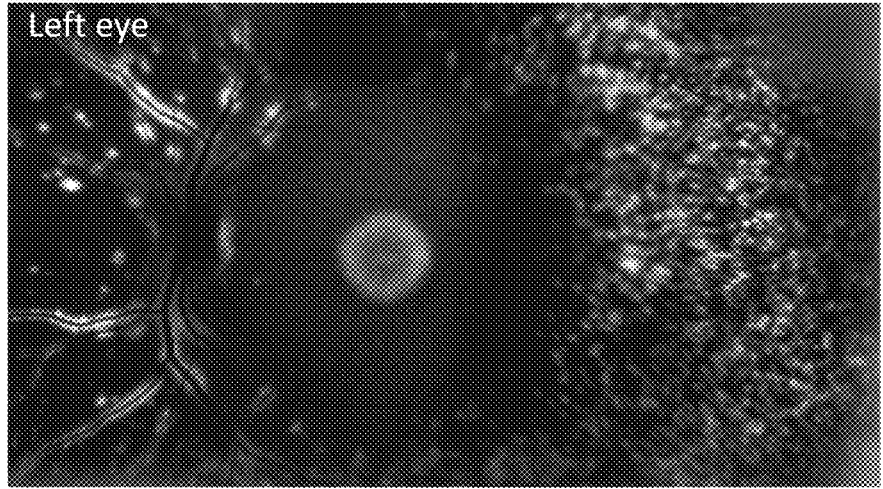
FIG. 4E Left eye Day 28

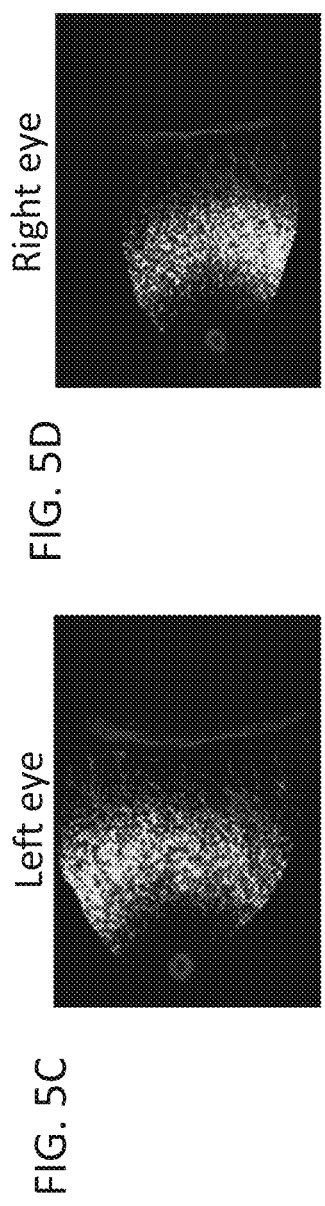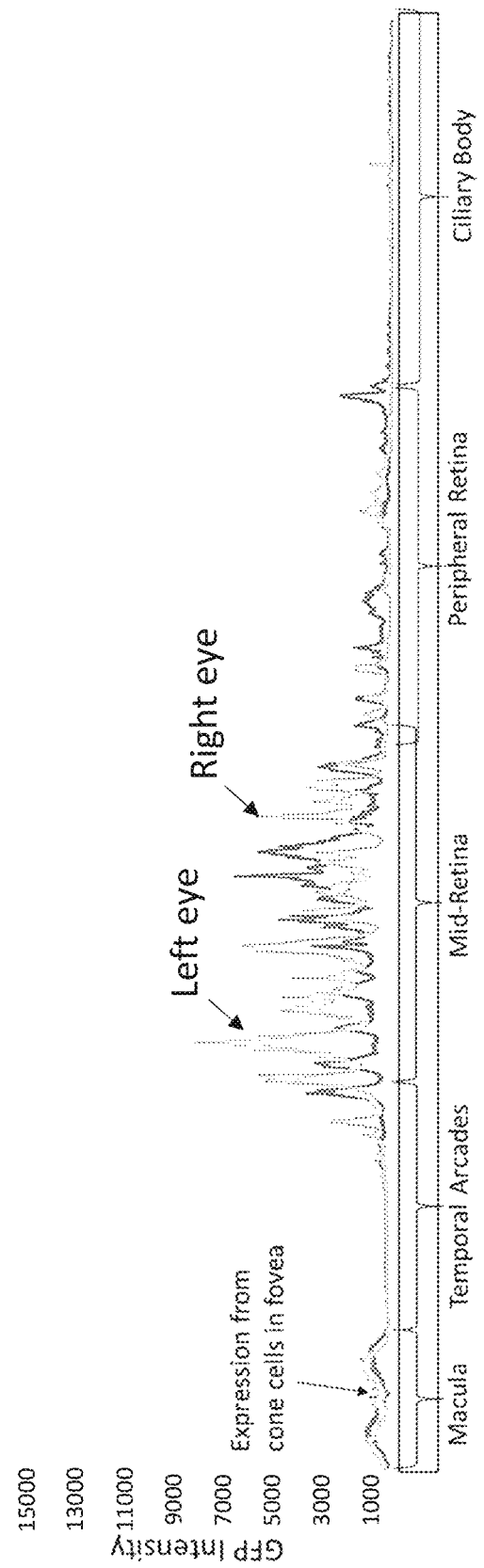
FIG. 5C  FIG. 5D
FIG. 5E

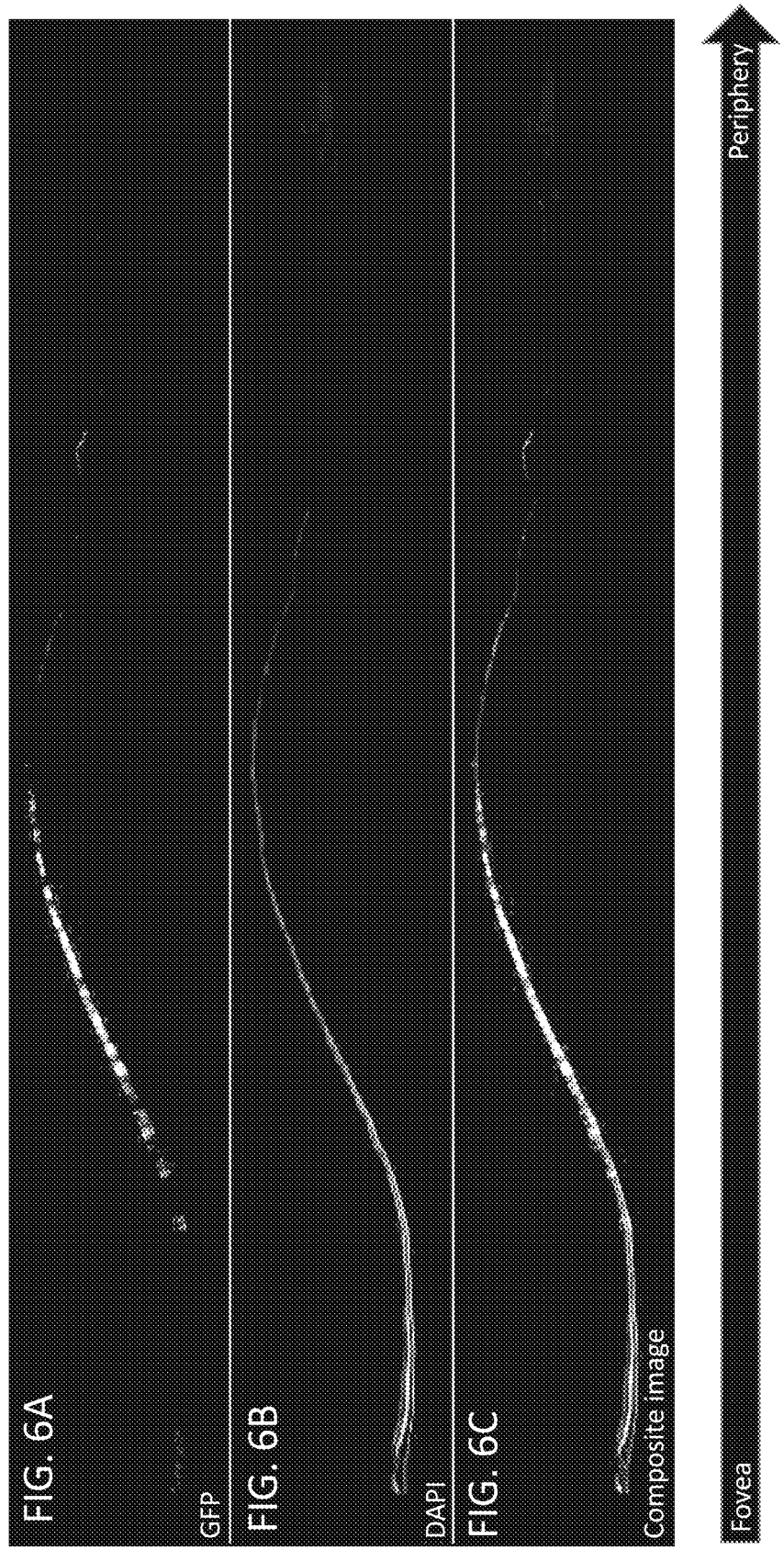

Composite image

DAPI

GFP

Rhodopsin

Composite image

DAPI

GFP

Glutamine Synthetase

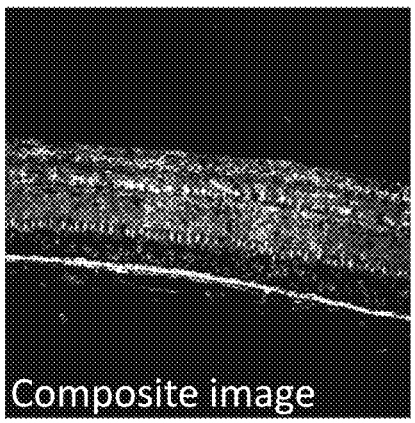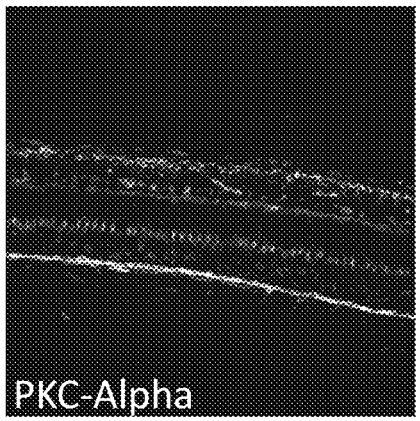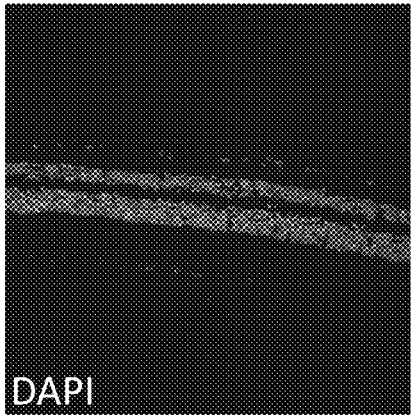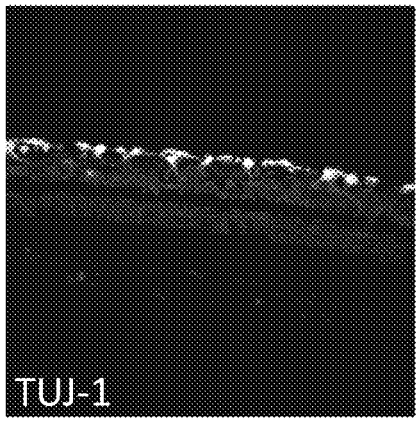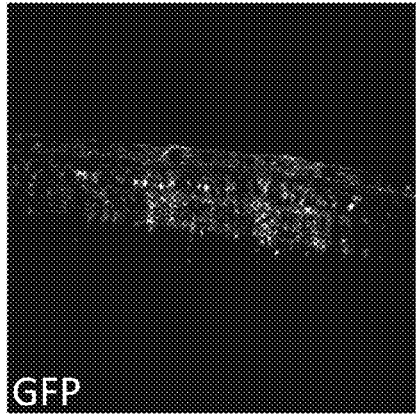

Composite image

DAPI

GFP

PKC-Alpha

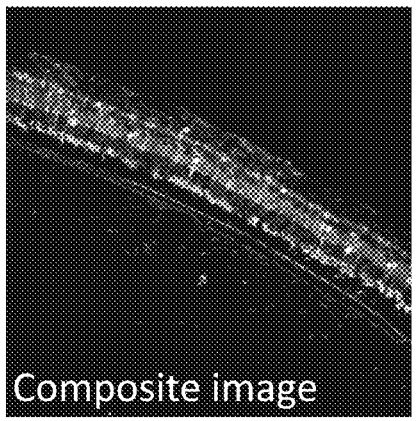
FIG. 20A Composite image
FIG. 20D Cone Arrestin
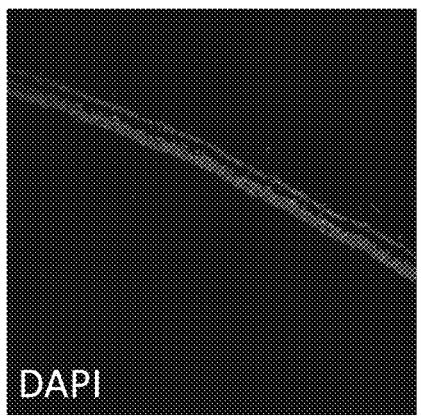
FIG. 20B DAPI
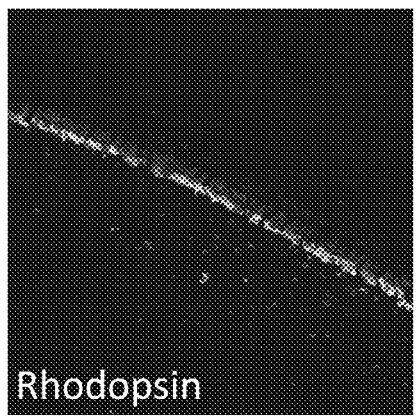
FIG. 20E Rhodopsin
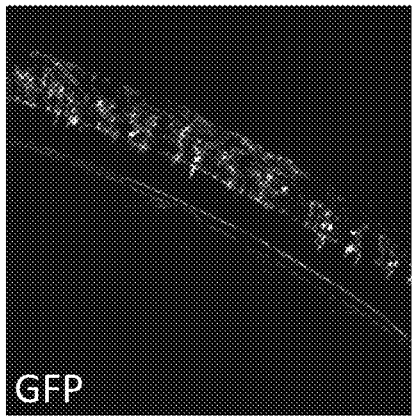
FIG. 20C GFP Composite image

RPE 65

DAPI

GFP – 647 nm

Native GFP- No antibody labeling

Composite image

RPE 65

DAPI

GFP – 647 nm

Native GFP- No antibody labeling

Composite image

RPE 65

DAPI

GFP – 647 nm

Native GFP- No antibody labeling

VARIANT AAV CAPSIDS FOR INTRAVITREAL DELIVERY

CROSS-REFERENCE TO RELATED APPLICATION

This application claims the benefit of U.S. Provisional Application 62/839,548, filed Apr. 26, 2019 and U.S. Provisional Application 62/923,924, filed Oct. 21, 2019, the contents of each of which are hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 627002001100SEQLIST.TXT, date recorded: Apr. 21, 2020, size: 49 KB).

BACKGROUND

A promising approach to treating and preventing genetic and other diseases and disorders is delivery of therapeutic gene products with a gene therapy vector such as a virion. Illustrative examples of virions suitable for gene therapy include but are not limited to retroviral virions, lentiviral virions, adenovirus virions, herpes virus virions, alphavirus virions, and adeno-associated virus (AAV) virions. AAV is a 4.7 kb, single-stranded DNA virus. Recombinant virions based on AAV (rAAV virions) are associated with excellent clinical safety, since wild-type AAV is nonpathogenic and has no etiologic association with any known diseases. In addition, AAV offers the capability for highly efficient gene delivery and sustained transgene expression in numerous tissues, including eye, muscle, lung and brain.

Certain challenges that remain with regard to the design of virions for use in gene therapy include optimizing viral cell tropism and, particularly with respect to gene therapy of the eye, optimizing delivery to the retina. Thus, there is a need for optimized virions for expressing genes in selected mammalian cells. The present invention addresses this need by providing modified AAV capsid proteins advantageous for the delivery of recombinant AAV virions to desired cells and tissues.

BRIEF SUMMARY

Provided herein are recombinant adeno-associated virus (AAV) virions comprising: (a) a variant AAV capsid protein comprising a modified sequence comprising one or more amino acid substitutions within amino acid residues 570-579 relative to a parental AAV capsid protein, wherein the modified sequence comprises HKFKSGD (SEQ ID NO: 1), and wherein the amino acid residue numbering corresponds to an AAV5 VP1 capsid protein; and (b) a polynucleotide sequence encoding a therapeutic gene product.

In some embodiments, the parental AAV capsid protein is an AAV5 capsid protein or an AAV5 and AAV2 hybrid capsid protein. In some embodiments, the parental AAV capsid protein is an AAV2.5T capsid protein. In some embodiments, the parental AAV capsid protein is an AAV2.5T VP1 capsid protein.

In some embodiments, the modified sequence comprises LAHKFKSGDA (SEQ ID NO: 3). In some embodiments, the variant AAV capsid protein comprises a capsid sequence having at least 85% homology to the amino acid sequence set forth in SEQ ID NO: 4 or SEQ ID NO:5. In some embodiments, the variant AAV capsid protein comprises a capsid sequence set forth in SEQ ID NO: 6 or SEQ ID NO: 7.

In some embodiments, the rAAV virion is a variant AAV5 or a variant AAV2 and AAV5 hybrid virion. In some embodiments, the rAAV virion is a variant AAV2.5T virion.

In some embodiments, the recombinant AAV virion is capable of transducing cells of the retina when intravitreally injected into a mammal. In some embodiments, the recombinant AAV virion is capable of transducing one or more of: a photoreceptor, a retinal ganglion cell, a Müller cell, a bipolar cell, an amacrine cell, a horizontal cell, and a retinal pigment epithelium cell when intravitreally injected into a mammal. In some embodiments, the recombinant AAV virion is capable of transducing retinal pigment epithelium cells when intravitreally injected into a mammal.

In some embodiments, the therapeutic gene product is a siRNA, a miRNA, or a protein. In some embodiments, the therapeutic gene product is an anti-vascular endothelial growth factor (anti-VEGF) gene product. In some embodiments, the therapeutic gene product is an opsin.

In some embodiments, the polynucleotide encoding the therapeutic gene product is flanked by one or more AAV ITRs. In some embodiments, the one or more AAV ITRs are AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV ITRs or variants thereof. In some embodiments, the one or more AAV ITRs are AAV2 ITRs or AAV5 ITRs.

In some embodiments, the recombinant AAV virion has an altered cellular tropism as compared to AAV2.5T.

In some embodiments, the recombinant AAV virion disclosed herein is for use in a method of treating a disease or disorder of the retina of a subject in need thereof, wherein the method comprises administering a pharmaceutical composition comprising the recombinant AAV virion to the subject by intravitreal injection. In some embodiments, the recombinant AAV virion disclosed herein is for use in the preparation of a medicament for the treatment of a disease or disorder of the retina of a subject. In some embodiments, the disease or disorder is age-related macular degeneration (AMD), wet-AMD, dry-AMD, retinal neovascularization, choroidal neovascularization, diabetic retinopathy, proliferative diabetic retinopathy, retinal vein occlusion, central retinal vein occlusion, branched retinal vein occlusion, diabetic macular edema, diabetic retinal ischemia, ischemic retinopathy, or diabetic retinal edema.

Also provided herein are pharmaceutical compositions comprising a recombinant AAV virion disclosed herein.

Also provided herein are methods for producing a rAAV virion comprising: (a) culturing a host cell under a condition that rAAV virions are produced, wherein the host cell comprises: (i) a polynucleotide encoding a variant AAV capsid protein comprising a modified sequence comprising one or more amino acid substitutions within amino acid residues 570-579 relative to a parental AAV capsid protein, wherein the modified sequence comprises HKFKSGD (SEQ ID NO: 1); (ii) a polynucleotide encoding a rep protein; (iii) a polynucleotide cassette comprising a sequence that encodes a therapeutic gene product flanked by at least one AAV ITR; and (iv) AAV helper functions; and (b) recovering the rAAV virion produced by the host cell.

Also provided herein are methods of providing a therapeutic gene product to a retina of a subject, comprising administering to the subject by intravitreal injection a recombinant AAV virion disclosed herein or a pharmaceutical composition disclosed herein.

In some embodiments, the subject has been diagnosed with or is suspected of having one or more conditions selected from the group consisting of: acute macular neuroretinopathy, Behcet's disease, choroidal neovascularization, diabetic uveitis, histoplasmosis, macular degeneration, edema, multifocal choroiditis, ocular trauma which affects a posterior ocular site or location, ocular tumor, central retinal vein occlusion, diabetic retinopathy, proliferative vitreoretinopathy (PVR), retinal arterial occlusive disease, retinal detachment, uveitic retinal disease, sympathetic ophthalmia, Vogt Koyanagi-Harada (VKH) syndrome, uveal diffusion, a posterior ocular condition caused by or influenced by an ocular laser treatment, posterior ocular conditions caused by or influenced by a photodynamic therapy, photocoagulation, radiation retinopathy, an epiretinal membrane disorder, branch retinal vein occlusion, anterior ischemic optic neuropathy, diabetic retinal ischemia, ischemic retinopathy, non-retinopathy diabetic retinal dysfunction, retinoschisis, retinitis pigmentosa, glaucoma, Usher syndrome, cone-rod dystrophy, Stargardt disease, inherited macular degeneration, chorioretinal degeneration, Leber congenital amaurosis, congenital stationary night blindness, choroideremia, Bardet-Biedl syndrome, macular telangiectasia, Leber's hereditary optic neuropathy, retinopathy of prematurity, and a disorder of color vision.

Also provided herein are methods of treating a disease or disorder of the retina of a subject in need thereof, comprising administering to the subject by intravitreal injection a recombinant AAV virion disclosed herein or a pharmaceutical composition disclosed herein.

In some embodiments, the disease or disorder is acute macular neuroretinopathy, Behcet's disease, choroidal neovascularization, diabetic uveitis, histoplasmosis, macular degeneration, edema, multifocal choroiditis, ocular trauma which affects a posterior ocular site or location, ocular tumor, central retinal vein occlusion, diabetic retinopathy, proliferative vitreoretinopathy (PVR), retinal arterial occlusive disease, retinal detachment, uveitic retinal disease, sympathetic ophthalmia, Vogt Koyanagi-Harada (VKH) syndrome, uveal diffusion, a posterior ocular condition caused by or influenced by an ocular laser treatment, posterior ocular conditions caused by or influenced by a photodynamic therapy, photocoagulation, radiation retinopathy, epiretinal membrane disorders, branch retinal vein occlusion, anterior ischemic optic neuropathy, diabetic retinal ischemia, ischemic retinopathy, non-retinopathy diabetic retinal dysfunction, retinoschisis, retinitis pigmentosa, glaucoma, Usher syndrome, cone-rod dystrophy, Stargardt disease, inherited macular degeneration, chorioretinal degeneration, Leber congenital amaurosis, congenital stationary night blindness, choroideremia, Bardet-Biedl syndrome, macular telangiectasia, Leber's hereditary optic neuropathy, retinopathy of prematurity, or a disorder of color vision.

Also provided herein are variant AAV capsid proteins comprising a modified sequence comprising one or more amino acid substitutions within amino acid residues 570-579 relative to a parental AAV capsid protein, wherein the modified sequence comprises HKFKSGD (SEQ ID NO: 1), and wherein the amino acid residue numbering corresponds to an AAV5 VP1 capsid protein.

In some embodiments, the parental AAV capsid protein is an AAV5 capsid protein or an AAV5 and AAV2 hybrid capsid protein. In some embodiments, the parental AAV capsid protein is an AAV2.5T capsid protein. In some embodiments, the parental AAV capsid protein is an AAV2.5T VP1 capsid protein.

In some embodiments, the modified AAV capsid protein comprises LAHKFKSGDA (SEQ ID NO: 3) at amino acid residues 570-579 relative to the parental AAV capsid protein. In some embodiments, the variant AAV capsid protein comprises a capsid sequence having at least 85% homology to the amino acid sequence set forth in SEQ ID NO: 4 or SEQ ID NO:5. In some embodiments, the variant AAV capsid protein comprises a capsid sequence set forth in SEQ ID NO: 6 or SEQ ID NO: 7.

Also provided herein are nucleic acids comprising nucleic acid sequences encoding a variant AAV capsid protein disclosed herein.

Also provided herein are expression vectors comprising a nucleic acid disclosed herein, wherein the nucleic acid sequence encoding the variant AAV capsid protein is operably linked to a promoter sequence. In some embodiments, the expression vector further comprises a nucleic acid that encodes a rep protein.

Also provided herein are cells comprising an expression vector disclosed herein. In some embodiments, the cell further comprises a nucleic acid that encodes a therapeutic gene product. In some embodiments, the therapeutic gene product is a siRNA, a miRNA, or a protein. In some embodiments, the therapeutic gene product is an anti-vascular endothelial growth factor (anti-VEGF) gene product. In some embodiments, the therapeutic agent is an opsin.

In some embodiments, the polynucleotide encoding the therapeutic gene product is flanked by one or more AAV ITRs. In some embodiments, the one or more AAV ITRs are AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV ITRs or variants thereof. In some embodiments, the one or more AAV ITRs are AAV2 ITRs or AAV5 ITRs.

All references cited herein, including patent applications and publications, are incorporated by reference in their entirety.

BRIEF DESCRIPTION OF THE DRAWINGS

FIGS. 1B-1E show the relative abundance of capsid variants at different stages of the selection process. FIG. 1B shows the percentage of the top 100 variants in the original library; FIG. 1C shows the percentage of the top 100 variants identified in the parafovea, macula, or peripheral retinal regions from the second screening round. FIG. 1D shows the percentage of the top 50 evolved variants that successfully transduced parafovea and RPE cells from round 2 libraries originating from the parafovea. FIG. 1E shows the percentage of the top 50 evolved variants that successfully transduced macula+periphery cells from round 2 libraries originating from the parafovea.

FIGS. 4A-4C provide OTC autofluorescence images of the retina of an African green monkey on day 14 (FIG. 4A), day 21 (FIG. 4B), and day 28 (FIG. 4C) after intravitreal administration of AAV2.5T.LSV1 virions encoding GFP, showing GFP expression within the fovea and the blood arcades.

FIGS. 4D-4E provide Heidelberg Spectralis images of the left (FIG. 4D) and right (FIG. 4E) retina of an African green monkey on day 28 after intravitreal administration of AAV2.5T.LSV1 virions encoding GFP, showing GFP expression within the fovea and the blood arcades.

FIGS. 5C-5D provide fluorescence images of flat-mounted retina of an African green monkey after intravitreal administration of AAV2.5T.LSV1 virions encoding GFP for the left eye (FIG. 5C) an for the right eye (FIG. 5D).

FIG. 5E provides GFP intensity profiles plotted across the distance from the macula to the ciliary body for the eyes shown in FIGS. 5C-5D. The retinal region locations were calculated from the mean distances in relation to the foveal center.

FIGS. 6A-6C provide fluorescence images of the fovea to ciliary body of the eye of an African green monkey after intravitreal administration of AAV2.5T.LSV1 virions encoding GFP. FIG. 6A shows GFP expression. FIG. 6B shows DAPI staining of nuclei. FIG. 6C is a composite image of FIG. 6A and FIG. 6B.

FIG. 9A shows a composite image of FIGS. 9B-9D. FIG. 9B shows DAPI staining of nuclei. FIG. 9C shows GFP expression. FIG. 9D shows rhodopsin antibody labeling of rod photoreceptor cells.

FIG. 10A shows a composite image of FIGS. 10B-10D. FIG. 10B shows DAPI staining of nuclei. FIG. 10C shows GFP expression. FIG. 10D shows glutamine synthetase antibody labeling of Müller cells.

FIG. 12A is a composite image of FIG. 12B and FIG. 12C. FIG. 12B shows DAPI staining of nuclei. FIG. 12C shows GFP expression.

FIG. 13A shows a composite image of FIGS. 13B-13D. FIG. 13B shows DAPI staining of nuclei. FIG. 13C shows GFP expression. FIG. 13D shows glutamine synthetase antibody labeling of Müller cells.

FIG. 14A shows a composite image of FIGS. 14B-14D. FIG. 14B shows DAPI staining of nuclei. FIG. 14C shows GFP expression. FIG. 14D shows glutamine synthetase antibody labeling of Müller cells.

FIG. 15A shows a composite image of FIGS. 15B-15D. FIG. 15B shows DAPI staining of nuclei. FIG. 15C shows GFP expression. FIG. 15D shows glutamine synthetase antibody labeling of Müller cells.

FIGS. 16A-16E provide fluorescence images of the retina of the eye of an African green monkey after intravitreal administration of AAV2.5T.LSV1 virions encoding GFP. FIG. 16A shows a composite image of FIGS. 16B-16E. FIG. 16B shows DAPI staining of nuclei. FIG. 16C shows GFP expression. FIG. 16D shows PCK-Alpha antibody labeling of bipolar cells. FIG. 16E shows TUJ-1 antibody labeling of retinal ganglion axon terminal pathways.

FIG. 17A shows a composite image of FIGS. 17B-17D. FIG. 17B shows DAPI staining of nuclei. FIG. 17C shows GFP expression. FIG. 17D shows PCK-Alpha antibody labeling of bipolar cells.

FIG. 18A shows a composite image of FIGS. 18B-18E. FIG. 18B shows DAPI staining of nuclei. FIG. 18C shows GFP expression. FIG. 18D shows cone arrestin antibody labeling of cone photoreceptor cells. FIG. 18E shows rhodopsin antibody labeling of rod photoreceptor cells.

FIG. 19A shows a composite image of FIGS. 19B-19E. FIG. 19B shows DAPI staining of nuclei. FIG. 19C shows GFP expression. FIG. 19D shows cone arrestin antibody labeling of cone photoreceptor cells. FIG. 19E shows rhodopsin antibody labeling of rod photoreceptor cells.

FIGS. 20A-20E provide fluorescence images of the retina of the eye of an African green monkey after intravitreal administration of AAV2.5T.LSV1 virions encoding GFP. FIG. 20A shows a composite image of FIGS. 20B-20E. FIG. 20B shows DAPI staining of nuclei. FIG. 20C shows GFP expression. FIG. 20D shows cone arrestin antibody labeling of cone photoreceptor cells. FIG. 20E shows rhodopsin antibody labeling of rod photoreceptor cells.

FIG. 21A shows a composite image of FIGS. 21B-21E. FIG. 21B shows DAPI staining of nuclei. FIG. 21C shows native GFP expression with no antibody labeling. FIG. 21D shows RPE 65 antibody labeling of cone photoreceptor cells. FIG. 21E shows GFP expression at 647 nm.

FIG. 22A shows a composite image of FIGS. 22B-22E. FIG. 22B shows DAPI staining of nuclei. FIG. 22C shows native GFP expression with no antibody labeling. FIG. 22D shows RPE 65 antibody labeling of cone photoreceptor cells. FIG. 22E shows GFP expression at 647 nm.

FIG. 23A shows a composite image of FIGS. 23B-23E. FIG. 23B shows DAPI staining of nuclei. FIG. 23C shows native GFP expression with no antibody labeling. FIG. 23D shows RPE 65 antibody labeling of cone photoreceptor cells. FIG. 23E shows GFP expression at 647 nm.

FIG. 24A shows a composite image of FIGS. 26B-26E. FIG. 24B shows DAPI staining of nuclei. FIG. 24C shows native GFP expression with no antibody labeling. FIG. 24D shows RPE 65 antibody labeling of cone photoreceptor cells. FIG. 24E shows GFP expression at 647 nm.

FIG. 25A shows a composite image of FIGS. 25B-25E. FIG. 25B shows DAPI staining of nuclei. FIG. 25C shows native GFP expression with no antibody labeling. FIG. 25D shows RPE 65 antibody labeling of cone photoreceptor cells. FIG. 25E shows GFP expression at 647 nm.

FIG. 27A shows the neutralizing antibody profile of IVIG against AAV2.5T.LSV1-CMV-GFP (N=3 for each dilution). FIG. 27B shows the neutralizing antibody profile of IVIG against AAV2-CMV-GFP (N=2 or 3 for each dilution).

DETAILED DESCRIPTION

Figure 1A:
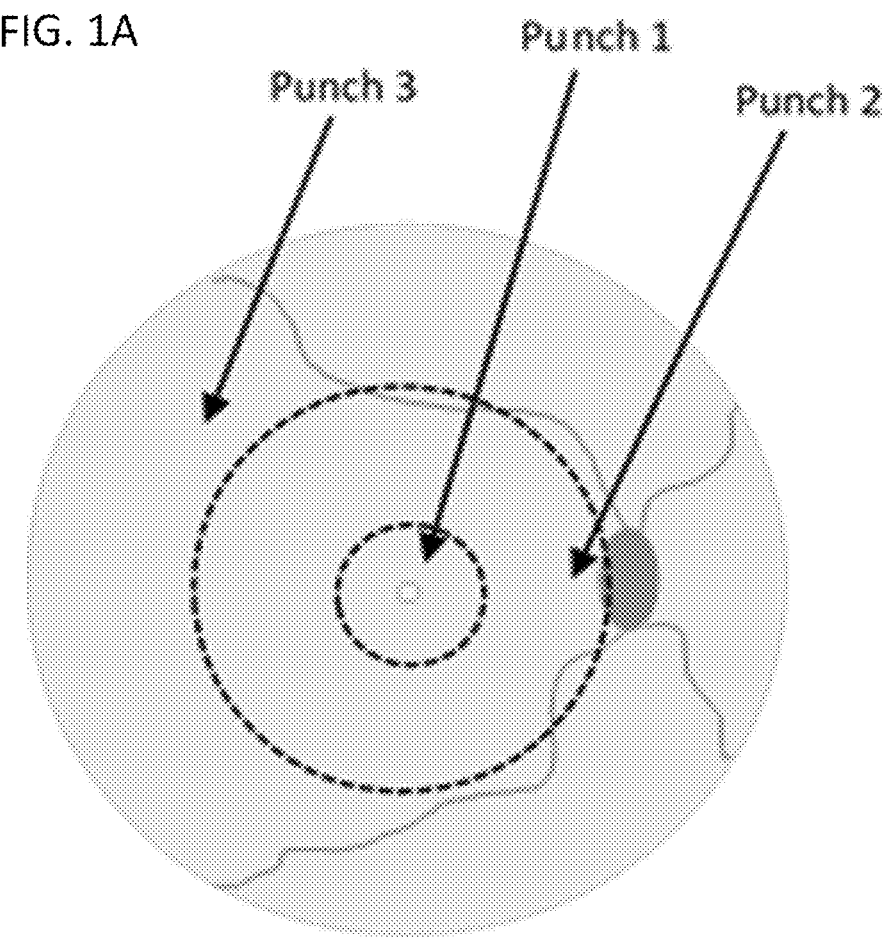
FIG. 1A shows a schematic representation of a retina and concentric sample punch locations. Punch 1 contains the macula (small circular indentation); Punch 2 contains the parafovea; the remaining tissue contains the peripheral retina including the blood arcades.

The present disclosure provides variant AAV capsid proteins and recombinant adeno-associated virus (AAV) virions having one or more variant AAV capsid proteins. In some embodiments, the recombinant AAV virions exhibit one or more of the following characteristics: 1) increased infectivity of a retinal cell; 2) altered tropism; 3) increased binding to heparin and/or heparan sulfate proteoglycans and/or the inner limiting membrane (ILM); and 4) an increased ability to infect and/or deliver a therapeutic gene product across the ILM when administered intravitreally, as compared to a corresponding viral vector comprising its native, wild-type, and/or parental capsid protein instead of a modified capsid protein disclosed herein. Also provided are pharmaceutical compositions and methods for the use of any of the compositions disclosed herein for promoting the expression of a therapeutic gene product in cells, e.g., retinal cells, in an individual, e.g., for the treatment or prophylaxis of a disease or disorder.

I. Definitions

Unless otherwise defined, all technical terms used herein have the same meaning as commonly understood by one of ordinary skill in the art.

The terminology used herein is for the purpose of describing particular examples only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The term "comprising" as used herein is synonymous with "including" or "containing", and is inclusive or open-ended.

Any reference to "or" herein is intended to encompass "and/or" unless otherwise stated.

Reference to "about" a value or parameter herein includes (and describes) variations that are directed to that value or parameter per se. For example, description referring to "about X" includes description of "X".

In some embodiments of the invention, an "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The terms "treat," "treating", "treatment," "ameliorate" or "ameliorating" and other grammatical equivalents as used herein, refer to alleviating, abating or ameliorating an ocular disease or disorder or symptoms of the ocular disease or disorder, preventing additional symptoms of the ocular disease or disorder, ameliorating the underlying metabolic causes of symptoms, inhibiting the ocular disease or disorder, e.g., arresting the development of the ocular disease or disorder, relieving the ocular disease or disorder, causing regression of the ocular disease or disorder, or stopping the symptoms of the ocular disease or disorder. The terms further include achieving a therapeutic benefit. The term "therapeutic benefit" refers to eradication or amelioration of the ocular disease or disorder being treated. Also, a therapeutic benefit is achieved with the eradication or amelioration of one or more of the physiological symptoms associated with the ocular disease or disorder such that an improvement is observed in the patient, subject, or individual notwithstanding that, in some embodiments, the patient, subject, or individual is still afflicted with the ocular disease or disorder.

In some embodiments, the methods of the invention provide prophylactic benefit; for example, the pharmaceutical compositions are administered to a patient, subject, or individual at risk of developing the ocular disease or disorder, or to a patient, subject, or individual reporting one or more of the physiological symptoms of the ocular disease or disorder, even if a diagnosis of the disease or disorder has not been made.

The terms "administer," "administering", "administration," and the like, as used herein, can refer to the methods that are used to enable delivery of therapeutics or pharmaceutical compositions to the desired site of biological action. These methods include intravitreal or subretinal injection to an eye.

The terms "effective amount", "therapeutically effective amount" or "pharmaceutically effective amount" as used herein, can refer to a sufficient amount of at least one pharmaceutical composition or compound being administered which will relieve to some extent one or more of the symptoms of the ocular disease or disorder being treated. An "effective amount", "therapeutically effective amount" or "pharmaceutically effective amount" of a pharmaceutical composition may be administered to a subject in need thereof as a unit dose (as described in further detail elsewhere herein).

The term "pharmaceutically acceptable" as used herein, can refer to a material, such as a carrier or diluent, which does not abrogate the biological activity or properties of a compound disclosed herein, and is relatively nontoxic (i.e., when the material is administered to an individual it does not cause undesirable biological effects nor does it interact in a deleterious manner with any of the components of the composition in which it is contained).

The term "pharmaceutical composition," as used herein, can refer to a biologically active compound, optionally mixed with at least one pharmaceutically acceptable chemical component, such as, though not limited to carriers, stabilizers, diluents, dispersing agents, suspending agents, thickening agents, excipients and the like.

An "AAV vector" or "rAAV vector" as used herein refers to an adeno-associated virus (AAV) vector or a recombinant AAV (rAAV) vector comprising a polynucleotide sequence not of AAV origin (e.g., a polynucleotide heterologous to AAV such as a nucleic acid sequence that encodes a therapeutic transgene, e.g., aflibercept) for transduction into a target cell or to a target tissue. In general, the heterologous polynucleotide is flanked by at least one, and generally by two, AAV inverted terminal repeat sequences (ITRs). The term rAAV vector encompasses both rAAV vector particles and rAAV vector plasmids. A rAAV vector may either be single-stranded (ssAAV) or self-complementary (scAAV).

An "AAV virus" or "AAV viral particle" or "rAAV vector particle" or "rAAV particle" or "recombinant AAV virion" refers to a viral particle comprising at least one AAV capsid protein and a polynucleotide rAAV vector. If the particle comprises a heterologous polynucleotide (e.g., a polynucleotide other than a wild-type AAV genome such as a transgene to be delivered to a target cell or target tissue), it is typically referred to as a "rAAV vector particle" or a "rAAV vector".

The term "packaging" as used herein can refer to a series of intracellular events that can result in the assembly and encapsidation of a rAAV particle.

AAV "rep" and "cap" genes refer to polynucleotide sequences encoding replication and encapsidation proteins of adeno-associated virus. AAV rep and cap are referred to herein as AAV "packaging genes."

The terms "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component or toxin. Also included within the definition are, for example, polypeptides containing one or more analogs of an amino acid (including, for example, unnatural amino acids, etc.), as well as other modifications known in the art.

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, may refer to double- and single-stranded molecules.

As used herein, "recombinant" can refer to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. Thus, for example, a protein synthesized by a microorganism is recombinant, for example, if it is synthesized from an mRNA synthesized from a recombinant gene present in the cell.

The term "anti-VEGF gene product" includes any therapeutic agent, including proteins, polypeptides, peptides, fusion protein, multimeric proteins, antibody, human monoclonal antibody, antibody fragment, aptamer, kinase inhibitor, receptor or receptor fragment, or nucleic acid molecule, that can reduce, interfere with, disrupt, block and/or inhibit the activity or function of an endogenous VEGF and/or an endogenous VEGF receptor (VEGFR), or the VEGF-VEGFR interaction or pathway in vivo. An anti-VEGF gene product can be any one of the known therapeutic gene products that can reduce new blood vessel growth or formation and/or edema, or swelling, when delivered into a cell, tissue, or a subject in vivo, e.g., ranibizumab, brolucizumab, or bevacizumab. In some embodiments, an anti-VEGF gene product can be naturally occurring, non-naturally occurring, or synthetic. In some embodiments, an anti-VEGF gene product can be derived from a naturally occurring molecule that was subsequently modified or mutated to confer an anti-VEGF activity. In some embodiments, an anti-VEGF gene product is a fusion or chimeric protein. In such proteins, functional domains or polypeptides are artificially fused to a moiety or a polypeptide to make a fusion or chimeric protein that can sequester VEGF in vivo or function as a VEGFR decoy. In some embodiments, an anti-VEGF gene product is a fusion or chimeric protein that blocks endogenous VEGFR from interacting with its ligands.

As used herein, "VEGF" can refer to any isoform of VEGF or VEGF family member, unless required otherwise, including, but not limited to, VEGF-A, VEGF-B, VEGF-C, VEGF-D, VEGF-E, VEGF-F, placenta growth factor (PGF) or any combination, or any functional fragment or variant thereof. As used herein, "VEGF receptor" or "VEGFR" or "VEGF-R" can be used to refer to any one of the receptors of VEGF, including, but not limited to, VEGFR-1 (or Flt-1), VEGFR-2 (or Flk-1/KDR), and VEGFR-3 (or Flt-4). VEGFR can be a membrane bound or soluble form, or a functional fragment or truncation of a receptor.

As used herein "sFlt-1 protein" refers to a polypeptide sequence, or functional fragment thereof, with at least 90%, or more, homology to the naturally occurring human sFLT-1 sequence, such that the sFlt-1 protein or polypeptide binds to VEGF and/or the VEGF receptor, unless explicitly stated otherwise. Homology refers to the % conservation of residues of an alignment between two sequences. A naturally occurring human sFLT-1 protein may include any suitable variants of sFLT-1, including, but not limited to functional fragments, sequences comprising insertions, deletions, substitutions, pseudofragments, pseudogenes, splice variants or artificially optimized sequences.

"Operatively linked" or "operably linked" or "coupled" can refer to a juxtaposition of genetic elements, wherein the elements are in a relationship permitting them to operate in an expected manner. For instance, a promoter can be operatively linked to a coding region if the promoter helps initiate transcription of the coding sequence. There may be intervening residues between the promoter and coding region so long as this functional relationship is maintained.

An "expression vector" as used herein encompasses a vector, e.g. plasmid, minicircle, viral vector, liposome, and the like as discussed above or as known in the art, comprising a polynucleotide which encodes a gene product of interest, and is used for effecting the expression of a gene product in an intended target cell. An expression vector may also comprise control elements operatively linked to the encoding region to facilitate expression of the gene product in the target. The combination of control elements, e.g. promoters, enhancers, UTRs, miRNA targeting sequences, etc., and a gene or genes to which they are operably linked for expression is sometimes referred to as an "expression cassette." Many such control elements are known and available in the art or can be readily constructed from components that are available in the art.

A "gene product" is a molecule resulting from expression of a particular gene. Gene products include, e.g., a polypeptide, an aptamer, an interfering RNA, an mRNA, and the like. In particular embodiments, a "gene product" is a polypeptide, peptide, protein or interfering RNA including short interfering RNA (siRNA), miRNA, or small hairpin RNA (shRNA). In particular embodiments, a gene product is a therapeutic gene product, e.g., a therapeutic protein.

The term "heterologous" can refer to an entity that is genotypically distinct from that of the rest of the entity to which it is being compared. For example, a polynucleotide introduced by genetic engineering techniques into a plasmid or vector derived from a different species can be a heterologous polynucleotide. A promoter removed from its native coding sequence and operatively linked to a coding sequence with which it is not naturally found linked can be a heterologous promoter.

The methods, compositions, and kits described herein may employ, unless otherwise indicated, conventional techniques and descriptions of molecular biology (including recombinant techniques), cell biology, biochemistry, immunochemistry and ophthalmic techniques, which are within the skill of those who practice in the art. Such conventional techniques include methods for observing and analyzing the retina, or vision in a subject, cloning and propagation of recombinant virus, formulation of a pharmaceutical composition, and biochemical purification and immunochemistry. Specific illustrations of suitable techniques can be had by reference to the examples herein. However, equivalent conventional procedures can, of course, also be used. Such conventional techniques and descriptions can be found in standard laboratory manuals such as Green, et al., Eds., Genome Analysis: A Laboratory Manual Series (Vols. I-IV) (1999); Weiner, et al., Eds., Genetic Variation: A Laboratory Manual (2007); Dieffenbach, Dveksler, Eds., PCR Primer: A Laboratory Manual (2003); Bowtell and Sambrook, DNA Microarrays: A Molecular Cloning Manual (2003); Mount, Bioinformatics: Sequence and Genome Analysis (2004); Sambrook and Russell, Condensed Protocols from Molecular Cloning: A Laboratory Manual (2006); and Sambrook and Russell, Molecular Cloning: A Laboratory Manual (2002) (all from Cold Spring Harbor Laboratory Press); Stryer, L., Biochemistry (4th Ed.) W.H. Freeman, N.Y. (1995); Gait, "Oligonucleotide Synthesis: A Practical Approach" IRL Press, London (1984); Nelson and Cox, Lehninger, Principles of Biochemistry, 3rd Ed., W.H. Freeman Pub., New York (2000); and Berg et al., Biochemistry, 5th Ed., W.H. Freeman Pub., New York (2002), all of which are herein incorporated by reference in their entirety for all purposes.

A "variant AAV capsid protein" as used herein refers to an AAV capsid protein, where the AAV capsid protein comprises at least one amino acid difference (e.g., amino acid substitution, amino acid insertion, amino acid deletion) relative to a corresponding parental AAV capsid protein, where the AAV capsid protein does not correspond to the amino acid sequence present in a naturally occurring AAV capsid protein. In some embodiments the variant AAV capsid protein confers increased binding to heparin and/or a heparan sulfate proteoglycan as compared to the binding by an AAV virion comprising the corresponding parental AAV capsid protein. In certain embodiments, the variant AAV capsid protein confers: a) increased infectivity of a retinal cell compared to the infectivity of the retinal cell by an AAV virion comprising the corresponding parental AAV capsid protein; b) altered cellular tropism as compared to the tropism of an AAV virion comprising the corresponding parental AAV capsid protein; and/or c) an increased ability to bind and/or cross the ILM as compared to an AAV virion comprising the corresponding parental AAV capsid protein.

A "modified sequence" as used herein refers to a sequence comprising one or more substitutions, insertions, and/or deletions compared to the corresponding sequence of a parental AAV or a parental AAV capsid protein.

A "helper virus" for AAV refers to a virus that allows AAV (e.g., wild-type AAV) to be replicated and packaged by a mammalian cell. A variety of such helper viruses for AAV are known in the art, including adenoviruses, herpesviruses, and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper function(s)" refers to function(s) encoded in a helper virus genome which allow AAV replication and packaging (in conjunction with other requirements for replication and packaging described herein). As described herein, "helper function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with a rAAV vector.

An "infectious" virion or viral particle is one that comprises a competently assembled viral capsid and is capable of delivering a polynucleotide component into a cell for which the viral species is tropic. The term does not necessarily imply any replication capacity of the virion. Assays for counting infectious virions are described elsewhere in this disclosure and in the art. Viral infectivity can be expressed as the ratio of infectious virions to total virions. Methods of determining the ratio of infectious virions to total virions are known in the art. See, e.g., Grainger et al. (2005) Mol. Ther. 11:S337 (describing a TCID50 infectious titer assay); and Zolotukhin et al. (1999) Gene Ther. 6:973.

II. Variant AAV Capsid Proteins

Provided herein are variant adeno-associated virus (AAV) capsid proteins. In some embodiments, the variant AAV capsid protein disclosed herein comprises a modified sequence comprising one or more amino acid substitutions within amino acid residues 570-579 relative to a parental AAV capsid protein, wherein the modified sequence comprises HKFKSGD (SEQ ID NO: 1), and wherein the amino acid residue numbering corresponds to an AAV5 VP1 capsid protein. In some embodiments, the variant AAV capsid protein comprises a modified sequence comprising one or more amino acid substitutions within amino acid residues 570-579 relative to a parental AAV capsid protein, wherein the modified sequence comprises $X_1X_2$HKFKSGD$X_3$ (SEQ ID NO: 2), and wherein the amino acid residue numbering corresponds to an AAV5 VP1 capsid protein, wherein $X_{1-3}$ can independently be any amino acid. In some embodiments, each of $X_{1-3}$ is independently selected from A, L, G, S, and T. In some embodiments, each of $X_{1-3}$ is independently selected from A, L, G, S, and T. In some embodiments, $X_1$ is L. In some embodiments, $X_2$ is A. In some embodiments, $X_3$ is A. In some embodiments, the variant AAV capsid protein comprises a modified sequence comprising one or more amino acid substitutions within amino acid residues 570-579 relative to a parental AAV capsid protein, wherein the modified sequence comprises LAHKFKSGDA (SEQ ID NO: 3), a sequence having at least 80% or at least 90% homology with SEQ ID NO: 3; having at least 80% or at least 90% sequence identity with SEQ ID NO: 3; or having four or more, five or more, six or more, seven or more, eight or more, or nine or more consecutive amino acids within SEQ ID NO: 3, and wherein the amino acid residue numbering corresponds to an AAV5 VP1 capsid protein. In some embodiments, the modified sequence comprises LAHKFKSGDA (SEQ ID NO: 3).

While reference is made herein to amino acid modifications of capsid proteins (including specific amino acid substitutions and insertions) using the amino acid numbering corresponding to AAV5 VP1 capsid protein, it is understood that any of these amino acid modifications may also be introduced in the capsid protein of AAVs of other serotypes, e.g., at positions corresponding to those of AAV5 VP1. AAV protein sequences share significant homology and similar amino acid numbering, and the skilled artisan can readily determine amino acid residues in other AAV serotypes that correspond to those specifically described herein for AAV5 VP1.

In some embodiments, the parental AAV capsid protein is a wild-type AAV capsid protein, for example an AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), avian AAV, bovine AAV, canine AAV, equine AAV, primate AAV, non-primate AAV, or ovine AAV capsid protein. In some embodiments, the parental AAV capsid protein is an AAV5 capsid protein. In some embodiments, the parental AAV capsid protein is a VP1, VP2, or VP3 capsid protein. In some embodiments, the parental AAV capsid protein is an AAV5 VP1 capsid protein.

In some embodiments, the parental AAV capsid protein is a variant AAV capsid protein. In some embodiments, the parental AAV capsid protein is a variant of an AAV1, an AAV2, an AAV3, an AAV4, an AAV5, an AAV6, an AAV7, an AAV8, an AAV9, an AAV10, an avian AAV, a bovine AAV, a canine AAV, an equine AAV, a primate AAV, a non-primate AAV, or an ovine AAV capsid protein. In some embodiments, the parental AAV capsid protein is a variant of an AAV5 VP1 capsid protein. In some embodiments, the parental AAV capsid protein is a variant of an AAV5 VP1 capsid protein having at least 90%, at least 95%, at least 98%, or at least 99% homology to SEQ ID NO: 4. In some embodiments, the parental AAV capsid protein is a variant of an AAV5 VP1 capsid protein having at least 90%, at least 95%, at least 98%, or at least 99% sequence identity to SEQ ID NO: 4. In some embodiments, the parental AAV capsid protein is a hybrid capsid protein. In some embodiments, the parental AAV capsid protein is a hybrid of an AAV2 capsid protein and an AAV5 capsid protein. In some embodiments, the parental AAV capsid protein is an AAV2.5T capsid protein, or a variant thereof having at least 90%, at least 95%, at least 98%, or at least 99% homology to an AAV2.5T capsid protein. In some embodiments, the parental AAV capsid protein is an AAV 2.5T capsid protein, or a variant thereof having at least 90%, at least 95%, at least 98%, or at least 99% sequence identity to an AAV2.5T capsid protein. In some embodiments, the parental AAV capsid protein is an AAV 2.5T capsid protein. In some embodiments, the parental AAV capsid protein is a VP1, VP2, or VP3 capsid protein. In some embodiments, the parental AAV capsid protein is an AAV2.5T VP1 capsid protein, or a variant thereof having at least 90%, at least 95%, at least 98%, or at least 99% homology to an AAV2.5T VP1 capsid protein (SEQ ID NO: 5). In some embodiments, the parental AAV capsid protein is an AAV2.5T VP1 capsid protein, or a variant thereof having at least 90%, at least 95%, at least 98%, or at least 99% sequence identity to an AAV2.5T VP1 capsid protein (SEQ ID NO: 5).

In some embodiments, the variant AAV capsid protein comprises a capsid sequence having at least 85% homology to the amino acid sequence set forth in SEQ ID NO: 4 or SEQ ID NO: 5. In some embodiments, the variant AAV capsid protein comprises a capsid sequence having at least 85% sequence identity to the amino acid sequence set forth in SEQ ID NO: 4 or SEQ ID NO: 5. In some embodiments, the variant AAV capsid protein comprises a capsid sequence having at least 85%, at least 90%, at least 95%, at least 98%, at least 99%, or 100% homology to the amino acid sequence set forth in SEQ ID NO: 6 or SEQ ID NO: 7. In some embodiments, the variant AAV capsid protein comprises a capsid sequence having at least 85%, at least 90%, at least 95%, at least 98%, at least 99%, or 100% sequence identity to the amino acid sequence set forth in SEQ ID NO: 6 or SEQ ID NO: 7. In some embodiments, the variant AAV capsid protein comprises SEQ ID NO: 6 or SEQ ID NO: 7. In some embodiments, the variant AAV capsid protein comprises SEQ ID NO: 7.

In particular embodiments, the variant AAV capsid protein, when present in a recombinant AAV virion, confers increased infectivity of a retinal cell as compared to the infectivity of the retinal cell by a recombinant AAV virion comprising the corresponding parental AAV capsid protein. In particular embodiments, the variant AAV capsid protein, when present in a recombinant AAV virion, confers increased infectivity of a retinal cell when administered by intravitreal injection as compared to the infectivity of the retinal cell by a recombinant AAV virion comprising the corresponding parental AAV capsid protein when administered by intravitreal injection. In some embodiments, the retinal cell is one or more of a photoreceptor cell (e.g., rods; cones), a retinal ganglion cell (RGC), a retinal pigment epithelium (RPE) cell, a Müller cell, an amacrine cell, a bipolar cell, and a horizontal cell. In particular embodiments, the variant AAV capsid protein, when present in a recombinant AAV virion, confers altered tropism to the recombinant AAV virion as compared to the tropism of a recombinant AAV virion comprising the corresponding parental AAV capsid protein. In particular embodiments, the variant AAV capsid protein, when present in a recombinant AAV virion, confers increased binding to heparin and/or heparan sulfate, and/or increased ability to bind and cross the inner limiting membrane (ILM) following intravitreal injection, as compared to a recombinant AAV virion comprising the corresponding parental AAV capsid protein.

III. Polynucleotides and Cells

Also provided herein are polynucleotides encoding one or more variant AAV capsid proteins described herein. In particular embodiments, the polynucleotide is an expression vector. In some embodiments, the expression vector comprises the polynucleotide sequence encoding the modified capsid protein described herein operably linked to a promoter sequence, e.g., a promoter sequence that drives expression of the polynucleotide in a cell. In certain embodiments, the cell is a host cell. The host cell may be used to produce virions comprising the modified capsid protein. Exemplary host cells include mammalian cells (e.g. HEK293 cells), insect cells (e.g. SF9 cells), microorganisms and yeast. In some embodiments, the cell comprises an AAV rep gene, such as an AAV rep gene that encodes an AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV rep protein or variant thereof. In some embodiments, the AAV rep gene is stably maintained in the cell.

Also provided herein are cells comprising a polynucleotide or vector that encodes a modified capsid protein described herein. In particular embodiments, the polynucleotide is an expression vector, and the expression vector comprises a polynucleotide sequence encoding a variant capsid described herein operably linked to a promoter sequence, e.g., a promoter sequence that drives expression of the polynucleotide in the cell. In some embodiments, the polynucleotide or vector is stably maintained in the cell. In some embodiments, the cell further comprises an AAV rep gene. In some embodiments, the AAV rep gene is stably maintained in the cell. In certain embodiments, the polynucleotide or vector further comprises a sequence that encodes a rep protein, e.g., an AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV rep protein or variant thereof.

In some embodiments, the cell further comprises a polynucleotide cassette comprising a sequence that encodes a gene product, e.g., a therapeutic gene product, such as a therapeutic gene product described herein. In certain embodiments, the polynucleotide cassette is flanked by one or more AAV inverted terminal repeats (ITRs). In certain embodiments, the polynucleotide cassette is flanked on the 5' and 3' ends by AAV ITRs. In some embodiments, the one or more ITRs are AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV ITRs or variants thereof. In some embodiments, the one or more ITRs are AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV ITRs. In some embodiments, the one or more ITRs are an AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV ITR comprising one or more insertions, deletions, and/or substitutions of nucleotides.

IV. Virions and Methods of Producing the Same

Also provided herein are virions, e.g. recombinant AAV virions, comprising a variant AAV capsid protein described herein.

In some embodiments, the recombinant AAV virion, further comprises a polynucleotide cassette comprising a sequence that encodes a gene product, e.g., a therapeutic gene product, such as a therapeutic gene product described herein. In certain embodiments, the polynucleotide cassette is flanked by one or more AAV inverted terminal repeats (ITRs), such as AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV ITRs or variants thereof. In certain embodiments, the polynucleotide cassette is flanked on the 5' and 3' ends by AAV ITRs. In some embodiments, the one or more ITRs are AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV ITRs or variants thereof. In some embodiments, the one or more ITRs are an AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV ITR comprising one or more insertions, deletions, and/or substitutions of nucleotides. In some embodiments, the one or more ITRs are an AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV ITR.

In certain embodiments, the gene product inhibits neovascularization, e.g., choroidal neovascularization (CNV), in the retina of the subject. It has been found that many cellular factors play important roles in regulation in CNV generation, among which may include but are not limited to vascular endothelial growth factor (VEGF), VEGF receptor (VEGFR), platelet-derived growth factor (PDGF), hypoxia inducible factor (HIF), angiopoietin (Ang) and other cytokines, mitogen-activated protein kinases (MAPK). In some embodiments, the gene product is an inhibitor of one or more of VEGF, VEGFR, PDGF, HIF, Ang, and MAPK.

In certain embodiments, the gene product inhibits neovascularization, e.g., choroidal neovascularization (CNV), in the retina of the subject. It has been found that many cellular factors play important roles in regulation in CNV generation, among which may include but are not limited to vascular endothelial growth factor (VEGF), VEGF receptor (VEGFR), platelet-derived growth factor (PDGF), hypoxia inducible factor (HIF), angiopoietin (Ang) and other cytokines, and mitogen-activated protein kinases (MAPK). In some embodiments, the gene product is an inhibitor of one or more of VEGF, VEGFR, PDGF, HIF, Ang, and MAPK.

In some embodiments, the gene product is an interfering RNA, an aptamer, or a protein. In some embodiments, therapeutic gene product is an interfering RNA, an aptamer, or a protein. In some embodiments, the gene product (or therapeutic gene product) is a siRNA, a miRNA, or a protein. In some embodiments, the gene product (or therapeutic gene product) is a site-specific nuclease that provides for site-specific knock-down of gene function. In some embodiments, the gene product (or therapeutic gene product) is an interfering RNA. In some embodiments, the gene product (or therapeutic gene product) is a siRNA or miRNA.

In some embodiments, the gene product (or therapeutic gene product) is an anti-VEGF gene product. In some embodiments, the gene product (or therapeutic gene product) is an anti-VEGF interfering RNA. In some embodiments, the gene product (or therapeutic gene product) is an anti-VEGF siRNA or miRNA.

In some embodiments, the gene product (or therapeutic gene product) is an aptamer. Exemplary aptamers of interest include an aptamer against vascular endothelial growth factor (VEGF). See, e.g., Ng et al. (2006) Nat. Rev. Drug Discovery 5:123; and Lee et al. (2005) Proc. Natl. Acad. Sci. USA 102:18902. Also suitable for use is a PDGF-specific aptamer, e.g., E10030; see, e.g., Ni and Hui (2009) Ophthalmologica 223:401; and Akiyama et al. (2006) J. Cell Physiol. 207:407).

In some embodiments, the gene product (or therapeutic gene product) is a protein. The protein is generally a protein that enhances function of a retinal cell, e.g., the function of a rod or cone photoreceptor cell, a retinal ganglion cell, a Müller cell, a bipolar cell, an amacrine cell, a horizontal cell, or a retinal pigmented epithelial cell. Exemplary proteins include neuroprotective polypeptides (e.g., GDNF, CNTF, NT4, NGF, and NTN); anti-angiogenic polypeptides (e.g., a soluble vascular endothelial growth factor (VEGF) receptor; a VEGF-binding antibody; a VEGF-binding antibody fragment (e.g., a single chain anti-VEGF antibody); endostatin; tumstatin; angiostatin; a soluble Flt protein (Lai et al. (2005) Mol. Ther. 12:659); an Fc fusion protein comprising a soluble Flt protein (see, e.g., Pechan et al. (2009) Gene Ther. 16:10); pigment epithelium-derived factor (PEDF); a soluble Tie-2 receptor; etc.); tissue inhibitor of metalloproteinases-3 (TIMP-3); an opsin, e.g., a rhodopsin; anti-apoptotic polypeptides (e.g., Bcl-2, Bcl-X1); and the like. Suitable polypeptides include, but are not limited to, glial derived neurotrophic factor (GDNF); fibroblast growth factor 2; neurturin (NTN); ciliary neurotrophic factor (CNTF); nerve growth factor (NGF); neurotrophin-4 (NT4); brain derived neurotrophic factor (BDNF); epidermal growth factor; rhodopsin; X-linked inhibitor of apoptosis; and Sonic hedgehog.

Suitable opsins include, e.g., a light-responsive opsin as described in U.S. Patent Publication No. 2007/0261127 (e.g., ChR2; Chop2); U.S. Patent Publication No. 2001/0086421; U.S. Patent Publication No. 2010/0015095; and Diester et al. (2011) Nat. Neurosci. 14:387.

Suitable proteins also include retinoschisin. Suitable polypeptides include, e.g., retinitis pigmentosa GTPase regulator (RGPR)-interacting protein-1 (see, e.g., GenBank Accession Nos. Q96KN7, Q9EPQ2, and Q9GLM3); peripherin-2 (Prph2) (see, e.g., GenBank Accession No. NP_000313; and Travis et al. (1991) Genomics 10:733); peripherin; a retinal pigment epithelium-specific protein (RPE65) (see, e.g., GenBank AAC39660; and Morimura et al. (1998) Proc. Natl. Acad. Sci. USA 95:3088); and the like.

Suitable proteins also include: CHM (choroideremia (Rab escort protein 1)), a polypeptide that, when defective or missing, causes choroideremia (see, e.g., Donnelly et al. (1994) Hum. Mol. Genet. 3:1017; and van Bokhoven et al. (1994) Hum. Mol. Genet. 3:1041); and Crumbs homolog 1 (CRB 1), a polypeptide that, when defective or missing, causes Leber congenital amaurosis and retinitis pigmentosa (see, e.g., den Hollander et al. (1999) Nat. Genet. 23:217; and GenBank Accession No. CAM23328).

Suitable proteins also include proteins that, when defective or missing, lead to achromotopsia, where such polypeptides include, e.g., cone photoreceptor cGMP-gated channel subunit alpha (CNGA3) (see, e.g., GenBank Accession No. NP_001289; and Booij et al. (2011) Ophthalmology 118:160-167); cone photoreceptor cGMP-gated cation channel beta-subunit (CNGB3) (see, e.g., Kohl et al. (2005) Eur J Hum Genet. 13(3):302); guanine nucleotide binding protein (G protein); alpha transducing activity polypeptide 2 (GNAT2) (ACHM4); and ACHM5; and polypeptides that, when defective or lacking, lead to various forms of color blindness (e.g., L-opsin, M-opsin, and S-opsin). See Mancuso et al. (2009) Nature 461(7265):784-787.

In some embodiments, the gene product (or therapeutic gene product) is an anti-VEGF protein. In some embodiments, the anti-VEGF protein is a sFlt-1 protein or fragment thereof or an anti-VEGF antibody or fragment thereof. In some embodiments, the anti-VEGF protein is an anti-VEGF antibody or fragment thereof, such as aflibercept, ranibizumab, and bevacizumab or fragments thereof. In some embodiments, the anti-VEGF protein is a sFlt-1 protein.

The soluble truncated form of the VEGF receptor FLT-1, sFLT-1, is the only known endogenous specific inhibitor of VEGF. In nature, it is generated by alternative mRNA splicing and lacks the membrane-proximal immunoglobulin-like domain, the transmembrane spanning region and the intracellular tyrosine-kinase domain. Structurally, FLT-1 and sFLT-1 proteins may both comprise multiple functional domains. In some variants, FLT and sFLT proteins commonly share 6 interlinked domains; 3 domains involved in dimerization of the protein and 3 domains involved in the binding of a ligand, such as VEGF. sFLT-1 is not restricted to the cellular membrane. Unbound sFLT-1 may diffuse freely in extracellular space or solution.

The interaction between sFLT-1 and the VEGF receptor is specific and can be competed away with 100-fold excess unlabeled VEGF. In some cases, the angiostatic activity of sFLT-1 may result from inhibition of VEGF by two mechanisms: i) sequestration of VEGF, to which it binds with high affinity, and ii) formation of inactive heterodimers with membrane-spanning isoforms of the VEGF receptors FLTt-1 and FLK-1/KDR. As known in the art, in vitro binding assays have indicated that sFLT-1 binds VEGF with high affinity and may also inhibit VEGF driven proliferation of human umbilical vein endothelial cells. In animal models for cancer, sFLT-1 inhibits tumor growth. In some cases, sFLT-1 may function in a substoichiometric or dominant negative manner, as excess VEGF in the extracellular space may be prevented from binding and subsequently activating the VEGF receptor. These properties of sFLT-1 have been described in Kendall and Thomas, 1993; Proc Natl Acad Sci. 90: 10705-10709, which is incorporated herein by reference in its entirety. Functional fragments of sFLT-1 can be used in place of the full-length protein. More specifically, the VEGF binding domain (domain 2), or alternatively domain 2 of sFLT-1 plus domain 3 from sFLT1, KDR, or another family member, can be used to bind and inactivate VEGF. Such functional fragments are described in Wiesmann et al., 1997; Cell, 91: 695-704, which is incorporated herein by reference in its entirety.

In some embodiments, the sFlt-1 protein is the naturally occurring protein sFlt-1, as described in U.S. Pat. No. 5,861,484 and the sequence disclosed by SEQ ID NO: 109 in US2013/0323302. An exemplary sFlt-1 amino acid sequence is disclosed herein as SEQ ID NO: 13. It also includes, but is not limited to functional fragments thereof, including sequences of sFlt-1 domain 2 or those set forth in SEQ ID NO: 121 of U.S. Patent Application Publication No. 2013/0323302, as well as related constructs, such as the VEGF-binding fusion proteins disclosed in U.S. Pat. No. 7,635,474. An exemplary sFlt-1 functional fragment is disclosed herein as SEQ ID NO: 14. In some embodiments, the sFLT-1 protein is at least about 90%, 91%, 92%, 93%, 94%, 95%, 96%, 97%, 98%, 99%, 99.9%, 99.99% or 100% homologous to SEQ ID NO: 13 or SEQ ID NO: 14. In some embodiments, the sFLT-1 protein has at least about 90%, 91%, 92%, 93%, 94%, 95%, 96%, 97%, 98%, 99%, 99.9%, 99.99% or 100% sequence identity with SEQ ID NO: 13 or SEQ ID NO: 14. An anti-VEGF protein may also include any of the sFLT-1 proteins, variants or fragments thereof described in U.S. Patent Application Publication No. 2013/0323302.

In some embodiments, the sFLT-1 protein is at least about 90%, 91%, 92%, 93%, 94%, 95%, 96%, 97%, 98%, 99%, 99.9%, 99.99% or 100% homologous to the naturally occurring human sFLT-1 protein sequence. In some embodiments, the sFLT-1 protein is at most about 90%, 91%, 92%, 93%, 94%, 95%, 96%, 97%, 98%, 99%, 99.9%, 99.99% or 100% homologous to the naturally occurring human sFLT-1 protein sequence. In some embodiments, the sFLT-1 protein has at least about 90%, 91%, 92%, 93%, 94%, 95%, 96%, 97%, 98%, 99%, 99.9%, 99.99% or 100% sequence identity with the naturally occurring human sFLT-1 protein sequence. In some embodiments, the sFLT-1 protein has at most about 90%, 91%, 92%, 93%, 94%, 95%, 96%, 97%, 98%, 99%, 99.9%, 99.99% or 100% sequence identity with the naturally occurring human sFLT-1 protein sequence. In some embodiments, the sFLT-1 protein is at least about 90%, 91%, 92%, 93%, 94%, 95%, 96%, 97%, 98%, 99%, 99.9%, 99.99% or 100% spatially homologous to the naturally occurring human sFLT-1 protein conformation. In some cases, the sFLT-1 protein is at most about 90%, 91%, 92%, 93%, 94%, 95%, 96%, 97%, 98%, 99%, 99.9%, 99.99% or 100% spatially homologous to the naturally occurring human sFLT-1 protein conformation.

In some embodiments, the anti-VEGF protein is an anti-VEGF antibody. In some embodiments, the anti-VEGF protein is ranibizumab (commercially available under the trademark Lucentis® (Genentech, San Francisco, Calif.), see FIG. 1 of U.S. Pat. No. 7,060,269 for the heavy chain and light chain variable region sequences of ranibizumab); bevacizumab (commercially available under the trademark Avastin® (Genentech, San Francisco, Calif.), see FIG. 1 of U.S. Pat. No. 6,054,297 for the heavy chain and light chain variable region sequences of bevacizumab); aflibercept (commercially available under the trademark Eylea® (Regeneron, Tarrytown, N.Y.)); or brolucizumab, see U.S. Pat. No. 10,035,850. In certain embodiments, bevacizumab includes the following heavy and light chain variable domain sequences, respectively: EVQLVESGG-GLVQPGGSLRLSCAASGYTFTNYGMNWVRQAPGK-GLEWVGWINTYTGEPT YAADFKRRFTFSLDTSK-STAYLQMNSLRAEDTAVYYCAKYPHYYGSSHWY-FDVWGQGTL (SEQ ID NO: 8); and DIQMTQSPSSL-SASVGDRVTITCSASQDIS-NYLNWYQQKPGKAPKVLIYFTSSLHSGVPSRFS GSGSGTDFTLTISSLQPEDFA-TYYCQQYSTVPWTFGQGTKVEIKRTV (SEQ ID NO: 9). In certain embodiments, ranibizumab includes the following heavy and light chain variable domain sequences, respectively: EVQLVESGGGLVQPGGSLRLS-CAASGYDFTHYGMNWVRQAPGK-GLEWVGWINTYTGEPT YAADFKRRFTFSLDTSK-STAYLQMNSLRAEDTAVYYCAKYPYYYGTSHWY-FDVWGQGTL (SEQ ID NO: 10); and DIQLTQSPSSL-SASVGDRVTITCSASQDIS-NYLNWYQQKPGKAPKVLIYFTSSLHSGVPSRFS GSGSGTDFTLTISSLQPEDFA-TYYCQQYSTVPWTFGQGTKVEIKRTV (SEQ ID NO: 11). In certain embodiments, aflibercept includes the following amino acid sequence: MVSYWDTGVLLCAL-LSCLLLTGSSSGSDTGRPFVEMYSEIPEIIHMTEGREL-VIPCRVTSPNI TVTLKKFPLDTLIPDGKRIIWDSRKGFIISNATYKEI-GLLTCEATVNGHLYKTNYLTHRQTNT IIDVVLSP-SHGIELSVGEKLVLNCTARTELNVGIDFNWEY-PSSKHQHKKLVNRDLKTQSGSE MKKFLSTLTIDGVTRSDQGLYTCAASSGLMTKKN-STFVRVHEKDKTHTCPPCPAPELLGGP SVFLFPPKPKDTLMISRTPEVTCVVVDVSHEDPE-VKFNWYVDGVEVHNAKTKPREEQYNST YRVVSVLTVLHQDWLNGKEYKCKVSNKALPA-PIEKTISKAKGQPREPQVYTLPPSRDELTK NQVSLT-CLVKGFYPSDIAVEWESNGQPEN-NYKTTPPVLDSDGSFFLYSKLTVDKSRWQQGN VFSCSVMHEALHNHYTQKSLSLSPGK (SEQ ID NO:12). In certain embodiments, aflibercept includes the following amino acid sequence:

```
                                        (SEQ ID NO: 15)
EIVMTQSPSTLSASVGDRVIITCQASEIIHSWLAWYQQKPGKAPKLLIYL

ASTLASGVPSRFSGSGSGAEFTLTISSLQPDDFATYYCQNVYLASTNGAN

FGQGTKLTVLGGGGSGGGGSGGGGSGGGGSEVQLVESGGGLVQPGGSLR

LSCTASGFSLTDYYYMTWVRQAPGKGLEWVGFIDPDDDPYYATWAKGRFT

ISRDNSKNTLYLQMNSLRAEDTAVYYCAGGDHNSGWGLDIWGQGTLVTVS

S.
```

These sequences can be expressed from DNA encoding such sequences using the genetic code, a standard technique that is understood by those skilled in the art. As can be appreciated by those with skill in the art, due to the degeneracy of the genetic code, anti-VEGF protein sequences can be readily expressed from a number of different DNA sequences.

In some cases, the gene product (or therapeutic gene product) is a site-specific endonuclease that provides for site-specific knock-down of gene function, e.g., where the endonuclease knocks out an allele associated with a retinal disease. For example, where a dominant allele encodes a defective copy of a gene that, when wild-type, is a retinal structural protein and/or provides for normal retinal function, a site-specific endonuclease can be targeted to the defective allele and knock out the defective allele.

In addition to knocking out a defective allele, a site-specific nuclease can also be used to stimulate homologous recombination with a donor DNA that encodes a functional copy of the protein encoded by the defective allele. Thus, e.g., a viral vector can be used to deliver both a site-specific endonuclease that knocks out a defective allele, and can be used to deliver a functional copy of the defective allele, resulting in repair of the defective allele, thereby providing for production of a functional retinal protein (e.g., functional retinoschisin, functional RPE65, functional peripherin, etc.). See, e.g., Li et al. (2011) Nature 475:217. In some embodiments, a viral vector comprises a heterologous nucleotide sequence that encodes a site-specific endonuclease; and a heterologous nucleotide sequence that encodes a functional copy of a defective allele, where the functional copy encodes a functional retinal protein. Functional retinal proteins include, e.g., retinoschisin, RPE65, retinitis pigmentosa GTPase regulator (RGPR)-interacting protein-1, peripherin, peripherin-2, and the like.

Site-specific endonucleases that are suitable for use include, e.g., zinc finger nucleases (ZFNs); and transcription activator-like effector nucleases (TALENs), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such insertions or deletions (also referred to as "INDELs") then throw the protein out of frame and effectively knock out the gene. See, e.g., U.S. Patent Publication No. 2011/0301073.

In some embodiments, the sequence that encodes the gene product is operably linked to a promoter. In some embodiments, the sequence that encodes the gene product is operably linked to a constitutive promoter. In other embodiments, a nucleotide sequence encoding a gene product of interest is operably linked to an inducible promoter. In some instances, the sequence encoding the gene product is operably linked to a tissue-specific or cell type-specific regulatory element. For example, in some instances, the sequence encoding the gene product is operably linked to a photoreceptor-specific regulatory element (e.g., a photoreceptor-specific promoter), e.g., a regulatory element that confers selective expression of the operably linked gene in a photoreceptor cell. Suitable photoreceptor-specific regulatory elements include, e.g., a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225).

In particular embodiments, the recombinant AAV virion is capable of binding to heparin and/or heparan sulfate proteoglycans (HSPGs), e.g., with an affinity at least 2-fold, at least 3-fold, at least 4-fold, at least 5-fold, at least 10-fold, at least 20-fold, at least 50-fold, or at least 100-fold as compared to a recombinant AAV virion comprising the corresponding parental AAV capsid protein. In particular embodiments, the recombinant AAV virion is capable of binding to heparin and/or heparan sulfate proteoglycans (HSPGs), e.g., with an affinity at least 2-fold, at least 3-fold, at least 4-fold, at least 5-fold, at least 10-fold, at least 20-fold, at least 50-fold, or at least 100-fold as compared to an AAV5 virion. In particular embodiments, the recombinant AAV virion is capable of binding to heparin and/or heparan sulfate proteoglycans (HSPGs), e.g., with an affinity at least 2-fold, at least 3-fold, at least 4-fold, at least 5-fold, at least 10-fold, at least 20-fold, at least 50-fold, or at least 100-fold as compared to an AAV2.5T virion.

In particular embodiments, the recombinant AAV virion is capable of binding to the inner limiting membrane (ILM), e.g., with an affinity at least 2-fold, at least 3-fold, at least 4-fold, at least 5-fold, at least 10-fold, at least 20-fold, at least 50-fold, or at least 100-fold as compared to a recombinant AAV virion comprising the corresponding parental AAV capsid protein. In particular embodiments, the recombinant AAV virion is capable of binding to the inner limiting membrane (ILM), e.g., with an affinity at least 2-fold, at least 3-fold, at least 4-fold, at least 5-fold, at least 10-fold, at least 20-fold, at least 50-fold, or at least 100-fold as compared to an AAV5 virion. In particular embodiments, the recombinant AAV virion is capable of binding to the inner limiting membrane (ILM), e.g., with an affinity at least 2-fold, at least 3-fold, at least 4-fold, at least 5-fold, at least 10-fold, at least 20-fold, at least 50-fold, or at least 100-fold as compared to an AAV2.5T virion.

In particular embodiments, the recombinant AAV virion has increased infectivity of a retinal cell as compared to the infectivity of the retinal cell by a recombinant AAV virion comprising the corresponding parental AAV capsid protein. In particular embodiments, the recombinant AAV virion is capable of crossing the ILM. In particular embodiments, the recombinant AAV virion has increased infectivity of a retinal cell as compared to the infectivity of the retinal cell by a recombinant AAV virion comprising the corresponding parental AAV capsid protein and is capable of crossing the ILM. In particular embodiments, the recombinant AAV virion has increased infectivity of a retinal cell as compared to the infectivity of the retinal cell by an AAV5 virion. In particular embodiments, the recombinant AAV virion has increased infectivity of a retinal cell as compared to the infectivity of the retinal cell by an AAV2.5T virion. In particular embodiments, the recombinant AAV virion is capable of transducing cells of the retina when intravitreally injected into a mammal. In particular embodiments, the recombinant AAV virion is capable of crossing the ILM. In particular embodiments, the recombinant AAV virion has increased infectivity of a retinal cell when administered by intravitreal injection as compared to the infectivity of the retinal cell by a recombinant AAV virion comprising the corresponding parental AAV capsid protein when administered by intravitreal injection. In particular embodiments, the recombinant AAV virion has increased infectivity of a retinal cell when administered by intravitreal injection as compared to the infectivity of the retinal cell by an AAV5 virion when administered by intravitreal injection. In particular embodiments, the recombinant AAV virion has increased infectivity of a retinal cell when administered by intravitreal injection as compared to the infectivity of the retinal cell by an AAV2.5T virion when administered by intravitreal injection. In some embodiments, the retinal cell(s) is(are) one or more of a photoreceptor cell (e.g., rods; cones), a retinal ganglion cell (RGC), a retinal pigment epithelium (RPE) cell, a Müller cell, an amacrine cell, a bipolar cell, and a horizontal cell. In some embodiments, the retinal cell is a Müller cell, a cone cell, a rod cell, a bipolar cell, and/or a RPE cell. In some embodiments, the retinal cell is a Müller cell. In some embodiments, the retinal cell is a cone cell. In some embodiments, the retinal cell is a bipolar cell. In some embodiments, the retinal cell is a RPE cell.

In particular embodiments, the recombinant AAV virion comprising a variant AAV capsid protein described herein is capable of delivering a gene product (such as a therapeutic gene product) to the retina when delivered via intravitreal injection, e.g., wherein the resulting expression is at least 2-fold, at least 3-fold, at least 4-fold, at least 5-fold, at least 10-fold, at least 20-fold, at least 50-fold, or at least 100-fold greater as compared to a corresponding recombinant AAV virion comprising the corresponding parental AAV capsid protein. In particular embodiments, the recombinant AAV virion comprising a variant AAV capsid protein described herein is capable of delivering a gene product to the retina when delivered via intravitreal injection, e.g., wherein the resulting expression is at least 2-fold, at least 3-fold, at least 4-fold, at least 5-fold, at least 10-fold, at least 20-fold, at least 50-fold, or at least 100-fold greater as compared to an AAV5 and/or AAV2.5T vector.

Numerous methods are known in the art for production of recombinant AAV virions, including transfection, stable cell line production, and infectious hybrid virus production systems which include adenovirus-AAV hybrids, herpesvirus-AAV hybrids (Conway, J E et al., (1997) *J. Virology* 71(11):8780-8789) and baculovirus-AAV hybrids. rAAV production cultures for the production of rAAV virus particles all require; 1) suitable host cells, 2) suitable helper virus function, 3) AAV rep and cap genes; 4) a nucleic acid (such as a sequence encoding a gene product) flanked by at least one AAV ITR sequence (e.g., an oversized rAAV vector genome); and 5) suitable media and media components to support rAAV production. In some embodiments, the suitable host cell is a primate host cell. In some embodiments, the suitable host cell is a human-derived cell line such as HeLa, A549, 293, or Perc.6 cells.

In some embodiments, the suitable helper function is provided by wild-type or mutant adenovirus (such as temperature sensitive adenovirus), herpes virus (HSV), baculovirus, or a plasmid construct providing helper functions. In some embodiments, the AAV helper functions are provided by adenovirus or HSV. In some embodiments, the AAV helper functions are provided by baculovirus and the host cell is an insect cell (e.g., *Spodoptera frugiperda* (Sf9) cells).

In some embodiments, the AAV virion described herein was produced in an insect cell. In some embodiments, the AAV virion described herein was produced in a *Spodoptera frugiperda* (Sf9) cell. In some embodiments, the AAV virion described herein was produced in a human-derived cell line. In some embodiments, the AAV virion described herein was produced in a HeLa, A549, 293, or Perc.6 cell. In some embodiments, the AAV virion described herein was produced in a HEK-293 cell.

In some embodiments, the AAV rep gene may be from any AAV serotype. In general, but not obligatory, the AAV rep gene is of the same serotype as the ITRs of the rAAV vector genome as long as the rep protein encoded by the rep gene may function to replicate and package the rAAV genome.

Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors.

One method for producing rAAV virions is the triple transfection method. Briefly, a plasmid containing a rep gene and a capsid gene, such as a polynucleotide encoding a variant AAV capsid protein disclosed herein, along with a helper adenoviral plasmid, may be transfected (e.g., using the calcium phosphate method) into a cell line (e.g., HEK-293 cells), and virions may be collected and optionally purified. As such, in some embodiments, the rAAV virion was produced by triple transfection of a vector genome, a nucleic acid encoding AAV rep and a cap, such as a polynucleotide encoding a variant capsid protein disclosed herein, and a nucleic acid encoding AAV helper functions into a host cell, wherein the transfection of the nucleic acids to the host cells generates a host cell capable of producing rAAV virions.

In some embodiments, rAAV virions may be produced by a producer cell line method, such as the exemplary producer cell line method described in Martin et al., (2013) *Human Gene Therapy Methods* 24:253-269; U.S. Pub. No. US2004/0224411; and Liu, X. L. et al. (1999) Gene Ther. 6:293-299). Briefly, a cell line (e.g., a HeLa, 293, A549, or Perc.6 cell line) may be stably transfected with a plasmid containing a rep gene, a capsid gene, such as a polynucleotide encoding a variant capsid protein disclosed herein, and a vector genome. Cell lines may be screened to select a lead clone for rAAV production, which may then be expanded to a production bioreactor and infected with a helper virus (e.g., an adenovirus or HSV) to initiate rAAV production. Virions may subsequently be harvested, adenovirus may be inactivated (e.g., by heat) and/or removed, and the rAAV virions may be purified. As such, in some embodiments, the rAAV virion was produced by a producer cell line comprising one or more of a nucleic acid encoding the rAAV genome, a nucleic acid encoding AAV rep, a polynucleotide encoding a variant capsid protein disclosed herein, and a nucleic acid encoding AAV helper functions.

In some embodiments, the nucleic acid encoding the AAV rep gene, the AAV cap gene, and/or the rAAV genome are stably maintained in the producer cell line. In some embodiments, the nucleic acid encoding the AAV rep gene, the AAV cap gene, and/or the rAAV genome is introduced on one or more plasmids into a cell line to generate a producer cell line. In some embodiments, the AAV rep gene, the AAV cap gene, and rAAV genome are introduced into a cell on the same plasmid. In other embodiments, the AAV rep, the AAV cap, and rAAV genome are introduced into a cell on two or more different plasmids. In some embodiments, a cell line stably transfected with a plasmid maintains the plasmid for multiple passages of the cell line (e.g., 5, 10, 20, 30, 40, 50 or more than 50 passages of the cell line). For example, the plasmid(s) may replicate as the cell replicates, or the plasmid(s) may integrate into the cell genome. A variety of sequences that enable a plasmid to replicate autonomously in a cell (e.g., a human cell) have been identified (see, e.g., Krysan, P. J. et al. (1989) *Mol. Cell Biol.* 9:1026-1033). In some embodiments, the plasmid(s) may contain a selectable marker (e.g., an antibiotic resistance marker) that allows for selection of cells maintaining the plasmid. Selectable markers commonly used in mammalian cells include without limitation blasticidin, G418, hygromycin B, zeocin, puromycin, and derivatives thereof. Methods for introducing nucleic acids into a cell are known in the art and include without limitation viral transduction, cationic transfection (e.g., using a cationic polymer such as DEAE-dextran or a cationic lipid such as lipofectamine), calcium phosphate transfection, microinjection, particle bombardment, electroporation, and nanoparticle transfection (for more details, see, e.g., Kim, T. K. and Eberwine, J. H. (2010) *Anal. Bioanal. Chem.* 397:3173-3178).

In some embodiments, the nucleic acids encoding the AAV rep gene, the AAV cap gene, and/or the rAAV genome are stably integrated into the genome of the producer cell line. In some embodiments, the nucleic acids encoding the AAV rep gene, the AAV cap gene, and/or the rAAV genome are introduced on one or more plasmids into a cell line to generate a producer cell line. In some embodiments, the AAV rep gene, the AAV cap gene, and the rAAV genome are introduced into a cell on the same plasmid. In other embodiments, the AAV rep gene, the AAV cap gene, and the rAAV genome are introduced into a cell on two or more different plasmids. In some embodiments, the plasmid(s) may contain a selectable marker (e.g., an antibiotic resistance marker) that allows for selection of cells maintaining the plasmid. Methods for stable integration of nucleic acids into a variety of host cell lines are known. For example, repeated selection (e.g., through use of a selectable marker) may be used to select for cells that have integrated a nucleic acid containing a selectable marker (and the AAV cap gene, the AAV rep gene, and/or a rAAV genome). In other embodiments, nucleic acids may be integrated in a site-specific manner into a cell line to generate a producer cell line. Several site-specific recombination systems are known in the art, such as FLP/FRT (see, e.g., O'Gorman, S. et al. (1991) *Science* 251:1351-1355), Cre/loxP (see, e.g., Sauer, B. and Henderson, N. (1988) *Proc. Natl. Acad. Sci.* 85:5166-5170), and phi C31-att (see, e.g., Groth, A. C. et al. (2000) *Proc. Natl. Acad. Sci.* 97:5995-6000).

In some embodiments, the producer cell line is derived from a primate cell line (e.g., a non-human primate cell line, such as a Vero or FRhL-2 cell line). In some embodiments, the cell line is derived from a human cell line. In some embodiments, the producer cell line is derived from HeLa, 293, A549, or PERC.6® (Crucell) cells. For example, prior to introduction and/or stable maintenance/integration of nucleic acids encoding the AAV rep gene, the AAV cap gene, and/or the rAAV genome into a cell line to generate a producer cell line, the cell line is a HeLa, 293, A549, or PERC.6® (Crucell) cell line, or a derivative thereof.

In some embodiments, the producer cell line is adapted for growth in suspension. As is known, anchorage-dependent cells are typically not able to grow in suspension without a substrate, such as microcarrier beads. Adapting a cell line to grow in suspension may include, for example, growing the cell line in a spinner culture with a stirring paddle, using a culture medium that lacks calcium and magnesium ions to prevent clumping (and optionally an antifoaming agent), using a culture vessel coated with a siliconizing compound, and selecting cells in the culture (rather than in large clumps or on the sides of the vessel) at each passage. For further description, see, e.g., ATCC frequently asked questions document (available at www[dot]atcc[dot]org/Global/FAQs/9/1/Adapting %20a %20monolayer%20cell%20line %20to%20s uspension-40 [dot]aspx) and references cited therein.

In some aspects, a method is provided for producing a rAAV virion as disclosed herein comprising (a) culturing a host cell under a condition that rAAV virions are produced, wherein the host cell comprises (i) a polynucleotide encoding a variant AAV capsid protein disclosed herein; (ii) a polynucleotide encoding a rep protein; (iii) a polynucleotide cassette comprising a sequence that encodes a gene product, e.g., a therapeutic gene product flanked by at least one AAV ITR; and (iv) AAV helper functions; and (b) recovering the rAAV virion produced by the host cell. In some embodiments, said at least one AAV ITR is selected from the group consisting of AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV serotype ITRs or the like. In some embodiments, the method further comprises purifying the rAAV virion.

Suitable rAAV production culture media of the present invention may be supplemented with serum or serum-derived recombinant proteins at a level of 0.5%-20% (v/v or w/v). Alternatively, as is known in the art, rAAV virions may be produced in serum-free conditions which may also be referred to as media with no animal-derived products. One of ordinary skill in the art may appreciate that commercial or custom media designed to support production of rAAV virions may also be supplemented with one or more cell culture components know in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV production cultures may also include suspension-adapted host cells such as HeLa, 293, and SF-9 cells which can be cultured in a variety of ways including, for example, spinner flasks, stirred tank bioreactors, and disposable systems such as the Wave bag system.

V. Compositions

Also provided herein are compositions comprising a recombinant AAV virion disclosed herein comprising a variant AAV capsid protein described herein. In some embodiments, the composition is a pharmaceutical composition comprising a recombinant AAV virion disclosed herein and one or more pharmaceutically acceptable diluent, carrier, or excipient.

The recombinant AAV virion can be combined with pharmaceutically-acceptable carriers, diluents and reagents useful in preparing a formulation that is generally safe, non-toxic, and desirable, and includes excipients that are acceptable for primate use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfate; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide. In particular embodiments, the pharmaceutical compositions are sterile. For instances in which ocular cells are to be contacted in vivo, the recombinant AAV virion can be treated as appropriate for delivery to the eye.

Pharmaceutical compositions may further include sterile aqueous solutions or dispersions and sterile powders for the extemporaneous preparation of sterile injectable solutions or dispersion. For intravenous administration, suitable carriers include, but are not limited to, physiological saline, bacteriostatic water, or phosphate buffered saline (PBS). In some cases, the composition is sterile and should be fluid to the extent that easy syringability exists. In certain embodiments, the pharmaceutical composition is stable under the conditions of manufacture and storage and is preserved against the contaminating action of microorganisms such as bacteria and fungi. The carrier can be, e.g., a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In some embodiments, the pharmaceutical composition comprises one or more isotonic agents, for example, a sugar, a polyalcohol such as mannitol or sorbitol, and sodium chloride. In some embodiments, the pharmaceutical composition comprises an agent which delays absorption, for example, aluminum monostearate and gelatin.

Sterile solutions can be prepared by incorporating the recombinant AAV virion in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation include, but are not limited to, vacuum drying and freeze-drying that yields a powder of the active ingredient plus any additional desired ingredient from a previously sterile-filtered solution thereof.

In some embodiments, the pharmaceutical composition is prepared with a carrier that will protect the viral vector against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Liposomal suspensions (including liposomes targeted to infected cells with monoclonal antibodies to viral antigens) can also be used as pharmaceutically acceptable carriers, for example, as described in U.S. Pat. No. 4,522,811.

It may be advantageous to formulate oral, ocular or parenteral compositions in dosage unit form for ease of administration and uniformity of dosage. Dosage unit form as used herein may refer to physically discrete units suited as unitary dosages for the subject to be treated; each unit containing a predetermined quantity of active compound calculated to produce the desired therapeutic effect.

Any concentration of recombinant AAV virions suitable to effectively transduce mammalian cells can be prepared. For example, the recombinant AAV virion may be formulated at a concentration of about $10^8$ vector genomes per mL or more, for example, about $5\times10^8$ vector genomes per mL; about $10^9$ vector genomes per mL; about $5\times10^9$ vector genomes per mL, about $10^{10}$ vector genomes per mL, about $5\times10^{10}$ vector genomes per mL; about $10^{11}$ vector genomes per mL; about $5\times10^{11}$ vector genomes per mL; about $10^{12}$ vector genomes per mL; about $5\times10^{12}$ vector genomes per mL; about $10^{13}$ vector genomes per mL; about $1.5\times10^{13}$ vector genomes per mL; about $3\times10^{13}$ vector genomes per mL; about $5\times10^{13}$ vector genomes per mL; about $7.5\times10^{13}$ vector genomes per mL; about $9\times10^{13}$ vector genomes per mL; about $1\times10^{14}$ vector genomes per mL, or about $5\times10^{14}$ vector genomes per mL; or more. In some embodiments the viral particles may be formulated at a concentration of no more than about $1\times10^{15}$ vector genomes per mL.

The recombinant AAV virion may be formulated into any suitable unit dosage, including, without limitation, about $1\times10^8$ vector genomes or more, for example, about $1\times10^9$, about $1\times10^{10}$, about $1\times10^{11}$, about $1\times10^{12}$, or about $1\times10^{13}$ vector genomes or more, or in certain instances, about $1\times10^{14}$ vector genomes. In some embodiments, the recombinant AAV virion may be formulated into any suitable unit dosage no more than about $4\times10^{15}$ vector genomes. In some cases, the unit dosage is at most about $5\times10^{15}$ vector genomes, e.g. about $1\times10^{14}$ vector genomes or less, for example about $1\times10^{13}$, about $1\times10^{12}$, about $1\times10^{11}$, about $1\times10^{10}$, or about $1\times10^9$ vector genomes or less, or in certain instances about $1\times10^8$ vector genomes or less. In some embodiments, the recombinant AAV virion may be formulated into any suitable unit dosage no less than about $1\times10^8$ vector genomes. In some cases, the unit dosage is about $1\times10^{10}$ to about $1\times10^{11}$ vector genomes. In some cases, the unit dosage is about $1\times10^{10}$ to about $3\times10^{12}$ vector genomes. In some cases, the unit dosage is about $1\times10^9$ to about $3\times10^{13}$ vector genomes. In some cases, the unit dosage is about $1\times10^8$ to about $3\times10^{14}$ vector genomes.

In some cases, the unit dosage of a pharmaceutical composition may be measured using multiplicity of infection (MOI). By MOI it is meant the ratio, or multiple, of viral genomes to the cells to which the nucleic acid may be delivered. In some cases, the MOI may be about $1\times10^6$. In some cases, the MOI may be about $1\times10^5$-about $1\times10^7$. In some cases, the MOI may be about $1\times10^4$-about $1\times10^8$. In some cases, recombinant virions of the disclosure are at least at about any of $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI. In some cases, recombinant AAV virions of this disclosure are at about $1\times10^8$ to about $3\times10^{14}$ MOI. In some cases, recombinant AAV virions of the disclosure are at most at about any of $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI.

In some aspects, the amount of pharmaceutical composition comprises about $1\times10^8$ to about $1\times10^{15}$ recombinant AAV virions, about $1\times10^9$ to about $1\times10^{14}$ recombinant AAV virions, about $1\times10^{10}$ to about $1\times10^{13}$ recombinant AAV virions, or about $1\times10^{11}$ to about $3\times10^{12}$ recombinant AAV virions.

The pharmaceutical compositions can be included in a container, pack, or dispenser, e.g. syringe, e.g. a prefilled syringe, together with instructions for administration.

In some embodiments, the pharmaceutical composition comprises a pharmaceutically acceptable salt. A variety of pharmaceutically acceptable salts are known in the art and described, e.g., in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see Handbook of Pharmaceutical Salts: Properties, Selection, and Use by Stahl and Wermuth (Wiley-VCH, 2002).

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. Pharma Sci., 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

The pharmaceutical compositions can be formulated for administration to mammals, such as primates, such as humans. In some embodiments, the pharmaceutical composition comprises an aqueous carrier, such as nontoxic, inert, pharmaceutically acceptable aqueous carriers. In some embodiments, the pH of the aqueous carrier is about 3 to about 8. In some embodiments, the pH of the aqueous carrier is about 6 to about 8.

In some embodiments, the pharmaceutical compositions provided herein comprise a therapeutically effective amount of a recombinant AAV virion disclosed herein in admixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. In some embodiments, the pharmaceutical composition is stable for at least six months at about 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467.

Also provided herein are compositions comprising a recombinant AAV virion disclosed herein comprising a variant AAV capsid protein described herein for use in a method described herein. In some embodiments, the composition is a pharmaceutical composition comprising a recombinant AAV virion disclosed herein and one or more pharmaceutically acceptable diluent, carrier, or excipient.

Also provided herein are compositions comprising a polynucleotide described herein encoding a variant AAV capsid protein described herein. In some embodiments, the composition is for use in a method disclosed herein, such as a method of making a recombinant AAV virion comprising a variant AAV capsid protein.

VI. Methods and Uses

As disclosed in the accompanying Examples, modified capsid proteins described herein can confer enhanced or altered cellular tropism to recombinant AAV virion comprising the variant AAV capsid protein. For example, certain variant AAV capsid proteins described herein are associated with increased infectivity of the retina or increased expression levels of gene product in the retina, increased binding to the ILM, increased infectivity of retina cells following intravitreal injection, and/or increased expression of gene product in the retina following intravitreal injection.

Examples of retinal cell components that may be transfected by virions described herein can include, but are not limited to, astrocytes, Müllner Cells, RGC, RGC axons, photoreceptors, bipolar cells, amacrine cells, horizontal cells, and combinations thereof. In some instances, cell markers are used to measure transduction of a nucleic acid encoding a gene product into a retinal cell component. Cell markers can include, but are not limited to, GFAP, Vimentin, Fox, β-tubulin, rhodopsin, PKCa, parvalbumin, calbindin and combinations thereof. Table 1 below depicts exemplary cell markers and a corresponding retinal cell component.

TABLE 1

Summary of cell markers and cell types

| Marker | Cell Type |
| --- | --- |
| GFAP | Astrocytes |
| Vimentin | Müllner Cells |
| Fox | RGC |
| β-tubulin | RGC axons |
| Rhodopsin (Rho) | Rod photoreceptors |
| PKCa | Bipolar cells |
| Parvalbumin | Amacrine cells |
| Calbindin | Horizontal cells |

In some instances, the ability of a rAAV virion to transduce a gene product can be measured by the expression of a reporter protein. In some embodiments, the reporter protein can include GFP, YFP, red cherry, β-galactosidase, or other reporter proteins known in the art.

In some instances, the expression of the reporter protein over time can be determined through a capture of an image of an eye at various time points. For example, the expression of GFP can be correlated to an increase in fluorescence. The amount of fluorescence at a given time point can be used to quantitate expression of a gene product.

In some embodiments, immunofluorescence can be used to determine localization of a transduced gene in a retinal cell compartment described herein. The retinal cell compartment can be labeled by use of an antibody specific for a cell marker disclosed herein. In some instances, the antibody is coupled to a fluorophore. In some instances, a secondary antibody can be used to detect binding of the first antibody. The transduced retina can be cryosectioned prior to incubation with an antibody against the cell marker of interest, thereby allowing imaging of the bound antibody. The cryosection can then be labeled using antibodies to detect the transduction of a transgene, the presence of a cell maker of interest, and regions of overlap between the two.

Accordingly, provided herein are methods of enhancing or altering the tropism of a recombinant AAV virion, the method comprising incorporating a variant AAV capsid protein disclosed herein into a recombinant AAV virion. Also provided herein are methods of enhancing or altering the tropism of a recombinant AAV virion, the method comprising substituting amino acid residues 570-579 of a parental AAV capsid with an amino acid sequence comprising HKFKSGD (SEQ ID NO: 1) to generate a variant AAV capsid protein, and incorporating the variant AAV capsid protein into a recombinant AAV virion, wherein the amino acid residue numbering corresponds to an AAV5 VP1 capsid protein. In some embodiments, the method comprises substituting amino acid residues 570-579 with an amino acid sequence comprising $X_1X_2HKFKSGDX_3$ (SEQ ID NO: 2), wherein $X_{1-3}$ can independently be any amino acid. In some embodiments, each of $X_{1-3}$ is independently selected from A, L, G, S, and T. In some embodiments, $X_1$ is L. In some embodiments, $X_2$ is A. In some embodiments, $X_3$ is A. In some embodiments, the method comprises substituting amino acid residues 570-579 with an amino acid sequence comprising LAHKFKSGDA (SEQ ID NO: 3); having at least 80% or at least 90% homology with SEQ ID NO: 3; having at least 80% or at least 90% sequence identity with SEQ ID NO: 3; or having four or more, five or more, six or more, seven or more, eight or more, or nine or more consecutive amino acids within SEQ ID NO: 3. In some embodiments, the amino acid sequence comprises LAHKFKSGDA (SEQ ID NO: 3).

In some embodiments, the parental AAV capsid protein is a wild-type AAV capsid protein, for example an AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), avian AAV, bovine AAV, canine AAV, equine AAV, primate AAV, non-primate AAV, or ovine AAV capsid protein. In some embodiments, the parental AAV capsid protein is an AAV5 capsid protein. In some embodiments, the parental AAV capsid protein is a VP1, VP2, or VP3 capsid protein. In some embodiments, the parental AAV capsid protein is an AAV5 VP1 capsid protein.

In some embodiments, the parental AAV capsid protein is a variant AAV capsid protein. In some embodiments, the parental AAV capsid protein is a variant of an AAV1, an AAV2, an AAV3, an AAV4, an AAV5, an AAV6, an AAV7, an AAV8, an AAV9, an AAV10, an avian AAV, a bovine AAV, a canine AAV, an equine AAV, a primate AAV, a non-primate AAV, or an ovine AAV capsid protein. In some embodiments, the parental AAV capsid protein is a variant of an AAV5 VP1 capsid protein. In some embodiments, the parental AAV capsid protein is a variant of an AAV5 VP1 capsid protein having at least 90%, at least 95%, at least 98%, or at least 99% homology to SEQ ID NO: 4. In some embodiments, the parental AAV capsid protein is a variant of an AAV5 VP1 capsid protein having at least 90%, at least 95%, at least 98%, or at least 99% sequence identity to SEQ ID NO: 4. In some embodiments, the parental AAV capsid protein is a hybrid. In some embodiments, the parental AAV capsid protein is a hybrid of AAV2 and AAV5. In some embodiments, the parental AAV capsid protein is an AAV 2.5T, or a variant thereof having at least 90%, at least 95%, at least 98%, or at least 99% homology to an AAV2.5T capsid protein. In some embodiments, the parental AAV capsid protein is AAV 2.5T, or a variant thereof having at least 90%, at least 95%, at least 98%, or at least 99% sequence identity to an AAV2.5T capsid protein. In some embodiments, the parental AAV capsid protein is AAV 2.5T. In some embodiments, the parental AAV capsid protein is a VP1, VP2, or VP3 capsid protein. In some embodiments, the parental AAV capsid protein is an AAV2.5T VP1 capsid protein, or a variant thereof having at least 90%, at least 95%, at least 98%, or at least 99% homology to an AAV2.5T VP1 capsid protein (SEQ ID NO: 5). In some embodiments, the parental AAV capsid protein is an AAV2.5T VP1 capsid protein, or a variant thereof having at least 90%, at least 95%, at least 98%, or at least 99% sequence identity to an AAV2.5T VP1 capsid protein (SEQ ID NO: 5).

Recombinant AAV virions described herein, comprising a variant AAV capsid protein described herein, may be used in delivering a gene product to a cell, e.g., a cell of an animal. For example, they may be used in research, e.g., to determine the effect that the gene product has on cell viability and/or function. As another example, they may be used in medicine, e.g. to treat a disorder, for example, by delivering a therapeutic gene product to a cell or tissue. Thus, in some embodiments, provided herein are methods of expressing a gene product in a cell, the method comprising contacting a cell with a composition comprising a recombinant AAV virion comprising a variant AAV capsid protein disclosed herein and a polynucleotide cassette comprising a sequence that encodes the gene product. In some embodiments, contacting occurs in vitro. In some embodiments, contacting occurs in vivo, i.e., the composition is administered to a subject. In particular embodiments, the composition is administered parenterally, e.g., intravenously, orally, or by injection. In certain embodiments, the composition is administered to the eye by injection, e.g., administered to the retina, sub-retina or vitreous. In certain embodiments, the composition is administered by retinal injection, sub-retinal injection, or intravitreal injection. In certain embodiments, the composition is administered by intravitreal injection.

In particular embodiments in which a mammalian cell is to be contacted in vitro with a recombinant AAV virion comprising a variant AAV capsid protein disclosed herein, the cell may be from any mammalian species, e.g., rodent (e.g., mice, rats, gerbils, squirrels), rabbit, feline, canine, goat, ovine, pig, equine, bovine, primate, human. The cell may be from an established cell line, e.g., WERI cell, 661W cell, or the cell may be a primary cell.

In certain embodiments, to promote expression of the gene product, the cell is contacted with the recombinant AAV virion for about 30 minutes to about 24 hours or more, e.g., about any one of 1 hour, 1.5 hours, 2 hours, 2.5 hours, 3 hours, 3.5 hours, 4 hours, 5 hours, 6 hours, 7 hours, 8 hours, 12 hours, 16 hours, 18 hours, 20 hours, or 24 hours, etc. The cell may be contacted with the recombinant AAV virion one or more times, e.g., one time, twice, three times, or more than three times, and the cell is allowed to incubate with the recombinant AAV virion for some amount of time following each contacting event e.g., about 16-24 hours. Contacting the cell may occur in any culture media and under any culture conditions that promote the survival of the cell. For example, a cell may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g., penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

In certain embodiments, an effective amount of a recombinant AAV virion comprising a variant AAV capsid protein is provided to produce the expression of the gene product in cells. In particular embodiments, the effective amount may be determined empirically, e.g., by detecting the presence or levels of the gene product, by detecting an effect on the viability or function of the cells, etc. In certain embodiments, an effective amount of the recombinant AAV virion promotes equal or greater expression of the gene product in a cell than the same amount of a reference viral vector, such as a recombinant AAV virion comprising the parental AAV capsid protein. In certain embodiments, expression is enhanced about 2-fold or more relative to the expression from a reference viral vector; for example, about any of 3-fold, 4-fold, or 5-fold or more, in some instances about any of 10-fold, 20-fold or 50-fold or more, e.g. 100-fold. In certain embodiments, the enhanced expression occurs in a particular cell type, e.g., any of the ocular cells described herein.

For instances in which cells are contacted in vivo with a composition comprising a recombinant AAV virion comprising a variant AAV capsid protein disclosed herein and a polynucleotide cassette comprising a sequence that encodes the gene product, the subject may be any mammal, e.g., rodent (e.g., mice, rats, gerbils), rabbit, feline, canine, goat, ovine, pig, equine, bovine, or primate (e.g., human, or non-human primate). The methods and compositions of the present disclosure find use in the treatment of any condition that can be addressed, at least in part, by gene therapy of cells. Thus, the compositions and methods of the present disclosure find use in the treatment of individuals in need of a cell therapy. Cells include but are not limited to blood, eye, liver, kidney, heart, muscle, stomach, intestine, pancreas, and skin.

Also provided herein are methods of delivering a gene product to the retina comprising administering by intravitreal injection a recombinant AAV virion comprising a variant AAV capsid protein disclosed herein and a polynucleotide cassette comprising a sequence that encodes a gene product. In some embodiments, provided herein are methods of delivering a gene product across the ILM comprising administering by intravitreal injection a recombinant AAV virion comprising a variant AAV capsid protein disclosed herein and a polynucleotide cassette comprising a sequence that encodes a gene product. In certain embodiments, the disclosure provides a method of providing a gene product to a retina of a subject, comprising administering to the subject by intravitreal injection a pharmaceutical composition comprising a recombinant AAV virion described herein, wherein the recombinant AAV virion comprises a variant AAV capsid provided or disclosed herein and a polynucleotide sequence that encodes the gene product.

In particular embodiments, the subject has been diagnosed with or is suspected of having one or more diseases or disorders selected from the group consisting of: acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; diabetic retinal ischemia; ischemic retinopathy non-retinopathy; diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; and disorders of color vision, including achromatopsia, protanopia, deuteranopia, and tritanopia.

In particular embodiments, the subject is at risk of developing one or more diseases or disorders selected from the group consisting of: acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; diabetic retinal ischemia; ischemic retinopathy non-retinopathy; diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; and disorders of color vision, including achromatopsia, protanopia, deuteranopia, and tritanopia.

Also provided herein are methods of treating a disease or disorder of the retina of a subject in need thereof comprising administering by intravitreal injection a recombinant AAV virion comprising a variant AAV capsid protein disclosed herein and a polynucleotide cassette comprising a sequence that encodes a therapeutic gene product. Also provided herein are methods of prophylactically treating a disease or disorder of the retina of a subject in need thereof comprising administering by intravitreal injection a recombinant AAV virion comprising a variant AAV capsid protein disclosed herein and a polynucleotide cassette comprising a sequence that encodes a therapeutic gene product. Also provided herein are methods of treating an established or diagnosed disease or disorder of the retina of a subject in need thereof comprising administering by intravitreal injection a recombinant AAV virion comprising a variant AAV capsid protein disclosed herein and a polynucleotide cassette comprising a sequence that encodes a therapeutic gene product. In some embodiments, the method comprises administering a pharmaceutical composition comprising a recombinant AAV virion comprising a variant AAV capsid protein disclosed herein and a polynucleotide cassette comprising a sequence that encodes a therapeutic gene product.

In some embodiments, the disease or disorder is selected from the group consisting of: acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; diabetic retinal ischemia; ischemic retinopathy non-retinopathy; diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; and disorders of color vision, including achromatopsia, protanopia, deuteranopia, and tritanopia.

In particular embodiments, the subject is at risk of developing one or more diseases or disorders selected from the group consisting of: acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; diabetic retinal ischemia; ischemic retinopathy non-retinopathy; diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; and disorders of color vision, including achromatopsia, protanopia, deuteranopia, and tritanopia.

In certain embodiments, the gene product inhibits neovascularization, e.g., choroidal neovascularization (CNV), in the retina of the subject. It has been found that many cellular factors play important roles in regulation in CNV generation, among which may include but are not limited to vascular endothelial growth factor (VEGF), VEGF receptor (VEGFR), platelet-derived growth factor (PDGF), hypoxia inducible factor (HIF), angiopoietin (Ang) and other cytokines, and mitogen-activated protein kinases (MAPK). In some embodiments, the gene product is an inhibitor of one or more of VEGF, VEGFR, PDGF, HIF, Ang, and MAPK.

In some embodiments, the gene product is a gene product or therapeutic gene product disclosed herein. In some embodiments, the gene product is an interfering RNA, an aptamer, or a protein. In some embodiments, the therapeutic gene product is an interfering RNA, an aptamer, or a protein.

In some embodiments, the gene product (or therapeutic gene product) is a siRNA, a miRNA, or a protein. In some embodiments, the gene product (or therapeutic gene product) is a site-specific nuclease that provides for site-specific knock-down of gene function. In some embodiments, the gene product (or therapeutic gene product) is an interfering RNA. In some embodiments, the gene product (or therapeutic gene product) is a siRNA or miRNA.

In some embodiments, the method results in a therapeutic benefit, e.g., preventing the development of a disease or disorder, halting the progression of a disease or disorder, reversing the progression of a disease or disorder, etc. In some embodiments, the method comprises the step of detecting that a therapeutic benefit has been achieved.

In some instances, the expression of the gene product, e.g., as detected by measuring levels of gene product, by measuring therapeutic efficacy, etc., may be observed two months or less after administration, e.g., about 4, 3 or 2 weeks or less after administration, for example, 1 week after administration of the subject composition. Expression of the gene product is also expected to persist over time. Accordingly, in some instances, the expression of the gene product, e.g., as detected by measuring levels of gene product, by measuring therapeutic efficacy, etc., may be observed about 2 months or more after administration of the subject composition, e.g., about 4, 6, 8, or 10 months or more, in some instances about 1 year or more, for example 2, 3, 4, or 5 years, in certain instances, more than 5 years.

In particular embodiments, a subject is administered to one eye or to each of both eyes about $1\times10^8$ vector genomes or more, in some cases about any of $1\times10^9$, $1\times10^{10}$, $1\times10^{11}$, $1\times10^{12}$, or $1\times10^{13}$ vector genomes or more, in certain instances, about $1\times10^{14}$ vector genomes or more. In some cases, the amount of vector genomes that is delivered is at most about $1\times10^{15}$ vector genomes, e.g., $1\times10^{14}$ vector genomes or less, for example about any of $1\times10^{13}$, $1\times10^{12}$, $1\times10^{11}$, $1\times10^{10}$, or $1\times10^9$ vector genomes or less, in certain instances $1\times10^8$ vector genomes, and sometimes no less than $1\times10^8$ vector genomes. In some cases, the amount of vector genomes that is delivered is about $1\times10^{10}$ to about $1\times10^{11}$ vector genomes. In some cases, the amount of vector genomes that is delivered is about $1\times10^{10}$ to about $3\times10^{12}$ vector genomes. In some cases, the amount of vector genomes that is delivered is about $1\times10^9$ to about $3\times10^{13}$ vector genomes. In some cases, the amount of vector genomes that is delivered is about $1\times10^8$ to about $3\times10^{14}$ vector genomes.

In some cases, the amount of pharmaceutical composition to be administered may be measured using multiplicity of infection (MOI). In some cases, MOI may refer to the ratio, or multiple of vector or viral genomes to the cells to which the nucleic may be delivered. In some cases, the MOI may be about $1\times10^6$. In some cases, the MOI may be about $1\times10^5$-about $1\times10^7$. In some cases, the MOI may be about $1\times10^4$-about $1\times10^8$. In some cases, recombinant AAV virions of the disclosure are at least at about any of $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, or $1\times10^{18}$ MOI. In some cases, recombinant AAV virions of this disclosure are at about $1\times10^8$ to about $3\times10^{14}$ MOI. In some cases, recombinant AAV virions of the disclosure are at most at about any of $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, or $1\times10^{18}$ MOI.

In some aspects, the amount of pharmaceutical composition comprises about $1\times10^8$ to about $1\times10^{15}$ particles of recombinant AAV virions, about $1\times10^9$ to about $1\times10^{14}$ particles of recombinant AAV virions, about $1\times10^{10}$ to about $1\times10^{15}$ particles of recombinant AAV virions, or about $1\times10^{11}$ to about $3\times10^{12}$ particles of recombinant AAV virions.

In some embodiments, more than one administration (e.g., two, three, four, or more administrations) may be employed to achieve the desired level of gene expression over a period of various intervals, e.g., daily, weekly, monthly, yearly, etc.

In some aspects, no recombinant AAV virion is detected in the human subject's tear, blood, saliva or urine samples about 7, about 14, about 21 or about 30 days after administering said pharmaceutical composition. In some aspects, the presence or absence of the recombinant AAV virion is detected by qPCR or ELBA.

In some aspects, a subject's best corrected visual acuity (BCVA) improves by about 1, 2 3, 4, 5 or more lines following a method of treatment described herein.

In some aspects, a reduction in neovascularization as assessed by Fluorescein Angiography (FA) follows the administering step.

In some cases, retinal thickness may be measured to examine the effects of treatment. In some cases, the central retinal thickness of the human subject does not increase by more than about 50 microns, about 100 microns, or about 250 microns within about 12 months following treatment with the pharmaceutical composition of the disclosure. In some cases, the central retinal thickness of the human subject decreases by at least about 50 microns, about 100 microns, about 200 microns, about 250 microns, about 300 microns, about 400 microns, about 500 microns, or about 600 microns within about 3 months, about 6 months, about 9 months, or about 12 months following treatment with the pharmaceutical composition of the disclosure. The decrease in the central retinal thickness of the human subject may be measured comparing the central retinal thickness at one or more points in time to a baseline measurement taken at or within about 1, 3, 7 or 10 days of the administration of the pharmaceutical composition of the disclosure.

From the foregoing it will be appreciated that, although specific embodiments of the invention have been described herein for purposes of illustration, various modifications may be made without deviating from the spirit and scope of the invention. Accordingly, the invention is not limited except as by the appended claims.

VII. Exemplary Embodiments

Among the provided embodiments are:

1. A recombinant adeno-associated virus (AAV) virion comprising:
(a) a variant AAV capsid protein comprising a modified sequence comprising one or more amino acid substitutions within amino acid residues 570-579 relative to a parental AAV capsid protein, wherein the modified sequence comprises HKFKSGD (SEQ ID NO: 1), and wherein the amino acid residue numbering corresponds to an AAV5 VP1 capsid protein; and
(b) a polynucleotide sequence encoding a therapeutic gene product.

2. The recombinant AAV virion of embodiment 1, wherein the parental AAV capsid protein is an AAV5 capsid protein or an AAV5 and AAV2 hybrid capsid protein.

3. The recombinant AAV virion of embodiment 1 or 2, wherein the parental AAV capsid protein is an AAV2.5T capsid protein.

4. The recombinant AAV virion of any one of embodiments 1-3, wherein the parental AAV capsid protein is an AAV2.5T VP1 capsid protein.

5. The recombinant AAV virion of any one of embodiments 1-4, wherein the modified sequence comprises LAHKFKSGDA (SEQ ID NO: 3).

6. The recombinant AAV virion of any one of embodiments 1-5, wherein the variant AAV capsid protein comprises a capsid sequence having at least 85% homology to the amino acid sequence set forth in SEQ ID NO: 4 or SEQ ID NO:5.

7. The recombinant AAV virion of any one of embodiments 1-6, wherein the variant AAV capsid protein comprises a capsid sequence set forth in SEQ ID NO:6 or SEQ ID NO:7.

8. The recombinant AAV virion of any one of embodiments 1-7, wherein the rAAV virion is a variant AAV5 or a variant AAV2 and AAV5 hybrid virion.

9. The recombinant AAV virion of any one of embodiments 1-8, wherein the rAAV virion is a variant AAV2.5T virion.

10. The recombinant AAV virion of any one of embodiments 1-9, wherein the recombinant AAV virion is capable of transducing cells of the retina when intravitreally injected into a mammal.

11. The recombinant AAV virion of embodiment 10, wherein the recombinant AAV virion is capable of transducing one or more of: a photoreceptor, a retinal ganglion cell, a Müller cell, a bipolar cell, an amacrine cell, a horizontal cell, and a retinal pigment epithelium cell when intravitreally injected into a mammal.

12. The recombinant AAV virion of embodiment 10 or 11, wherein the recombinant AAV virion is capable of transducing retinal pigment epithelium cells when intravitreally injected into a mammal.

13. The recombinant AAV virion of any one of embodiments 1-12, wherein the therapeutic gene product is a siRNA, a miRNA, or a protein.

14. The recombinant AAV virion of any one of embodiments 1-13, wherein the therapeutic gene product is an anti-vascular endothelial growth factor (anti-VEGF) gene product.

15. The recombinant AAV virion of any one of embodiments 1-13, wherein the therapeutic gene product is an opsin.

16. The recombinant AAV virion of any one of embodiments 1-15, wherein the polynucleotide encoding the therapeutic gene product is flanked by one or more AAV ITRs.

17. The recombinant AAV virion of embodiment 16, wherein the one or more AAV ITRs are AAV1, AAV2, AAV3, AAV4, AAV5, AAV6, AAV7, AAV5, AAV5, AAV10, avian AAV, bovine AAV, canine AAV, equine AAV, primate AAV, non-primate AAV, or ovine AAV ITRs or variants thereof.

18. The recombinant AAV virion of embodiment 16 or 17, wherein the one or more AAV ITRs are AAV2 ITRs or AAV5 ITRs.

19. The recombinant AAV virion of any one of embodiments 1-18, wherein the recombinant AAV virion has an altered cellular tropism as compared to AAV2.5T.

20. A pharmaceutical composition comprising the recombinant AAV virion of any one of embodiments 1-19.

21. A method for producing a rAAV virion comprising:
(a) culturing a host cell under a condition that rAAV virions are produced, wherein the host cell comprises:
(i) a polynucleotide encoding a variant AAV capsid protein comprising a modified sequence comprising one or more amino acid substitutions within amino acid residues 570-579 relative to a parental AAV capsid protein, wherein the modified sequence comprises HKFKSGD (SEQ ID NO: 1);
    (ii) a polynucleotide encoding a rep protein;
    (iii) a polynucleotide cassette comprising a sequence that encodes a therapeutic gene product flanked by at least one AAV ITR; and
    (iv) AAV helper functions; and
    (b) recovering the rAAV virion produced by the host cell.

22. A method of providing a therapeutic gene product to a retina of a subject, comprising administering to the subject by intravitreal injection the recombinant AAV virion of any one of embodiments 1-19 or the pharmaceutical composition of embodiment 20.

23. The method of embodiment 22, wherein the subject has been diagnosed with or is suspected of having one or more conditions selected from the group consisting of: acute macular neuroretinopathy, Behcet's disease, choroidal neovascularization, diabetic uveitis, histoplasmosis, macular degeneration, edema, multifocal choroiditis, ocular trauma which affects a posterior ocular site or location, ocular tumor, central retinal vein occlusion, diabetic retinopathy, proliferative vitreoretinopathy (PVR), retinal arterial occlusive disease, retinal detachment, uveitic retinal disease, sympathetic ophthalmia, Vogt Koyanagi-Harada (VKH) syndrome, uveal diffusion, a posterior ocular condition caused by or influenced by an ocular laser treatment, posterior ocular conditions caused by or influenced by a photodynamic therapy, photocoagulation, radiation retinopathy, an epiretinal membrane disorder, branch retinal vein occlusion, anterior ischemic optic neuropathy, diabetic retinal ischemia, ischemic retinopathy, non-retinopathy diabetic retinal dysfunction, retinoschisis, retinitis pigmentosa, glaucoma, Usher syndrome, cone-rod dystrophy, Stargardt disease, inherited macular degeneration, chorioretinal degeneration, Leber congenital amaurosis, congenital stationary night blindness, choroideremia, Bardet-Biedl syndrome, macular telangiectasia, Leber's hereditary optic neuropathy, retinopathy of prematurity, and a disorder of color vision.

24. A method of treating a disease or disorder of the retina of a subject in need thereof, comprising administering to the subject by intravitreal injection the recombinant AAV virion of any one of embodiments 1-19 or the pharmaceutical composition of embodiment 20.

25. The method of embodiment 24, wherein the disease or disorder is acute macular neuroretinopathy, Behcet's disease, choroidal neovascularization, diabetic uveitis, histoplasmosis, macular degeneration, edema, multifocal choroiditis, ocular trauma which affects a posterior ocular site or location, ocular tumor, central retinal vein occlusion, diabetic retinopathy, proliferative vitreoretinopathy (PVR), retinal arterial occlusive disease, retinal detachment, uveitic retinal disease, sympathetic ophthalmia, Vogt Koyanagi-Harada (VKH) syndrome, uveal diffusion, a posterior ocular condition caused by or influenced by an ocular laser treatment, posterior ocular conditions caused by or influenced by a photodynamic therapy, photocoagulation, radiation retinopathy, epiretinal membrane disorders, branch retinal vein occlusion, anterior ischemic optic neuropathy, diabetic retinal ischemia, ischemic retinopathy, non-retinopathy diabetic retinal dysfunction, retinoschisis, retinitis pigmentosa, glaucoma, Usher syndrome, cone-rod dystrophy, Stargardt disease, inherited macular degeneration, chorioretinal degeneration, Leber congenital amaurosis, congenital stationary night blindness, choroideremia, Bardet-Biedl syndrome, macular telangiectasia, Leber's hereditary optic neuropathy, retinopathy of prematurity, or a disorder of color vision.

26. The recombinant AAV virion of any one of embodiments 1-19 for use in a method of treating a disease or disorder of the retina of a subject in need thereof, wherein the method comprises administering a pharmaceutical composition comprising the recombinant AAV virion to the subject by intravitreal injection.

27. The recombinant AAV virion of any one of embodiments 1-19 for use in the preparation of a medicament for the treatment of a disease or disorder of the retina of a subject.

28. The recombinant AAV virion of embodiment 26 or 27, wherein the disease or disorder is age-related macular degeneration (AMD), wet-AMD, dry-AMD, retinal neovascularization, choroidal neovascularization, diabetic retinopathy, proliferative diabetic retinopathy, retinal vein occlusion, central retinal vein occlusion, branched retinal vein occlusion, diabetic macular edema, diabetic retinal ischemia, ischemic retinopathy, or diabetic retinal edema.

29. A variant AAV capsid protein comprising a modified sequence comprising one or more amino acid substitutions within amino acid residues 570-579 relative to a parental AAV capsid protein, wherein the modified sequence comprises HKFKSGD (SEQ ID NO: 1), and wherein the amino acid residue numbering corresponds to an AAV5 VP1 capsid protein.

30. The variant AAV capsid protein of embodiment 29, wherein the parental AAV capsid protein is an AAV5 capsid protein or an AAV5 and AAV2 hybrid capsid protein.

31. The variant AAV capsid protein of embodiment 29 or 30, wherein the parental AAV capsid protein is an AAV2.5T capsid protein.

32. The variant AAV capsid protein of any one of embodiments 29-31, wherein the parental AAV capsid protein is an AAV2.5T VP1 capsid protein.

33. The variant AAV capsid protein of any one of embodiments 29-32, wherein the modified AAV capsid protein comprises LAHKFKSGDA (SEQ ID NO: 3) at amino acid residues 570-579 relative to the parental AAV capsid protein.

34. The variant AAV capsid protein of any one of embodiments 29-33, comprising a capsid sequence having at least 85% homology to the amino acid sequence set forth in SEQ ID NO: 4 or SEQ ID NO:5.

35. The variant AAV capsid protein of any one of embodiments 29-34, comprising a capsid sequence set forth in SEQ ID NO:6 or SEQ ID NO:7.

36. A nucleic acid comprising a nucleic acid sequence encoding the variant AAV capsid protein of any of embodiments 29-35.

37. An expression vector comprising the nucleic acid of embodiment 36, wherein the nucleic acid sequence encoding the variant AAV capsid protein is operably linked to a promoter sequence.

38. The expression vector of embodiment 37, further comprising a nucleic acid that encodes a rep protein.

39. A cell comprising the expression vector of embodiment 37 or 38.

40. The cell of embodiment 39, further comprising a nucleic acid that encodes a therapeutic gene product.

41. The cell of embodiment 40, wherein the therapeutic gene product is a siRNA, a miRNA, or a protein.

42. The cell of embodiment 40 or 41, wherein the therapeutic gene product is an anti-vascular endothelial growth factor (anti-VEGF) gene product.

43. The cell of embodiment 40 or 41, wherein the therapeutic agent is an opsin.

44. The cell of any one of embodiments 40-43, wherein the polynucleotide encoding the therapeutic gene product is flanked by one or more AAV ITRs.

45. The cell of embodiment 44, wherein the one or more AAV ITRs are AAV1, AAV2, AAV3, AAV4, AAV5, AAV6, AAV7, AAV5, AAV5, AAV10, avian AAV, bovine AAV, canine AAV, equine AAV, primate AAV, non-primate AAV, or ovine AAV ITRs or variants thereof.

46. The cell of embodiment 44 or 45, wherein the one or more AAV ITRs are AAV2 ITRs or AAV5 ITRs.

EXAMPLES

Example 1: Construction of AAV2.5T Mutant Libraries

AAV2.5T is a hybrid capsid containing regions from AAV2 and AAV5, described in U.S. Pat. No. 9,441,244, the disclosure of which is incorporated in its entirety. AAV2.5T is capable of transducing the retina when delivered subretinally, but not when injected intravitreally. AAV2.5T transduction may be blocked by the inner limiting membrane (ILM), which is enriched with heparan sulfate proteoglycan (HSPG).

The surface-exposed domains of AAV2.5T are identical to that of AAV5 except for a single substitution of A to T in aa582 of AAV2.5T (aa581 of AAV5), a mutation which appears to increase infectivity in mammalian cells without impacting AAV5's typical sialic acid receptor binding. AAV5 and AAV2.5T have negligible heparan sulfate binding, whereas AAV2 has high affinity for heparan sulfate.

To develop a novel AAV variant with enhanced ability to cross the ILM and transduce retinal cells upon delivery by intravitreal injection, AAV mutant libraries with loop substitution and insertions were generated from the AAV2.5T capsid in the region analogous to the HSPG binding region of AAV2, as determined by amino acid alignment.

Two mutant libraries were generated by synthesis of DNA fragments with a random 7 amino acid loop. Since there were 20 possible amino acids for each of the 7 amino acid positions, the theoretical diversity of these fragment libraries was approximately $1 \times 10^9$ unique variants. These mutant loops were flanked by the amino acids LA at the 5' end and by A at the 3' end.

Using these fragment libraries, a loop insertion library (LIL) was generated by inserting the 10 amino acid loops at position 577 of the AAV2.5T capsid sequence, in the receptor binding region.

A second library was generated by substituting a sequence in the surface exposed region of the capsid with loop variant sequences between amino acids 571 and 580 (numbering from first amino acid of VP1). This library was termed the loop substitution library (LSL).

These AAV variant capsids were cloned into plasmids to make individual viral packaging cell libraries (by transient transfection with phiC31 integrase at a 1:50 ratio (plasmid:phiC31), as described in WO2017112868A1). The resulting packaging cell libraries produce mutant AAV virions made up of a vector genome containing a mutant Cap gene packaged within the capsid proteins encoded by that genome, with a low level of cross packaging. To ascertain diversity of the cell library, gDNA was isolated from each library and NGS was performed. The diversities were approximately ~725,000 unique variants in LIL and ~558,000 unique variants in LSL.

Example 2: AAV Library Screens in NHP Eyes

To investigate ability of the mutant AAV capsids to cross the ILM, the libraries of variant AAV virions were screened in vivo for the ability to pass through the inner limiting membrane (ILM) and infect retinal cells in non-human primate (NHP) eyes.

The LIL and LSL mutant AAV capsid libraries were injected intravitreally into the eyes of 3 African Green monkeys (*Chlorocebus sabaeus*) each at doses between $6 \times 10^9$ and $9 \times 10^9$ vg per eye. Four to six weeks post injection, the animals were sacrificed and retinal tissue explants from each animal were isolated. The vitreous and retina with choroidal sub-tissues were isolated and the eyeball was cut along the limbus and the anterior portion of the eye discarded. The vitreous was then removed while leaving the retina attached to the eyecup. The eye cup was transferred into $CO_2$-independent media. The retina and RPE/Choroid were cut to make a retinal flat-mount. The entire flat-mount was placed, photoreceptor layer facing down, onto the polycarbonate insert membrane of a 10 cm Trans-well plate containing 10 mL of $CO_2$-independent media. When the retina settled flat onto the insert, the media was removed so that the retina was exposed to the atmosphere.

The retina was transduced with human Ad5 virus (diluted in Neurobasal-A media without antibiotics or antimycotics) at a multiplicity of infection (MOI) of 1000 by adding the Ad5 solution on top of the tissue for 2 hours. Coinfection with Ad5 virus was used to increase expression of Cap RNA from mutant AAV virions present in the retinal tissue, thereby increasing the quantity of mutant capsid RNA in infected cells for subsequent detection.

After the initial incubation, Neurobasal-A+(B27 supplement, 1× GlutaMAX, 1× Antibiotic-Antimycotic) medium was added to the bottom of the well so that it was in contact with the bottom of the insert but did not cover the tissue (~10 ml), and the tissue explants were incubated with $CO_2$ at 37° C. for 2 days. Following incubation, the insert was removed from the plate, placed onto a clean flat surface, and three punches were made as shown in FIG. 1A. Briefly, a 5 mm punch of neural retina with RPE/choroid was taken from the macula. A second concentric punch was then made using a 10 mm punch to isolate the region of retina and RPE/choroid surrounding the macula within the blood arcades, which was named as the parafovea. The remaining peripheral retina and RPE/choroid were then collected.

RNA was then extracted from each of the tissue punches and converted to cDNA by RT-PCR followed by one round of PCR. The resulting PCR products were then cloned back into plasmids and sequenced to determine the sequences of mutant AAV capsids that were able to successfully cross the ILM and infect retinal cells in the monkey eye.

For the second and third rounds of screening, LIL and LSL variants extracted from each of the individual retinal locations (punches) were mixed to create one library of variants for each location. These library pools were then used to generate cell and AAV capsid libraries that were injected separately into African green monkey (AGM) eyes and collected using the same retinal-punch strategy as above. Additionally, in one instance, the retinal pigment epithelium was isolated and variants were recovered from that tissue.

Using NGS analysis, AAV2.5T.LSV1 was identified. AAV2.5T.LSV1 is a loop substitution variant originating from the LSL library with the following amino acid loop sequence: LAHKFKSGDA (SEQ ID NO: 3). AAV2.5T.LSV1 was the 48$^{th}$ most abundant variant from the macular region in screening round 2. In screening round 3, AAV2.5T.LSV1 was the second most abundant variant found in the parafovea and the most abundant variant found in the RPE regions. The relative abundances of the top variants at each screening round are shown in FIGS. 1B-1E.

Example 3: Production of AAV2.5T.LSV1 in HEK293 Cells

AAV2.5T.LSV1 was manufactured for further characterization using the triple transfection method in HEK293 cells. The resulting AAV2.5T.LSV1 titers were greater than $1 \times 10^{13}$ vg/ml, demonstrating that AAV2.5T.LSV1 had a good packaging ability.

Example 4: Heparin Binding Affinity of AAV2.5T.LSV1

The ability of AAV2.5T.LSV1 to bind HSPG was assessed by performing a heparin binding assay using a pre-packed GE heparin column. The heparan binding of AAV2.5T.LSV1 was compared to AAV2.5T and to two other variants produced in the screens described above. The vector was loaded on the column, which was then washed, and finally eluted with increasing concentrations of NaCl (100 mM-1 M). Fractions of Load, Flow-through, Wash, and Elution were collected and analyzed by dot-blot using the B1 antibody.

Figure 2:
FIG. 2 shows the dot blot results of heparin column fractions from AAV2.5T and the variant capsid AAV2.5T.LSV1. Eluates E1 to E10 have increasing concentrations of NaCl of 0.1M (E1), 0.2M (E2), 0.3M (E3), 0.4M (E4), 0.5M (E5), 0.6M (E6), 0.7M (E7), 0.8M (E8), 0.9M (E9) and 1.0M (E10).

As shown in FIG. 2, AAV2.5T does not bind to heparin. By contrast, AAV2.5T.LSV1 has the ability to bind heparin.

Example 5: Expression and Tropism in Pig Retinal Explants

Figure 3:
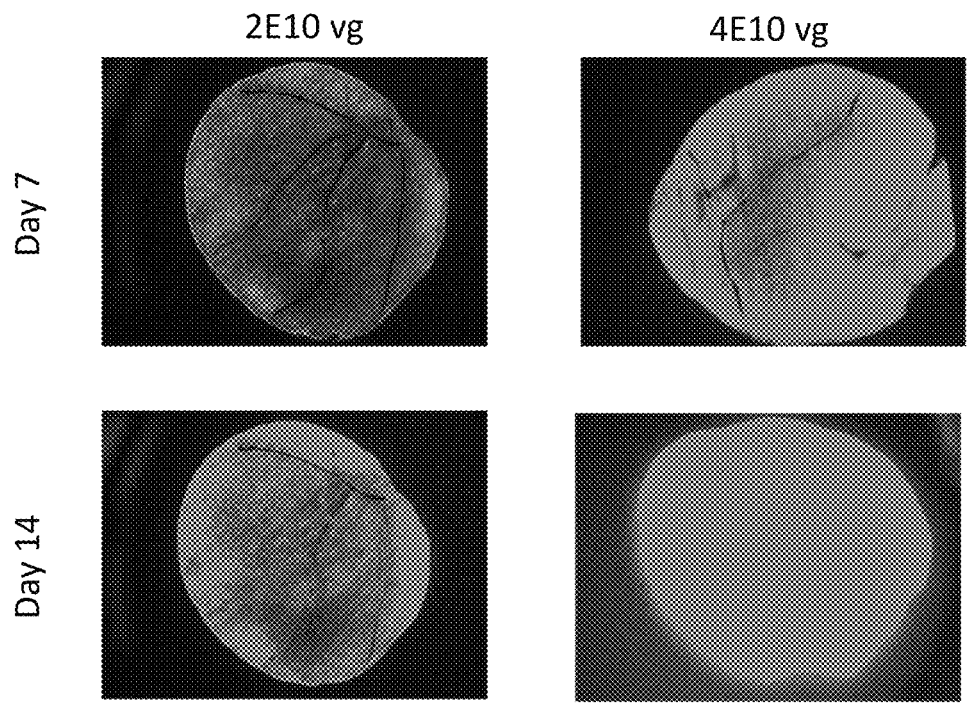
FIG. 3 shows live images of GFP expression in 6 mm pig retinal explants on day 7 or day 14 following infection with 2 E+10 vg (i.e., 2E10 vg) or 4 E+10 vg (i.e., 4E10 vg) of AAV2.5T.LSV1 virions encoding GFP.
Figure 5A:
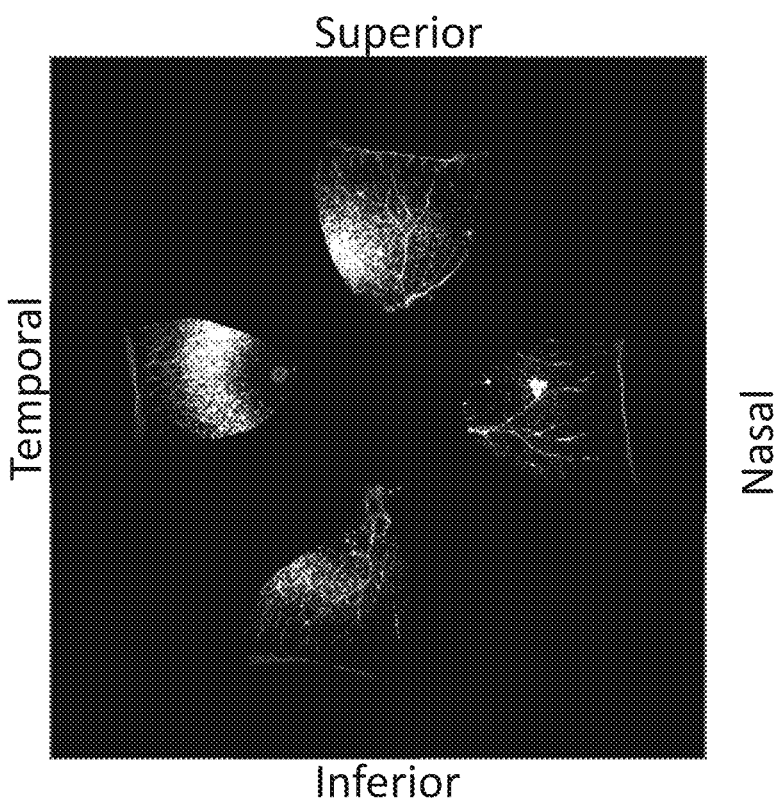
FIGS. 5A-5B provide fluorescence images of flat-mounted retina of an African green monkey after intravitreal administration of AAV2.5T.LSV1 virions encoding GFP.
Figure 5B:
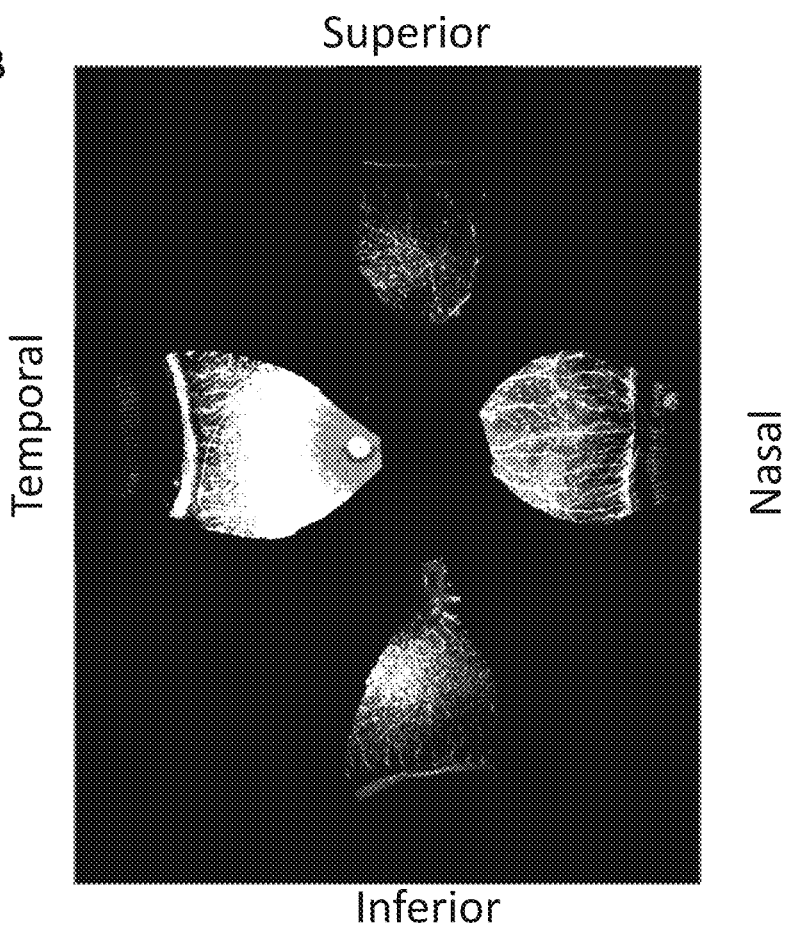
Figure 7:
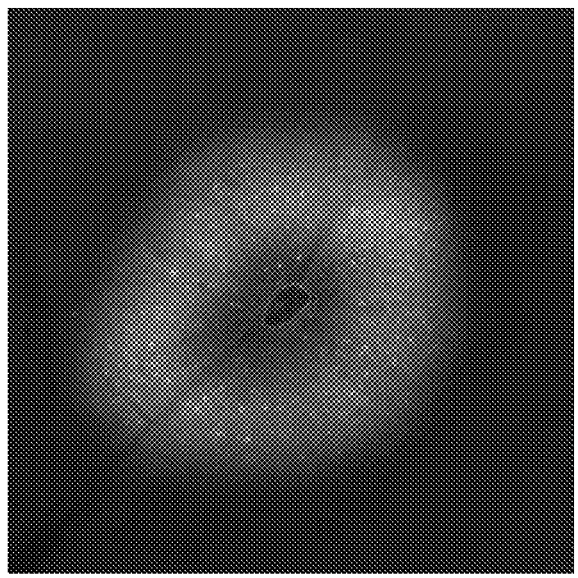
FIG. 7 provides a fluorescence image of the GFP expressed in the fovea of the eye of an African green monkey after intravitreal administration of AAV2.5T.LSV1 virions encoding GFP.
Figure 8:
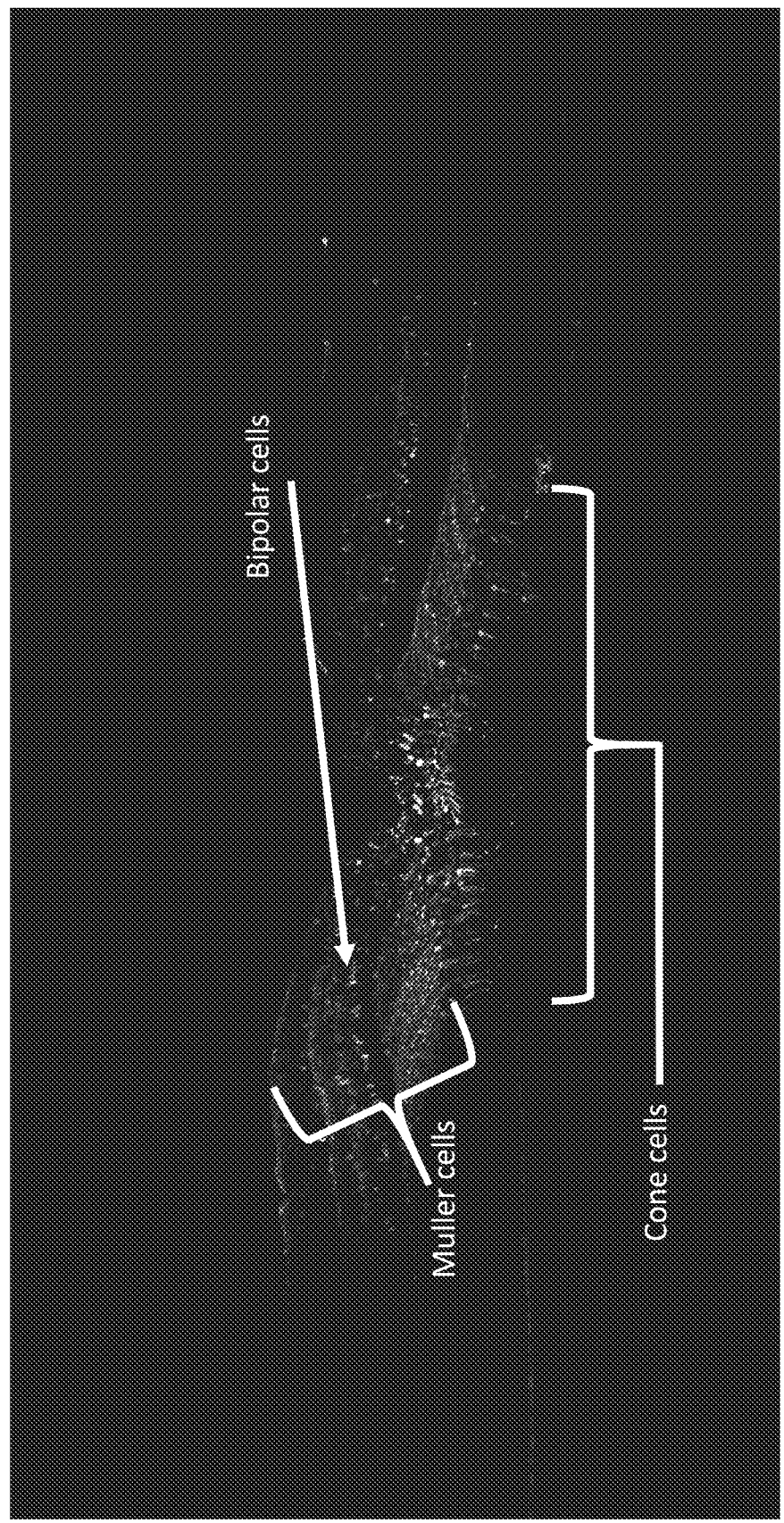
FIG. 8 provides a fluorescence image of the GFP expressed in the fovea of the eye of an African green monkey after intravitreal administration of AAV2.5T.LSV1 virions encoding GFP.
Figure 9A:
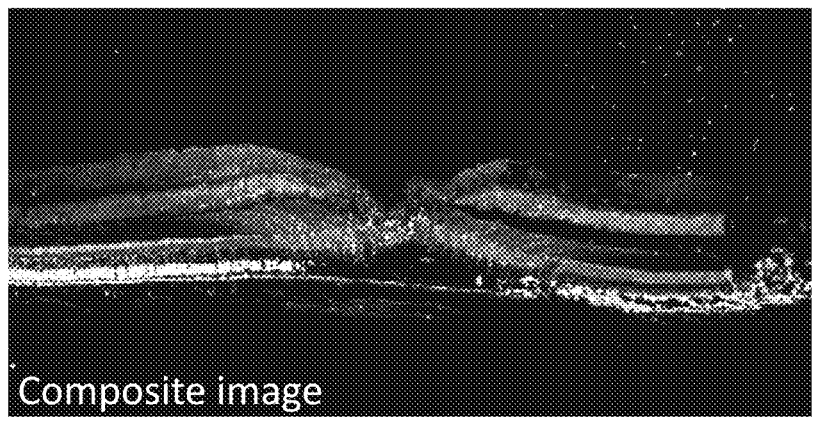
FIGS. 9A-9D provide fluorescence images of the fovea of the eye of an African green monkey after intravitreal administration of AAV2.5T.LSV1 virions encoding GFP.
Figure 9B:
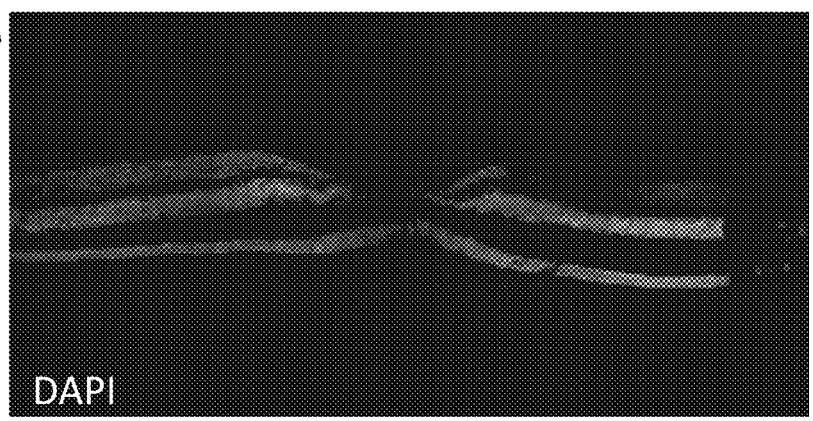
Figure 9C:
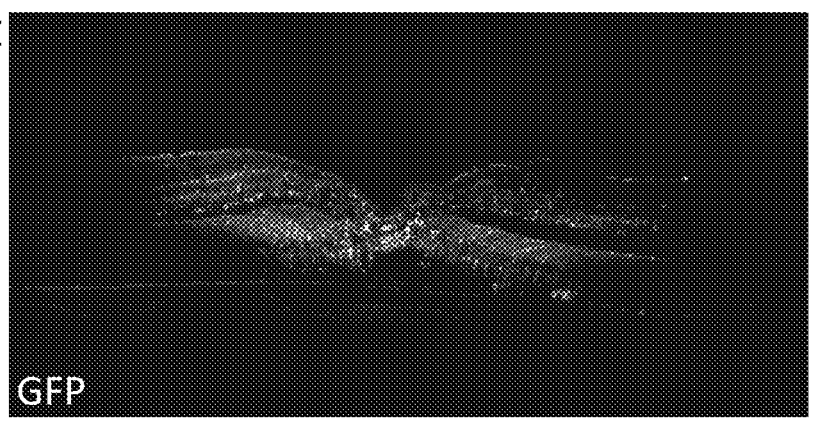
Figure 9D:
Figure 10A:
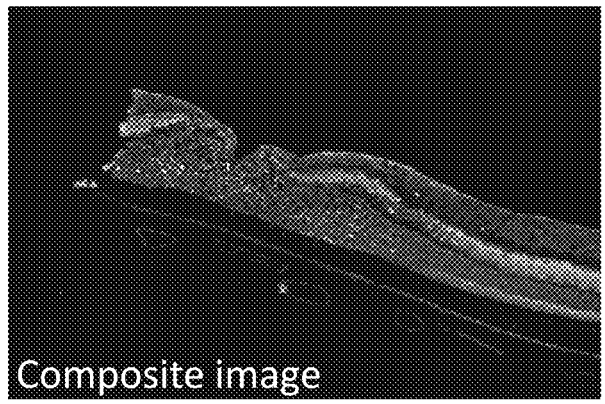
FIGS. 10A-10D provide fluorescence images of the fovea of the eye of an African green monkey after intravitreal administration of AAV2.5T.LSV1 virions encoding GFP.
Figure 10B:
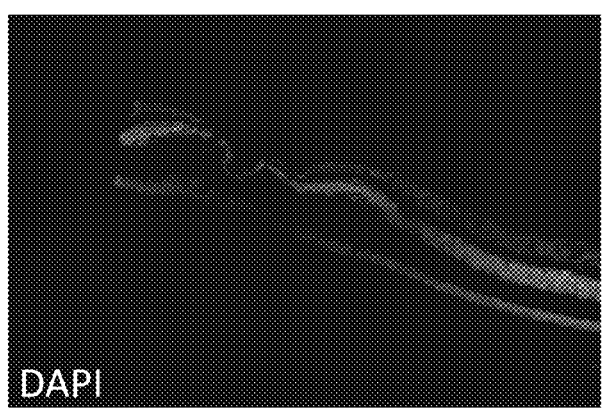
Figure 10C:
Figure 10D:
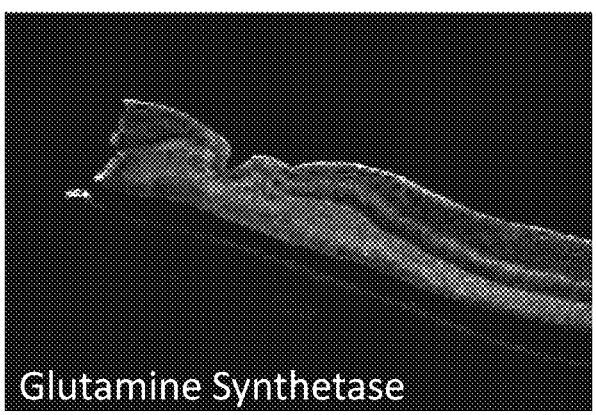
Figure 11:
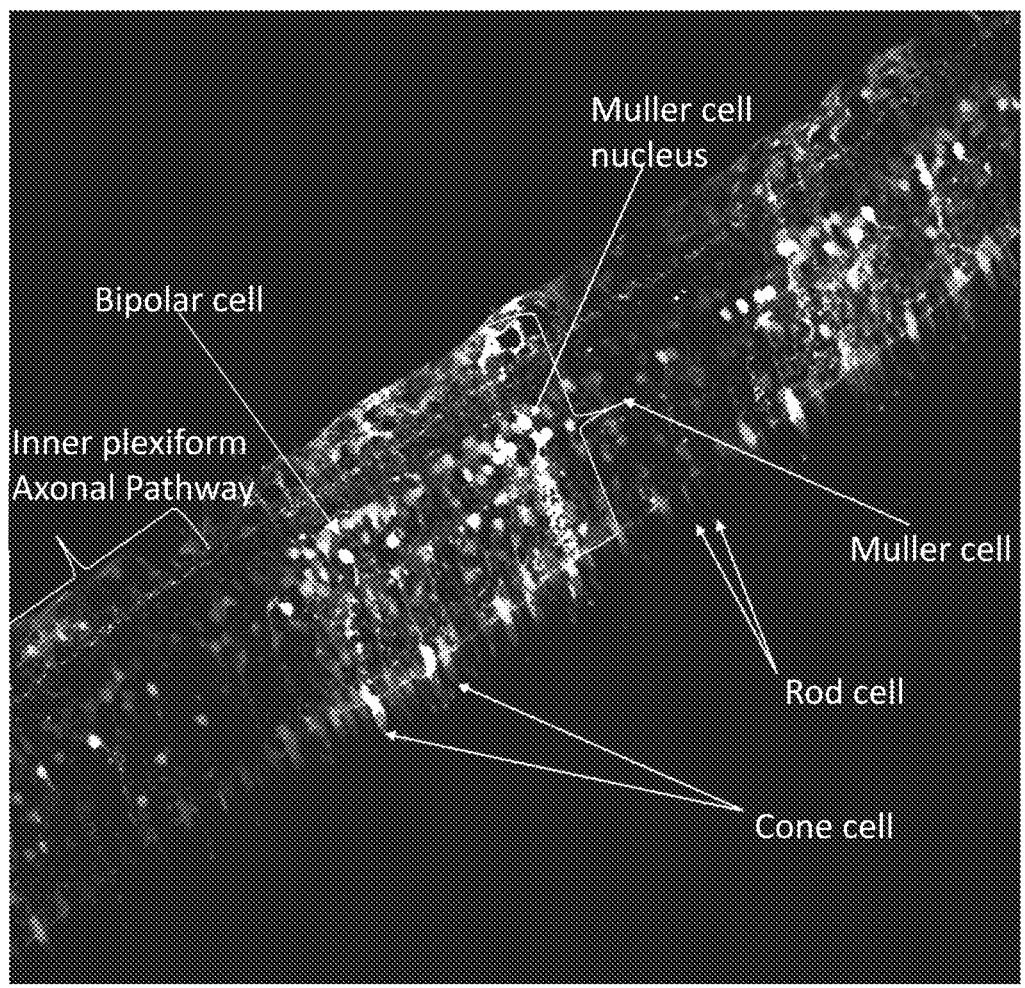
FIG. 11 provides a fluorescence image of the GFP expressed in the retina of the eye of an African green monkey after intravitreal administration of AAV2.5T.LSV1 virions encoding GFP.
Figure 12A:
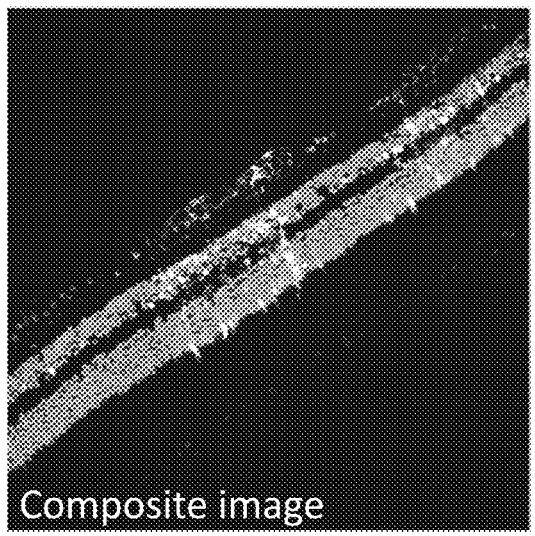
FIGS. 12A-12C provide fluorescence images of the retina of the eye of an African green monkey after intravitreal administration of AAV2.5T.LSV1 virions encoding GFP.
Figure 12B:
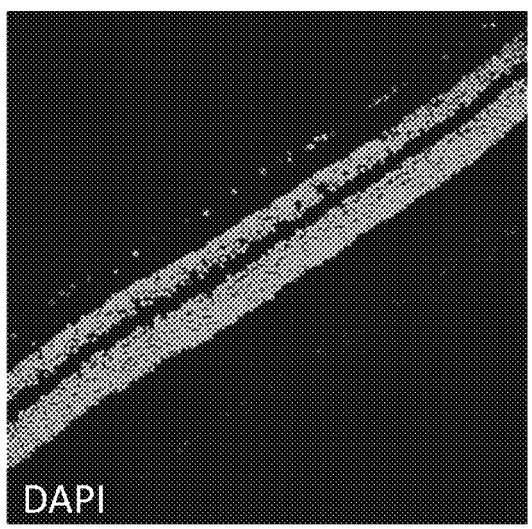
Figure 12C:
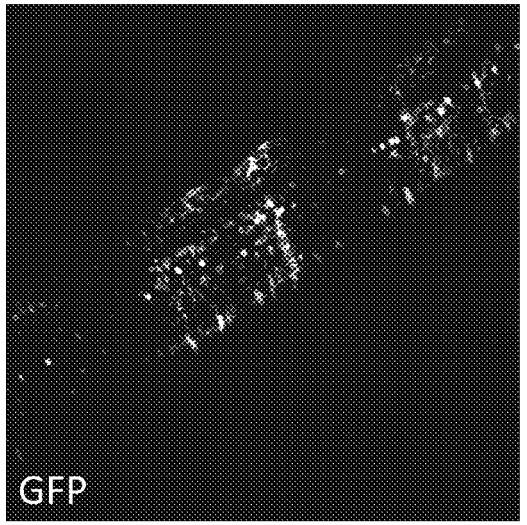
Figure 13A:
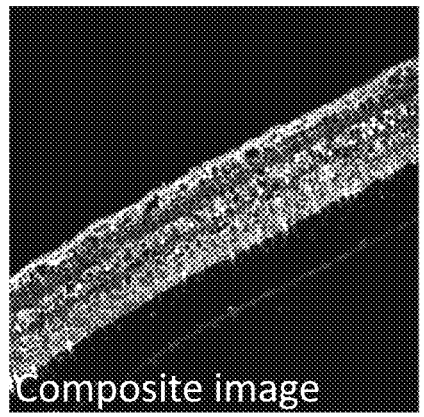
FIGS. 13A-13D provide fluorescence images of the retina of the eye of an African green monkey after intravitreal administration of AAV2.5T.LSV1 virions encoding GFP.
Figure 13B:
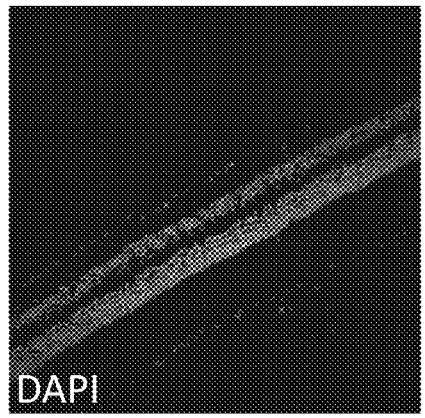
Figure 13C:
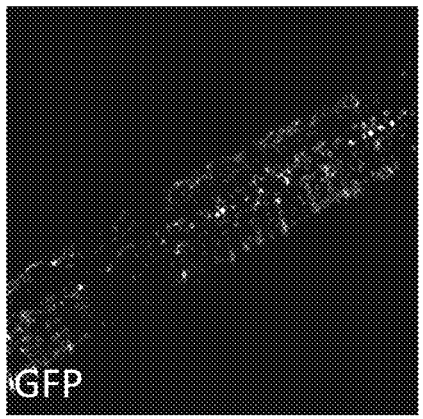
Figure 13D:
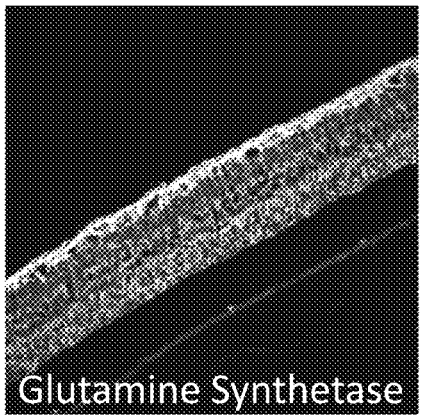
Figure 14A:
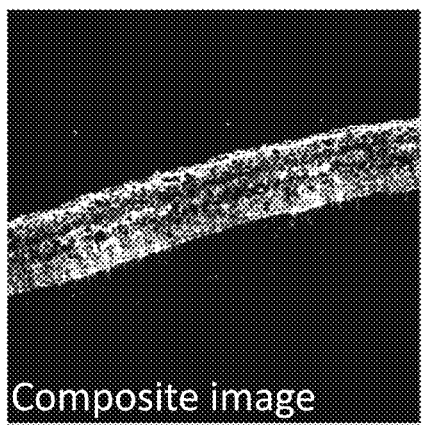
FIGS. 14A-14D provide fluorescence images of the retina of the eye of an African green monkey after intravitreal administration of AAV2.5T.LSV1 virions encoding GFP.
Figure 14B:
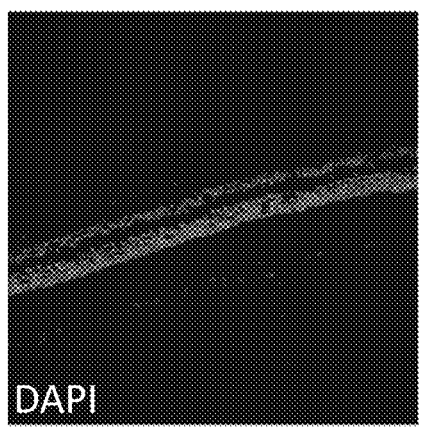
Figure 14C:
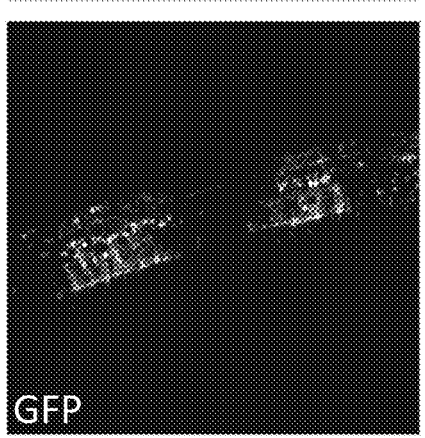
Figure 14D:
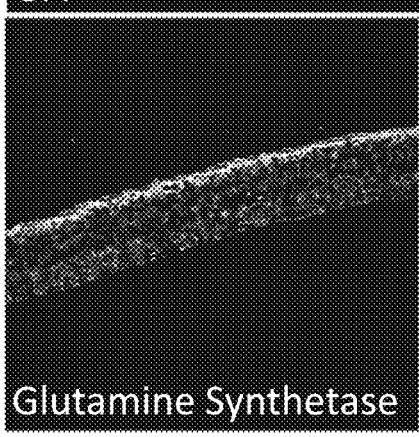
Figure 15A:
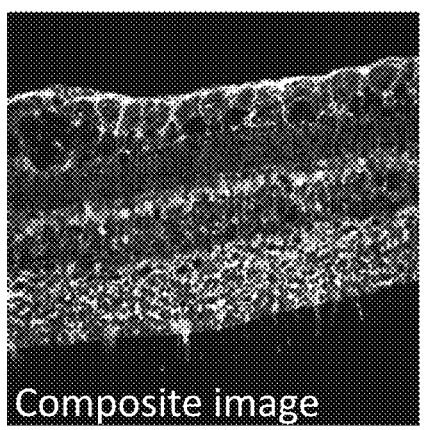
FIGS. 15A-15D provide fluorescence images of the retina of the eye of an African green monkey after intravitreal administration of AAV2.5T.LSV1 virions encoding GFP.
Figure 15B:
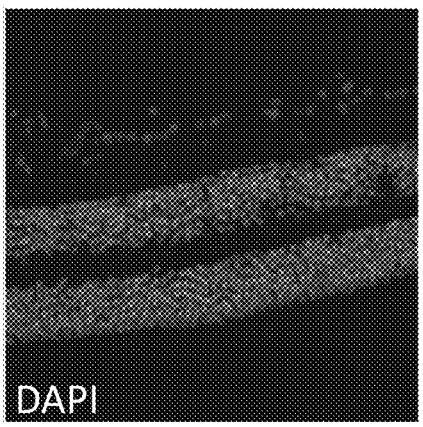
Figure 15C:
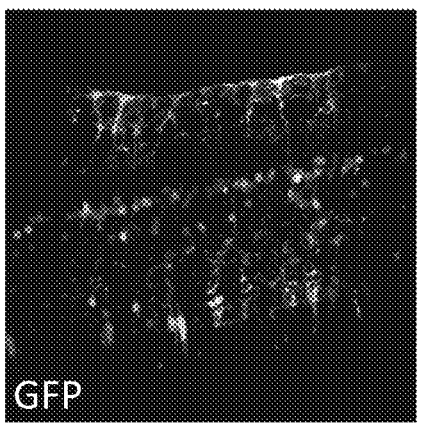
Figure 15D:
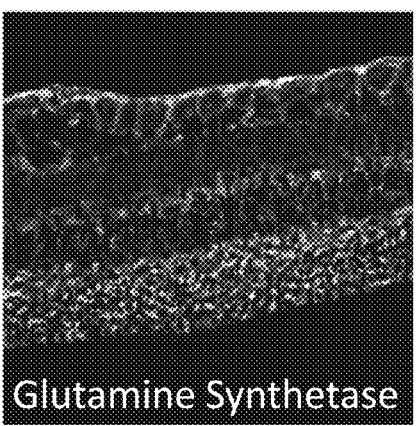
Figure 17A:
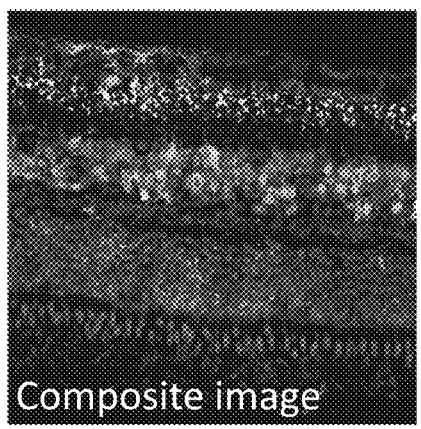
FIGS. 17A-17D provide fluorescence images of the retina of the eye of an African green monkey after intravitreal administration of AAV2.5T.LSV1 virions encoding GFP.
Figure 17B:
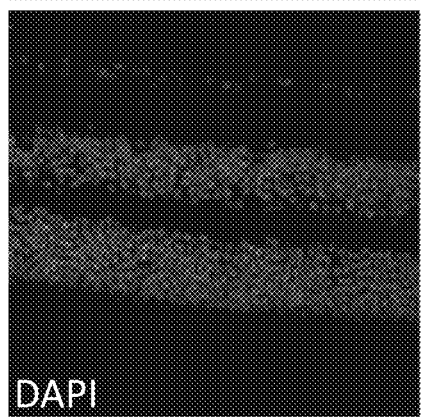
Figure 17C:
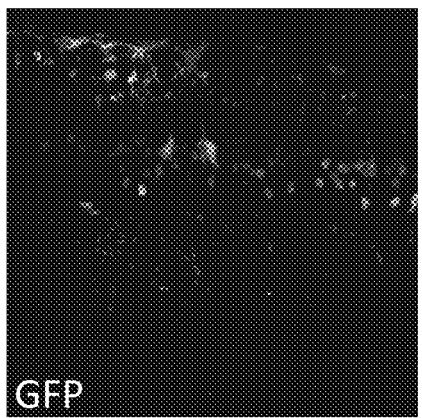
Figure 17D:
Figure 18A:
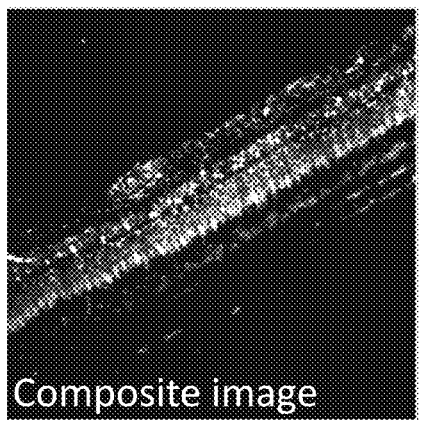
FIGS. 18A-18E provide fluorescence images of the retina of the eye of an African green monkey after intravitreal administration of AAV2.5T.LSV1 virions encoding GFP.
Figure 18D:
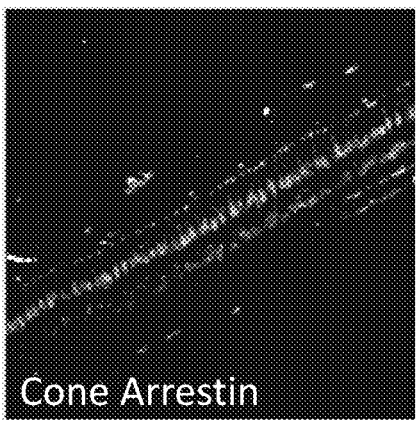
Figure 18B:
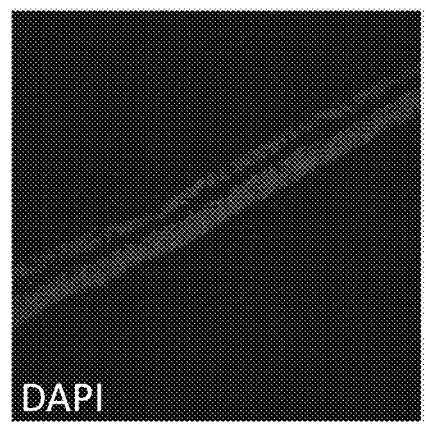
Figure 18E:
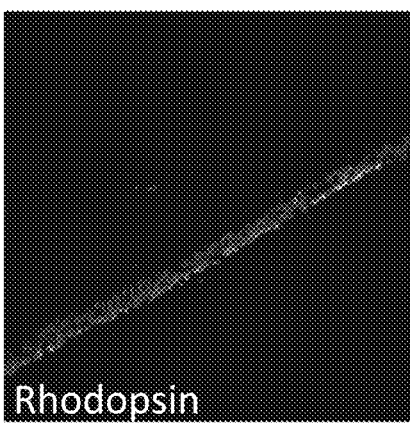
Figure 18C:
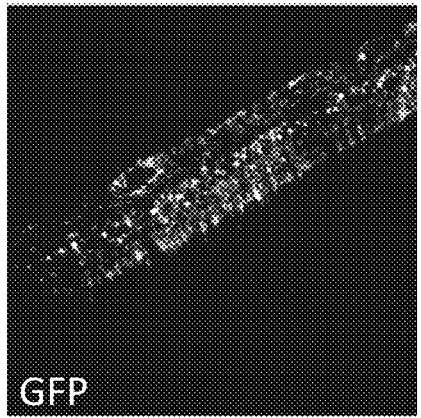
Figure 19A:
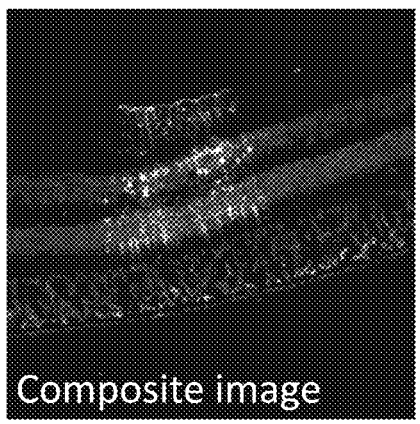
FIGS. 19A-19E provide fluorescence images of the retina of the eye of an African green monkey after intravitreal administration of AAV2.5T.LSV1 virions encoding GFP.
Figure 19D:
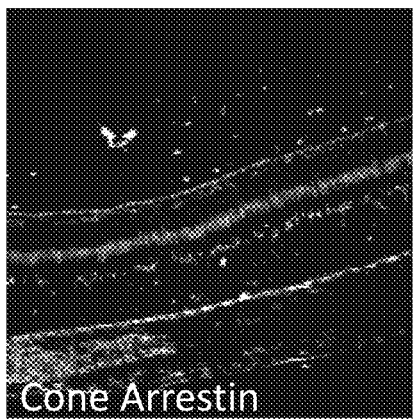
Figure 19B:
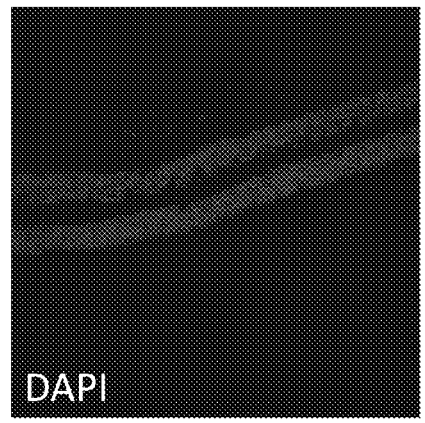
Figure 19E:
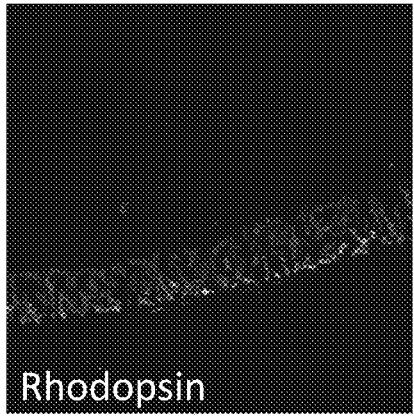
Figure 19C:
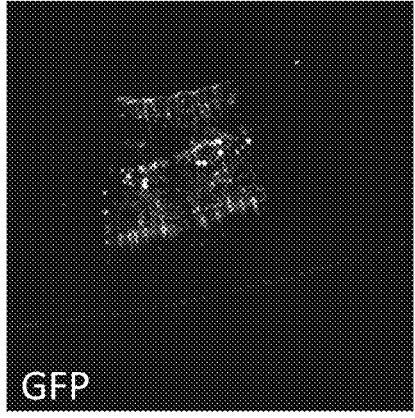
Figure 21A:
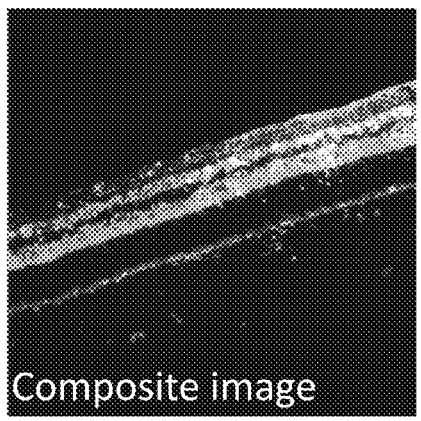
FIGS. 21A-21E provide fluorescence images of the retinal pigmented epithelium (RPE) of the eye of an African green monkey after intravitreal administration of AAV2.5T.LSV1 virions encoding GFP.
Figure 21D:
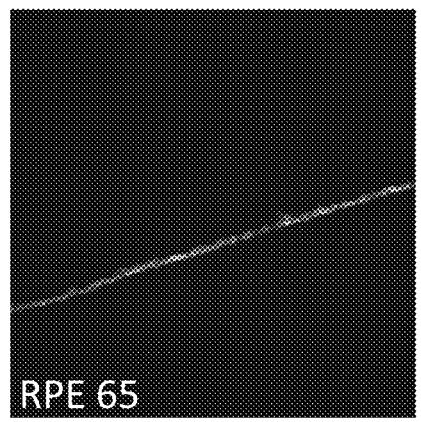
Figure 21B:
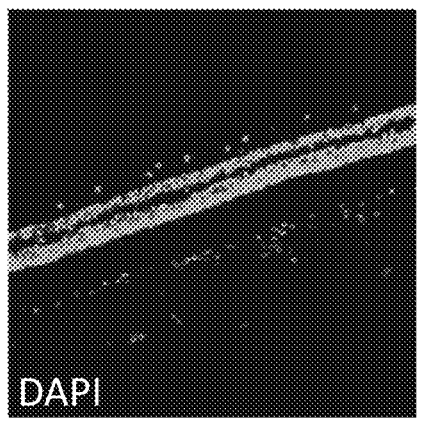
Figure 21E:
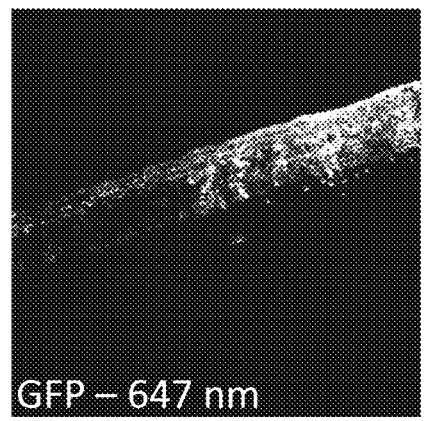
Figure 21C:
Figure 22A:
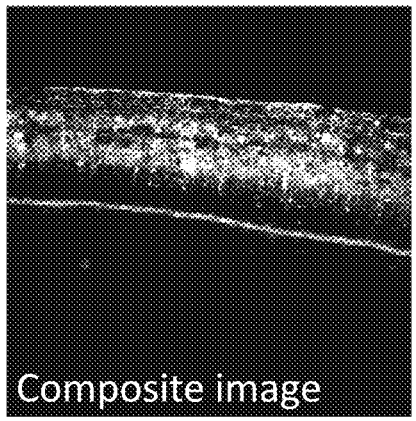
FIGS. 22A-22E provide fluorescence images of the retinal pigmented epithelium (RPE) of the eye of an African green monkey after intravitreal administration of AAV2.5T.LSV1 virions encoding GFP.
Figure 22D:
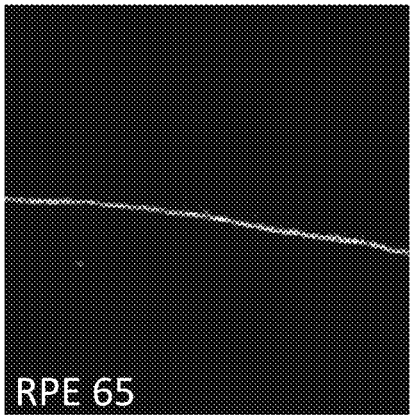
Figure 22B:
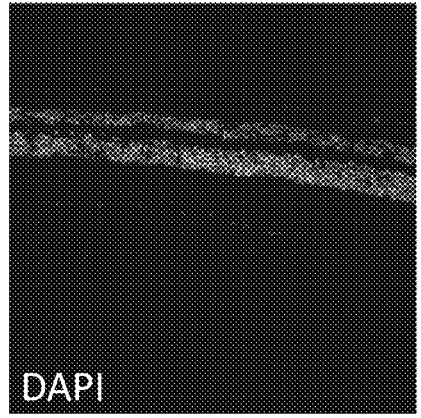
Figure 22E:
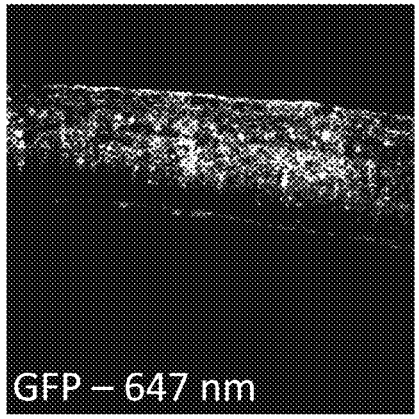
Figure 22C:
Figure 23A:
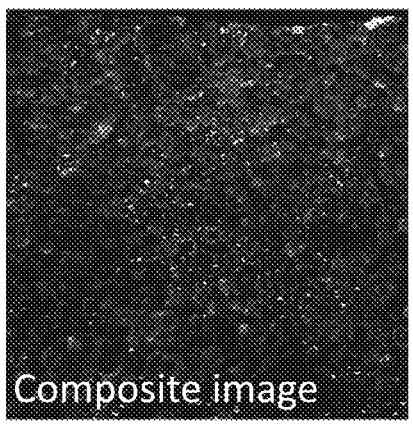
FIGS. 23A-23E provide planar fluorescence images of the retinal pigmented epithelium (RPE) of the eye of an African green monkey after intravitreal administration of AAV2.5T.LSV1 virions encoding GFP.
Figure 23D:
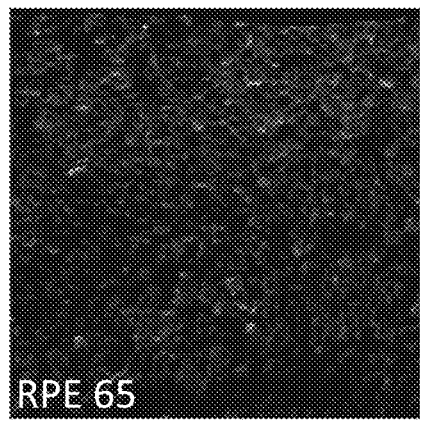
Figure 23B:
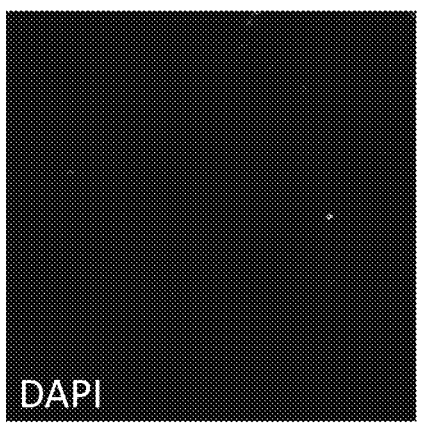
Figure 23E:
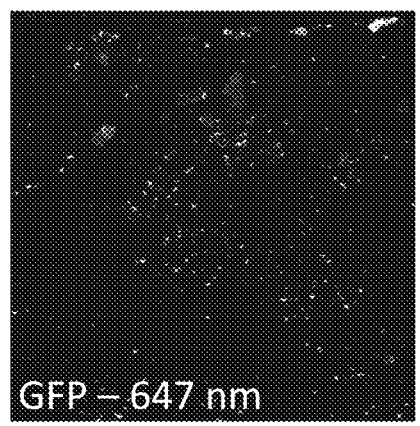
Figure 23C:
Figure 24A:
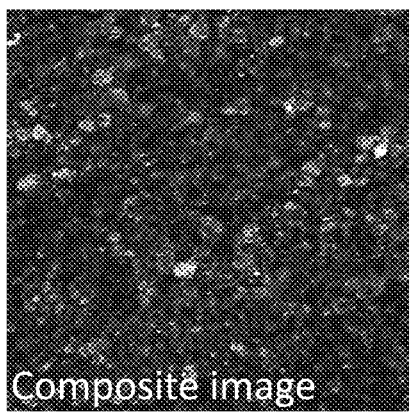
FIGS. 24A-24E provide planar fluorescence images of the retinal pigmented epithelium (RPE) of the eye of an African green monkey after intravitreal administration of AAV2.5T.LSV1 virions encoding GFP.
Figure 24D:
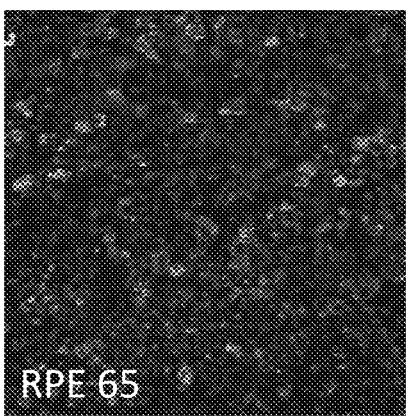
Figure 24B:
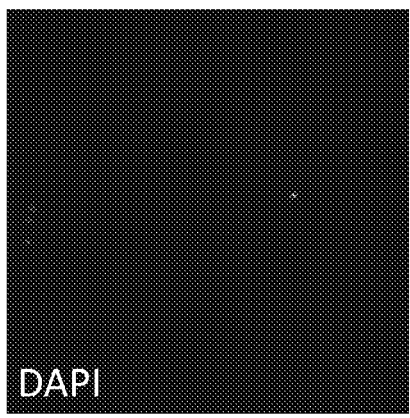
Figure 24E:
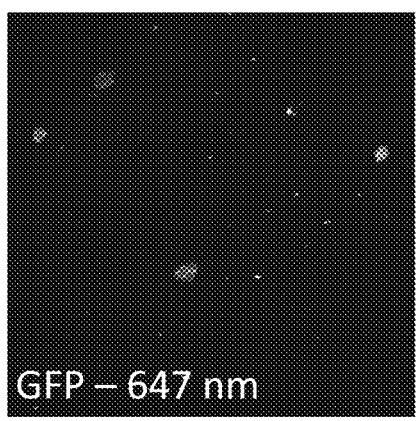
Figure 24C:
Figure 25A:
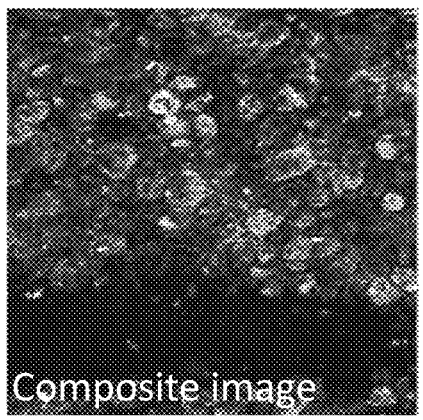
FIGS. 25A-25E provide planar fluorescence images of the retinal pigmented epithelium (RPE) of the eye of an African green monkey after intravitreal administration of AAV2.5T.LSV1 virions encoding GFP.
Figure 25D:
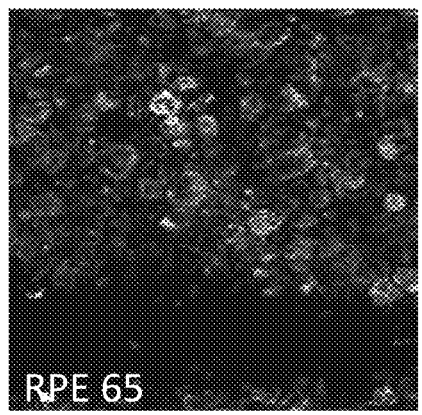
Figure 25B:
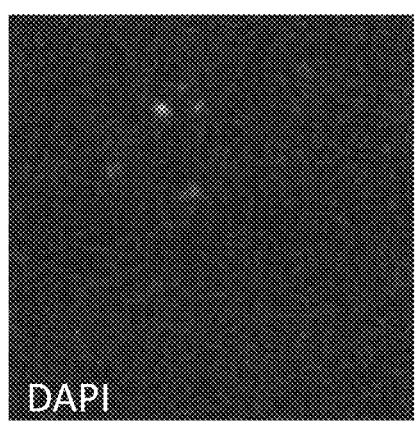
Figure 25E:
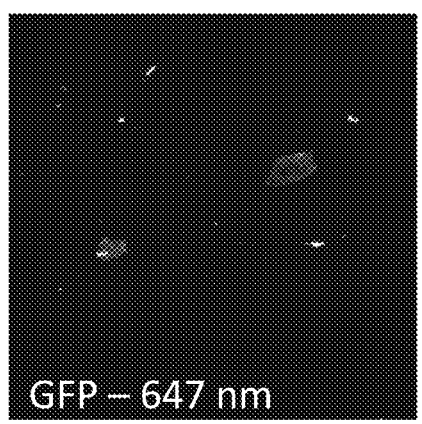
Figure 25C:
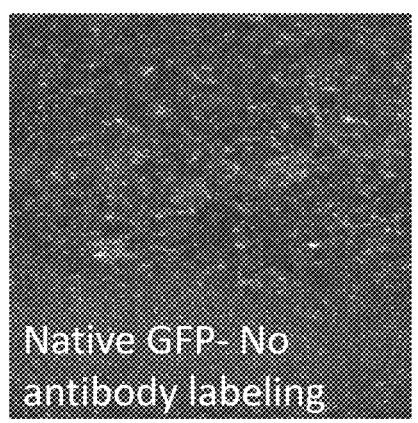

Ex vivo pig retinal explants were maintained on transwells as described in PCT/US2017/030636, the disclosure of which is incorporated in its entirety, and were transduced with a GFP reporter gene packaged into the AAV2.5T.LSV1 capsid with $2 \times 10^{10}$ vg or $4 \times 10^{10}$ vg. Live fluorescence images were captured at one and two weeks following transduction. FIG. 3 shows live imaging of pig retinal explants. These images suggest that AAV2.5T.LSV1 is able to efficiently transduce at least some cells of the porcine retina in culture.

Example 6: Expression Following Intravitreal Administration to Non-Human Primate Retina In vivo studies were performed in African green monkeys (*Chlorocebus sabaeus*), which were intravitreally injected with $5 \times 10^{11}$ vg/eye of AAV2.5T.LSV1 carrying a GFP expression cassette under the control of a ubiquitous promoter. Expression in the eyes was monitored weekly by fundus fluorescence and Heidelberg Spectralis imaging and is shown in FIGS. 4A-4E. Intravitreal delivery of AAV2.5T.LSV1-GFP resulted in GFP expression within the macula and blood arcades. The blood arcade region of the retina has the thickest ILM, which is thought to block transduction of retinal cells by most AAV when injected intravitreally.

Example 7: Evaluation of Expression Following Intravitreal Administration

The retinal tropism of AAV2.5T.LSV1 was evaluated in non-human primates following IVT injection.

African green monkeys (*Chlorocebus sabaeus*) were intravitreally (IVT) injected with $5 \times 10^{11}$ vg/eye of AAV2.5T.LSV1 carrying a GFP expression cassette under the control of a ubiquitous promoter in order to evaluate the tropism of AAV2.5T.LSV1.

The monkeys were sacrificed on day 35 post IVT injection and eyes were enucleated. Eyes were fixed in 4% paraformaldehyde for 24 hours upon enucleation, then cryoprotected with 30% sucrose/Sorenson's phosphate buffer overnight. Eyes were dissected into quadrants and the retina, including the RPE and choroid, were removed from the sclera. Retinal quadrants were flat-mounted on a slide and cover slipped under 30% Sucrose/Sorenson's phosphate buffer. 5× Tiled scans of Native GFP were acquired using a Zeiss Axio.Z1, and stitched using the Zeiss Zen Blue software. The resulting live fluorescence images for AAV2.5T.LSV1-GFP are shown in FIGS. 5A-5D.

GFP Intensity profiles were acquired from 5× scans of the portions of the flat-mounted retinas shown in FIGS. 5C-5D. Measurements were taken from the edge of the macula, closest to the optic nerve, to the ciliary body. About 20,000 measurement points spanning a total of 20 mm in length were plotted across the distance from the macula to the ciliary body (FIG. 5E).

Retinal flat-mounts were embedded in OCT mounting medium and frozen over isopentane. Cryo-sections were collected through the fovea, midperiphery, and periphery at 10 µm thickness and slides were stained for immunofluorescent labeling (IFL). Planar images of RPE were made by peeling the RPE away from the choroid in a section of flat-mounted retina, and inverting the section so that the RPE was placed face down on the slide, which was then stained for IFL. IFL was performed following 0.1% Triton-x permeabilization for 30 min followed by serum protein blocking for 1 hour with 5% normal donkey serum/6% bovine serum albumin in Sorenson's phosphate buffer. IFL was performed using the stains and antibodies shown in Table 2 overnight at 4° C.

TABLE 2

| | | Stains and Antibodies | | | | |
|---|---|---|---|---|---|---|
| Marker Type | Primary antibody or stain | Vendor for primary antibody or stain | Concentration of primary antibody or stain | Secondary antibody | Vendor for secondary antibody | Concentration of secondary antibody |
| Gene product expression | GFP | Abcam cat# ab13970 | 1:1000 | Donkey-anti Chicken 488 | Jackson Immuno Research Cat# 703-545-155 | 5 µg/ml |

TABLE 2-continued

Stains and Antibodies

| Marker Type | Primary antibody or stain | Vendor for primary antibody or stain | Concentration of primary antibody or stain | Secondary antibody | Vendor for secondary antibody | Concentration of secondary antibody |
|---|---|---|---|---|---|---|
| Rod photoreceptor cells | Rhodopsin | Millipore sigma Cat# MABN15 | 1:2500 | Donkey anti-Mouse Alexa Flour 555 | Thermo Scientific Cat# A-31570 | 5 µg/ml |
| Milner cells | Glutamine Synthetase | Sigma Cat# G2781 | 1:20000 | Donkey anti- Rabbit Alexa Flour 647 | Thermo Scientific Cat# A-31573 | 5 µg/ml |
| Bipolar cells | PKC-Alpha | Invitrogen Cat# MA1-157 | 1:50 | Donkey anti-Mouse Alexa Flour 555 | Thermo Scientific Cat# A-31570 | 5 µg/ml |
| Retinal ganglion cell bodies | Gamma Synuclein | Abcam Cat# | 1:100 | Donkey anti-Rabbit Alexa Flour 647 | Thermo Scientific Cat# A-31573 | 5 µg/ml |
| Cone photoreceptor cells | Cone Arrestin | Millipore Sigma Cat# AB 15282 | 1:500 | Donkey anti- Rabbit Alexa Flour 647 | Thermo Scientific Cat# A-31573 | 5 µg/ml |
| Retinal ganglion axon terminal pathways | Anti-beta III Tubulin (Tuj-1) | Abcam Cat# ab7751 | 1:500 | Donkey anti-Mouse Alexa Flour 555 | Thermo Scientific Cat# A-31570 | 5 µg/ml |
| Retinal pigmented epithelium (RPE) | RPE-65 555 | Abcam cat# ab78036 | 1:200 | Donkey anti-Mouse Alexa Flour | Thermo Scientific Cat# A-31570 | 5 µg/ml |
| Nuclei | DAPI | Invitrogen Cat# D21490 | 5 µg/ml | | | |

The tissue sections were imaged and the resulting images are shown in FIGS. 6A-25E. A summary of the cell types AAV2.5T.LSV1 virions demonstrated tropism for is shown in Table 3.

TABLE 3

Tropism of Virions

| | Fovea | Retina |
|---|---|---|
| Muller cells | Yes | Yes |
| Photoreceptors | Cones | Cones > rods |
| Bipolar cells | Yes | Yes |
| Axonal terminals within inner plexiform layer | Bipolar cells | Bipolar cells |
| Retinal pigmented epithelium | | Yes |

Figure 26A:
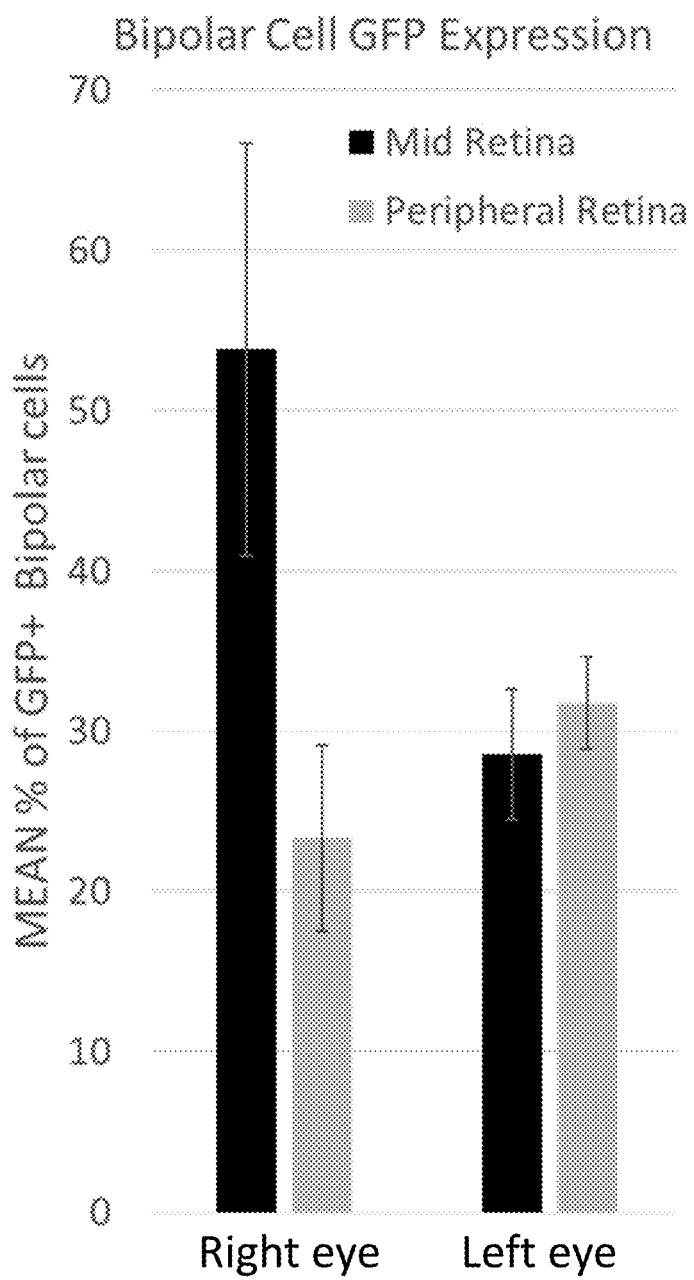
FIGS. 26A-26C provide the mean percent of GFP positive bipolar cells (FIG. 26A), cone cells (FIG. 26B), and RPE cells (FIG. 26C) in various regions in the retina in the eyes of African green monkeys after intravitreal administration of AAV2.5T.LSV1 virions encoding GFP.
Figure 26B:
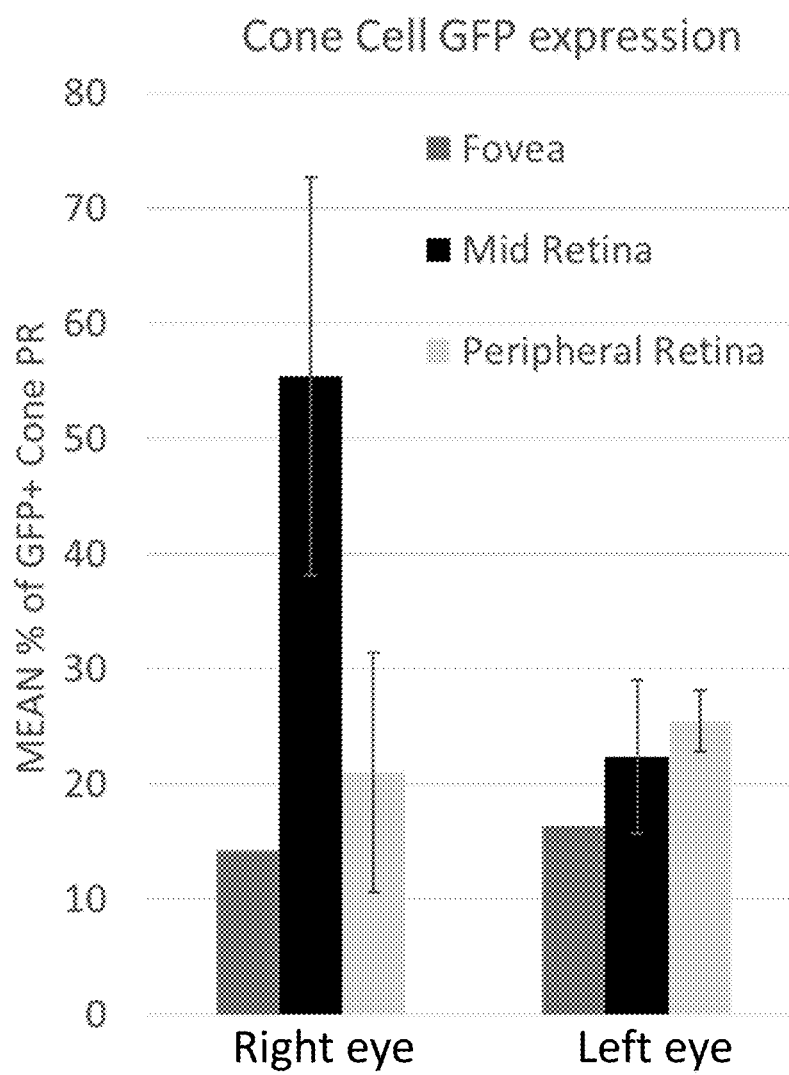
Figure 26C:
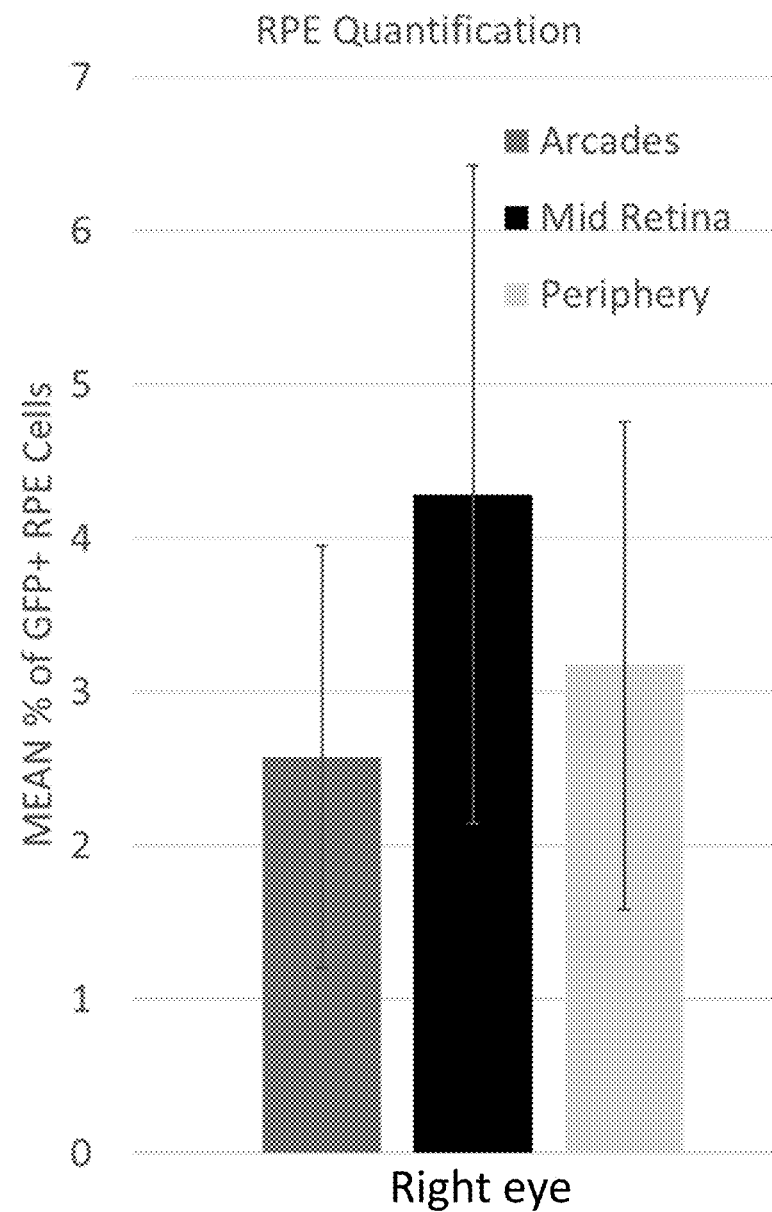

The percentage of GFP positive cells were quantified by manual cell counting of colocalization with cell-specific markers. The number of GFP positive bipolar cells, cone cells, and RPE cells in various regions in the retina are shown in FIGS. 26A-26C, respectively, and are summarized in Table 4. The number of GFP positive cells varied by location in the retina.

TABLE 4

Percentage of GFP positive cells

| Cell type (Location) | % of total |
|---|---|
| Cones (Fovea) | 14-16% |
| Photoreceptors (Mid and Peripheral Retina) | 25-55% |
| Bipolar cells (Mid and Peripheral Retina) | 25-50% |
| RPE cells (Mid and Peripheral Retina) | 2.5-4% |

Example 8: Determination of Neutralizing Antibody Profile

Neutralizing antibody (nAB) profiles are determined for AAV2.5T.LSV1 and AAV2.5T virus by in vitro assay. Briefly, serial dilutions of pooled human IgG antibodies (Gammaguard IVIG) are combined with AAV2.5T.LSV1 or AAV2.5T vector expressing GFP, and are used to transduce 293T cells. GFP expression is subsequently measured and inhibition of GFP expression is used to calculate the $IC_{50}$.

Example 9: Comparison of Neutralizing Antibody Profiles of AAV2.5T.LSV1 and AAV2

Neutralizing antibody (nAB) profiles were determined for AAV2.5T.LSV1 and AAV2 viruses by in vitro assay. Briefly, a 3-fold dilution series of pooled human IgG antibodies (Gammagard IVIG) was prepared and combined with AAV2.5T.LSV1 or AAV2 vectors expressing GFP (AAV2.5T.LSV1-CMV-GFP or AAV2-CMV-GFP, respectively). The mixtures were then used to transduce 293T cells. Cells were incubated for 3 days, and GFP expression was subsequently measured. Inhibition of GFP expression was used to calculate the $IC_{50}$. $IC_{50}$ is reported as the reciprocal dilution of the pooled human IgG antibody sample at which GFP expression is reduced by 50% (by way of example, an $IC_{50}$ of 100 indicates that IVIG diluted 1:100 reduced GFP expression by 50%). Larger $IC_{50}$ values indicate increased inhibition of AAV transduction by the antibodies present in pooled human IgG antibodies.

Figure 27A:
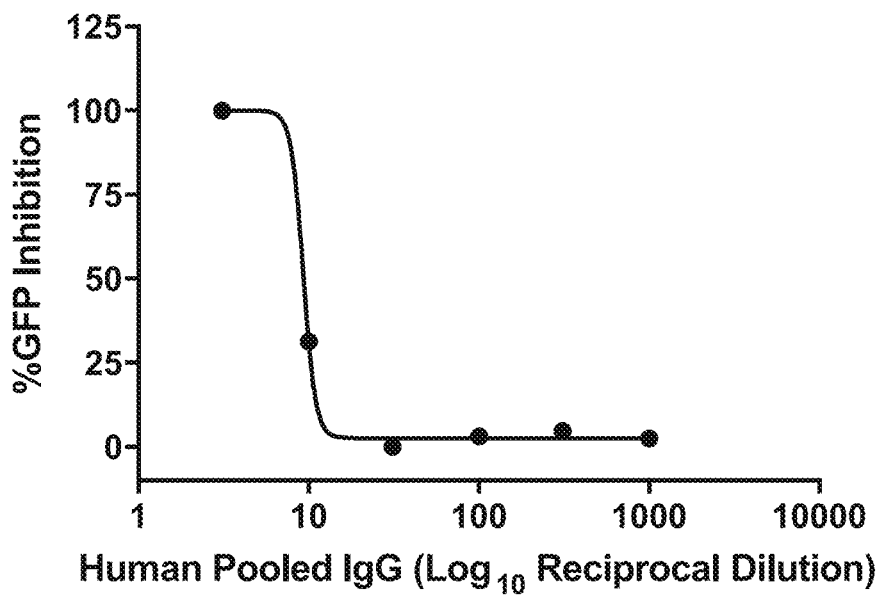
FIGS. 27A-27B provide neutralizing antibody (nAB) profiles against AAV2.5T.LSV1 and AAV2. Pooled human IgG antibodies (Gammagard IVIG) were combined with AAV2.5T.LSV1-CMV-GFP or AAV2-CMV-GFP. 293T cells were transduced with the mixtures and incubated for 3 days prior to measuring GFP expression.
Figure 27B:
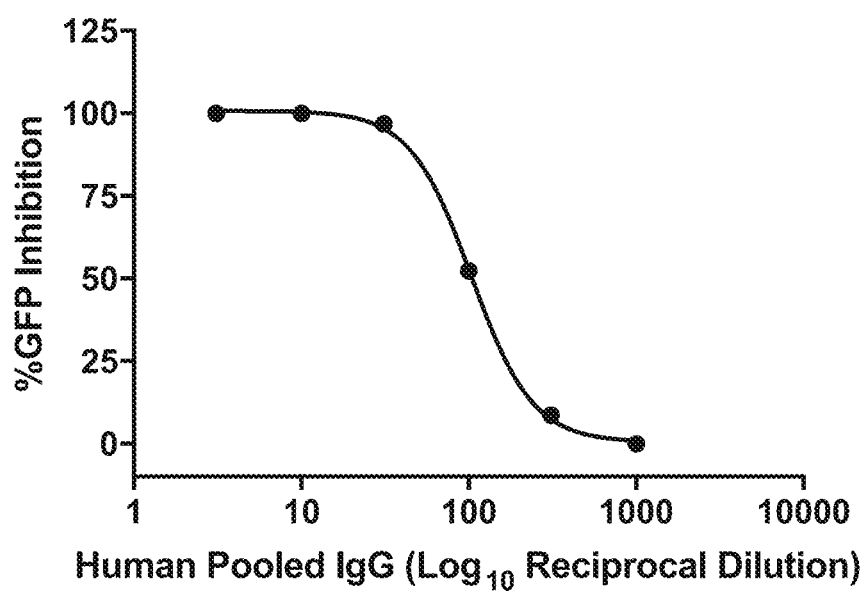

Inhibition curves for AAV2.5T.LSV1 and AAV2 are shown in FIGS. 27A-27B. AAV2 had a calculated $IC_{50}$ of 103.8, and AAV2.5T.LSV1 had a calculated $IC_{50}$ of 9.3.

| # | SEQUENCE | ANNOTATION |
|---|---|---|
| 1 | HKFKSGD | LSV1 Insert 1 |
| 2 | $X_1X_2$HKFKSGD$X_3$ | LSV1 Insert 2 |
| 3 | LAHKFKSGDA | LSV1 Insert 3 |
| 4 | MSFVDHPPDWLEEVGEGLREFLGLEAGPPKPKPNQQHQDQAR GLVLPGYNYLGPGNGLDRGEPVNRADEVAREHDISYNEQLEA GDNPYLKYNHADAEFQEKLADDTSFGGNLGKAVFQAKKRVLE PFGLVEEGAKTAPTGKRIDDHFPKRKKARTEEDSKPSTSSDA EAGPSGSQQLQIPAQPASSLGADTMSAGGGGPLGDNNQGADG VGNASGDWHCDSTWMGDRVVTKSTRTWVLPSYNNHQYREIKS GSVDGSNANAYFGYSTPWGYFDFNRFHSHWSPRDWQRLINNY WGFRPRSLRVKIFNIQVKEVTVQDSTTTIANNLTSTVQVFTD DDYQLPYVVGNGTEGCLPAFPPQVFTLPQYGYATLNRDNTEN PTERSSFFCLEYFPSKMLRTGNNFEFTYNFEEVPFHSSFAPS QNLFKLANPLVDQYLYRFVSTNNTGGVQFNKNLAGRYANTYK NWFPGPMGRTQGWNLGSGVNRASVSAFATTNRMELEGASYQV PPQPNGMTNNLQGSNTYALENTMIFNSQPANPGTTATYLEGN MLITSESETQPVNRVAYNVGGQMATNNQSSTTAPATGTYNLQ EIVPGSVWMERDVYLQGPIWAKIPETGAHFHPSPAMGGFGLK HPPPMMLIKNTPVPGNITSFSDVPVSSFITQYSTGQVTVEME WELKKENSKRWNPEIQYTNNYNDPQFVDFAPDSTGEYRTTRP IGTRYLTRPL | AAV5 VP1 |
| 5 | MAADGYLPDWLEDTLSEGIRQWWKLKPGPPPPKPAERHKDDS RGLVLPGYKYLGPFNGLDKGEPVNEADAAALEHDKAYDRQLD SGDNPYLKYNHADAEFQERLKEDTSFGGNLGRAVFQAKKRVL EPFGLVEEGAKTAPTGKRIDDHFPKRKKARTEEDSKPSTSSD AEAGPSGSQQLQIPAQPASSLGADTMSAGGGGPLGDNNQGAD GVGNASGDWHCDSTWMGDRVVTKSTRTWVLPSYNNHQYREIK SGSVDGSNANAYFGYSTPWGYFDFNRFHSHWSPRDWQRLINN YWGFRPRSLRVKIFNIQVKEVTVQDSTTTIANNLTSTVQVFT DDDYQLPYVVGNGTEGCLPAFPPQVFTLPQYGYATLNRDNTE NPTERSSFFCLEYFPSKMLRTGNNFEFTYNFEEVPFHSSFAP SQNLFKLANPLVDQYLYRFVSTNNTGGVQFNKNLAGRYANTY KNWFPGPMGRTQGWNLGSGVNRASVSAFATTNRMELEGASYQ VPPQPNGMTNNLQGSNTYALENTMIFNSQPANPGTTATYLEG NMLITSESETQPVNRVAYNVGGQMATNNQSSTTAPTTGTYNL QEIVPGSVWMERDVYLQGPIWAKIPETGAHFHPSPAMGGFGL KHPPPMMLIKNTPVPGNITSFSDVPVSSFITQYSTGQVTVEM EWELKKENSKRWNPEIQYTNNYNDPQFVDFAPDSTGEYRTTR PIGTRYLTRPL | AAV2.5T VP1 |
| 6 | MSFVDHPPDWLEEVGEGLREFLGLEAGPPKPKPNQQHQDQAR GLVLPGYNYLGPGNGLDRGEPVNRADEVAREHDISYNEQLEA GDNPYLKYNHADAEFQEKLADDTSFGGNLGKAVFQAKKRVLE PFGLVEEGAKTAPTGKRIDDHFPKRKKARTEEDSKPSTSSDA EAGPSGSQQLQIPAQPASSLGADTMSAGGGGPLGDNNQGADG VGNASGDWHCDSTWMGDRVVTKSTRTWVLPSYNNHQYREIKS GSVDGSNANAYFGYSTPWGYFDFNRFHSHWSPRDWQRLINNY WGFRPRSLRVKIFNIQVKEVTVQDSTTTIANNLTSTVQVFTD DDYQLPYVVGNGTEGCLPAFPPQVFTLPQYGYATLNRDNTEN PTERSSFFCLEYFPSKMLRTGNNFEFTYNFEEVPFHSSFAPS QNLFKLANPLVDQYLYRFVSTNNTGGVQFNKNLAGRYANTYK NWFPGPMGRTQGWNLGSGVNRASVSAFATTNRMELEGASYQV PPQPNGMTNNLQGSNTYALENTMIFNSQPANPGTTATYLEGN MLITSESETQPVNRVAYNVGGQMLAHKFKSGDAPATGTYNLQ EIVPGSVWMERDVYLQGPIWAKIPETGAHFHPSPAMGGFGLK HPPPMMLIKNTPVPGNITSFSDVPVSSFITQYSTGQVTVEME WELKKENSKRWNPEIQYTNNYNDPQFVDFAPDSTGEYRTTRP IGTRYLTRPL | AAV5.LSV1 VP1 |
| 7 | MAADGYLPDWLEDTLSEGIRQWWKLKPGPPPPKPAERHKDDS RGLVLPGYKYLGPFNGLDKGEPVNEADAAALEHDKAYDRQLD SGDNPYLKYNHADAEFQERLKEDTSFGGNLGRAVFQAKKRVL EPFGLVEEGAKTAPTGKRIDDHFPKRKKARTEEDSKPSTSSD | AAV2.5T.LSV1 VP1 |

-continued

SEQUENCES

| # | SEQUENCE | ANNOTATION |
|---|----------|------------|
|  | AEAGPSGSQQLQIPAQPASSLGADTMSAGGGGPLGDNNQGAD GVGNASGDWHCDSTWMGDRVVTKSTRTWVLPSYNNHQYREIK SGSVDGSNANAYFGYSTPWGYFDFNRFHSHWSPRDWQRLINN YWGFRPRSLRVKIFNIQVKEVTVQDSTTTIANNLTSTVQVFT DDDYQLPYVVGNGTEGCLPAFPPQVFTLPQYGYATLNRDNTE NPTERSSFFCLEYFPSKMLRTGNNFEFTYNFEEVPFHSSFAP SQNLFKLANPLVDQYLRFVSTNNTGGVQFNKNLAGRYANTY KNWFPGPMGRTQGWNLGSGVNRASVSAFATTNRMELEGASYQ VPPQPNGMTNNLQGSNTYALENTMIFNSQPANPGTTATYLEG NMLITSESETQPVNRVAYNVGGQMLAHKFKSGDAPTTGTYNL QEIVPGSVWMERDVYLQGPIWAKIPETGAHFHPSPAMGGFGL KHPPPMMLIKNTPVPGNITSFSDVPVSSFITQYSTGQVTVEM EWELKKENSKRWNPEIQYTNNYNDPQFVDFAPDSTGEYRTTR PIGTRYLTRPL |  |
| 8 | EVQLVESGGGLVQPGGSLRLSCAASGYTFTNYGMNWVRQAPG KGLEWVGWINTYTGEPTYAADFKRRFTFSLDTSKSTAYLQMN SLRAEDTAVYYCAKYPHYYGSSHWYFDVWGQGTL | Bevacizumab heavy chain variable domain |
| 9 | DIQMTQSPSSLSASVGDRVTITCSASQDISNYLNWYQQKPGK APKVLIYFTSSLHSGVPSRFSGSGSGTDFTLTISSLQPEDFA TYYCQQYSTVPWTFGQGTKVEIKRTV | Bevacizumab light chain variable domain |
| 10 | EVQLVESGGGLVQPGGSLRLSCAASGYDFTHYGMNWVRQAPG KGLEWVGWINTYTGEPTYAADFKRRFTFSLDTSKSTAYLQMN SLRAEDTAVYYCAKYPYYYGTSHWYFDVWGQGTL | Ranibizumab heavy chain variable domain |
| 11 | DIQLTQSPSSLSASVGDRVTITCSASQDISNYLNWYQQKPGK APKVLIYFTSSLHSGVPSRFSGSGSGTDFTLTISSLQPEDFA TYYCQQYSTVPWTFGQGTKVEIKRTV | Ranibizumab light chain variable domain |
| 12 | MVSYWDTGVLLCALLSCLLLTGSSSGSDTGRPFVEMYSEIPE IIHMTEGRELVIPCRVTSPNITVTLKKFPLDTLIPDGKRIIW DSRKGFIISNATYKEIGLLTCEATVNGHLYKTNYLTHRQTNT IIDVVLSPSHGIELSVGEKLVLNCTARTELNVGIDFNWEYPS SKHQHKKLVNRDLKTQSGSEMKKFLSTLTIDGVTRSDQGLYT CAASSGLMTKKNSTFVRVHEKDKTHTCPPCPAPELLGGPSVF LFPPKPKDTLMISRTPEVTCVVVDVSHEDPEVKFNWYVDGVE VHNAKTKPREEQYNSTYRVVSVLTVLHQDWLNGKEYKCKVSN KALPAPIEKTISKAKGQPREPQVYTLPPSRDELTKNQVSLTC LVKGFYPSDIAVEWESNGQPENNYKTTPPVLDSDGSFFLYSK LTVDKSRWQQGNVFSCSVMHEALHNHYTQKSLSLSPGK | Aflibercept |
| 13 | MVSYWDTGVLLCALLSCLLLTGSSSGSKLKDPELSLKGTQHI AGQTLHLQCRGEAAMQHKWSLPEMVSKESERLSITKSACGRN GKQFCSTLTLNTAQANHTGFYSCKYLAVPTSKKKETESAIYI FISDTGRPFVEMYSEIPEIIHMTEGRELVIPCRVTSPNITVT LKKFPLDTLIPDGKRIIWDSRKGFIISNATYKEIGLLTCEAT VNGHLYKTNYLTHRQTNTBDVQISTPRPVKLLRGHTLVLNCT ATTPLNTRVQMTWSYPDEKNKRASVRRRIDQSNSHANIFYSV LTIDKMQNKDKGLYTCRVRSGPSFKSVNTSVHIYDKAFITVK HRKQQVLETVAGKRSYRLSMKVKAFPSPEVVWLKDGLPATEK SARYLTRGYSLIIKDVTEEDAGNYTILLSIKQSNVFKNLTAT LIVNVKPQIYEKAVSSFPDPALYPLGSRQ | sFlt-1 |
| 14 | IYIFISDTGRPFVEMYSEIPEIIHMTEGRELVIPCRVTSPNI TVTLKKFPLDTLIPDGKRIIWDSRKGFIISNATYKEIGLLTC EATVNGHLYKTNYLTHRQTNTI | sFlt-1 fragment |
| 15 | EIVMTQSPSTLSASVGDRVIITCQASEIIHSWLAWYQQKPGK APKLLIYLASTLASGVPSRFSGSGSGAEFTLTISSLQPDDFA TYYCQNVYLASTNGANFGQGTKLTVLGGGGSGGGGSGGGGS GGGGSEVQLVESGGGLVQPGGSLRLSCTASGFSLTDYYYMTW VRQAPGKGLEWVGFIDPDDDPYYATWAKGRFTISRDNSKNTL YLQMNSLRAEDTAVYYCAGGDHNSGWGLDIWGQGTLVTVSS | Brolucizumab |
| 16 | TAPTGKRIDDHFPKRKKARTEEDSKPSTSSDAEAGPSGSQQL QIPAQPASSLGADTMSAGGGGPLGDNNQGADGVGNASGDWHC DSTWMGDRVVTKSTRTWVLPSYNNHQYREIKSGSVDGSNANA YFGYSTPWGYFDFNRFHSHWSPRDWQRLINNYWGFRPRSLRV KIFNIQVKEVTVQDSTTTIANNLTSTVQVFTDDDYQLPYVVG NGTEGCLPAFPPQVFTLPQYGYATLNRDNTENPTERSSFFCL EYFPSKMLRTGNNFEFTYNFEEVPFHSSFAPSQNLFKLANPL VDQYLRFVSTNNTGGVQFNKNLAGRYANTYKNWFPGPMGRT QGWNLGSGVNRASVSAFATTNRMELEGASYQVPPQPNGMTNN | AAV5.LSV1 VP2 |

-continued

SEQUENCES

| # | SEQUENCE | ANNOTATION |
|---|----------|------------|
|   | LQGSNTYALENTMIFNSQPANPGTTATYLEGNMLITSESETQ<br>PVNRVAYNVGGQMLAHKFKSGDAPTTGTYNLQEIVPGSVWME<br>RDVYLQGPIWAKIPETGAHFHPSPAMGGFGLKHPPPMMLIKN<br>TPVPGNITSFSDVPVSSFITQYSTGQVTVEMEWELKKENSKR<br>WNPEIQYTNNYNDPQFVDFAPDSTGEYRTTRPIGTRYLTRPL |   |
| 17 | MSAGGGGPLGDNNQGADGVGNASGDWHCDSTWMGDRVVTKST<br>RTWVLPSYNNHQYREIKSGSVDGSNANAYFGYSTPWGYFDFN<br>RFHSHWSPRDWQRLINNYWGFRPRSLRVKIFNIQVKEVTVQD<br>STTTIANNLTSTVQVFTDDDYQLPYVVGNGTEGCLPAFPPQV<br>FTLPQYGYATLNRDNTENPTERSSFFCLEYFPSKMLRTGNNF<br>EFTYNFEEVPFHSSFAPSQNLFKLANPLVDQYLYRFVSTNNT<br>GGVQFNKNLAGRYANTYKNWFPGPMGRTQGWNLGSGVNRASV<br>SAFATTNRMELEGASYQVPPQPNGMTNNLQGSNTYALENTMI<br>FNSQPANPGTTATYLEGNMLITSESETQPVNRVAYNVGGQML<br>AHKFKSGDAPTTGTYNLQEIVPGSVWMERDVYLQGPIWAKIP<br>ETGAHFHPSPAMGGFGLKHPPPMMLIKNTPVPGNITSFSDVP<br>VSSFITQYSTGQVTVEMEWELKKENSKRWNPEIQYTNNYNDP<br>QFVDFAPDSTGEYRTTRPIGTRYLTRPL* | AAV5.LSV1 VP3 |

---

What is claimed is:

1. A recombinant adeno-associated virus (AAV) virion comprising:
   (a) a variant AAV capsid protein comprising a modified sequence comprising one or more amino acid substitutions within amino acid residues 570-579 relative to a parental AAV capsid protein, wherein the modified sequence comprises HKFKSGD (SEQ ID NO: 1), and wherein the amino acid residue numbering corresponds to an AAV5 VP1 capsid protein; and
   (b) a polynucleotide sequence encoding a therapeutic gene product.

2. The recombinant AAV virion of claim 1, wherein the parental AAV capsid protein is an AAV5 capsid protein or an AAV5 and AAV2 hybrid capsid protein.

3. The recombinant AAV virion of claim 1, wherein the parental AAV capsid protein is an AAV2.5T capsid protein.

4. The recombinant AAV virion of claim 1, wherein the parental AAV capsid protein is an AAV2.5T VP1 capsid protein.

5. The recombinant AAV virion of claim 1, wherein the modified sequence comprises LAHKFKSGDA (SEQ ID NO: 3).

6. The recombinant AAV virion of claim 1, wherein the variant AAV capsid protein comprises a capsid sequence having at least 85% homology to the amino acid sequence set forth in SEQ ID NO: 4 or SEQ ID NO:5 or a capsid sequence set forth in SEQ ID NO: 6 or SEQ ID NO: 7.

7. The recombinant AAV virion of claim 1, wherein the rAAV virion is a variant AAV5 or a variant AAV2 and AAV5 hybrid virion.

8. The recombinant AAV virion of claim 1, wherein the rAAV virion is a variant AAV2.5T virion.

9. The recombinant AAV virion of claim 1, wherein the recombinant AAV virion is capable of transducing cells of the retina when intravitreally injected into a mammal.

10. The recombinant AAV virion of claim 9, wherein the recombinant AAV virion is capable of transducing one or more of: a photoreceptor, a retinal ganglion cell, a Müller cell, a bipolar cell, an amacrine cell, a horizontal cell, and a retinal pigment epithelium cell when intravitreally injected into a mammal.

11. The recombinant AAV virion of claim 9, wherein the recombinant AAV virion is capable of transducing retinal pigment epithelium cells when intravitreally injected into a mammal.

12. The recombinant AAV virion of claim 1, wherein the therapeutic gene product is a siRNA, a miRNA, or a protein.

13. The recombinant AAV virion of claim 1, wherein the therapeutic gene product is an anti-vascular endothelial growth factor (anti-VEGF) gene product or an opsin.

14. The recombinant AAV virion of claim 1, wherein the polynucleotide encoding the therapeutic gene product is flanked by one or more AAV ITRs.

15. The recombinant AAV virion of claim 14, wherein the one or more AAV ITRs are AAV1, AAV2, AAV3, AAV4, AAV5, AAV6, AAV7, AAV8, AAV9, AAV10, avian AAV, bovine AAV, canine AAV, equine AAV, primate AAV, non-primate AAV, or ovine AAV ITRs or variants thereof.

16. The recombinant AAV virion of claim 14, wherein the one or more AAV ITRs are AAV2 ITRs or AAV5 ITRs.

17. The recombinant AAV virion of claim 1, wherein the recombinant AAV virion has an altered cellular tropism as compared to AAV2.5 T.

18. A pharmaceutical composition comprising the recombinant AAV virion of claim 1.

19. A method for producing a rAAV virion comprising:
(a) culturing a host cell under a condition that rAAV virions are produced, wherein the host cell comprises:
    (i) a polynucleotide encoding a variant AAV capsid protein comprising a modified sequence comprising one or more amino acid substitutions within amino acid residues 570-579 relative to a parental AAV capsid protein, wherein the modified sequence comprises HKFKSGD (SEQ ID NO: 1);
    (ii) a polynucleotide encoding a rep protein;
    (iii) a polynucleotide cassette comprising a sequence that encodes a therapeutic gene product flanked by at least one AAV ITR; and
    (iv) AAV helper functions; and
(b) recovering the rAAV virion produced by the host cell.

20. A method of providing a therapeutic gene product to a retina of a subject, comprising administering to the subject by intravitreal injection the recombinant AAV virion of claim 1.

21. A method of treating a disease or disorder of the retina of a subject in need thereof, comprising administering to the subject by intravitreal injection the recombinant AAV virion of claim 1.

22. The recombinant AAV virion of claim 1 for use in a method of treating a disease or disorder of the retina of a subject in need thereof, wherein the method comprises administering a pharmaceutical composition comprising the recombinant AAV virion to the subject by intravitreal injection.

23. The recombinant AAV virion of claim 1 for use in the preparation of a medicament for the treatment of a disease or disorder of the retina of a subject.

24. A variant AAV capsid protein comprising a modified sequence comprising one or more amino acid substitutions within amino acid residues 570-579 relative to a parental AAV capsid protein, wherein the modified sequence comprises HKFKSGD (SEQ ID NO: 1), and wherein the amino acid residue numbering corresponds to an AAV5 VP1 capsid protein.

25. The variant AAV capsid protein of claim 24, wherein the parental AAV capsid protein is an AAV5 capsid protein or an AAV5 and AAV2 hybrid capsid protein.

26. The variant AAV capsid protein of claim 24, wherein the parental AAV capsid protein is an AAV2.5T capsid protein.

27. The variant AAV capsid protein of claim 24, wherein the parental AAV capsid protein is an AAV2.5T VP1 capsid protein.

28. The variant AAV capsid protein of claim 24, wherein the modified AAV capsid protein comprises LAHKFKSGDA (SEQ ID NO: 3) at amino acid residues 570-579 relative to the parental AAV capsid protein.

29. The variant AAV capsid protein of claim 24, comprising a capsid sequence having at least 85% homology to the amino acid sequence set forth in SEQ ID NO: 4 or SEQ ID NO:5, or a capsid sequence set forth in SEQ ID NO: 6 or SEQ ID NO: 7.

30. A nucleic acid comprising a nucleic acid sequence encoding the variant AAV capsid protein of claim 24.

31. An expression vector comprising the nucleic acid of claim 30, wherein the nucleic acid sequence encoding the variant AAV capsid protein is operably linked to a promoter sequence.

32. A cell comprising the expression vector of claim 31.

* * * * *

SEQUENCE LISTING

<160> NUMBER OF SEQ ID NOS: 17

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

His Lys Phe Lys Ser Gly Asp
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 10
<223> OTHER INFORMATION: Xaa = Any Amino Acid

<400> SEQUENCE: 2

Xaa Xaa His Lys Phe Lys Ser Gly Asp Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Leu Ala His Lys Phe Lys Ser Gly Asp Ala
1               5                   10

<210> SEQ ID NO 4
<211> LENGTH: 724
<212> TYPE: PRT
<213> ORGANISM: Artificial Sequence
<220> FEATURE:
<223> OTHER INFORMATION: Synthetic Construct

<400> SEQUENCE: 4

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400
```

```
Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 5
<211> LENGTH: 725
<212> TYPE: PRT
<213> ORGANISM: Artificial Sequence
<220> FEATURE:
<223> OTHER INFORMATION: Synthetic Construct

<400> SEQUENCE: 5

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30
```

```
Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65              70                  75                  80

Arg Gln Leu Asp Ser Gly Asp Asn Pro Tyr Leu Lys Tyr Asn His Ala
             85                  90                  95

Asp Ala Glu Phe Gln Glu Arg Leu Lys Glu Asp Thr Ser Phe Gly Gly
             100                 105                 110

Asn Leu Gly Arg Ala Val Phe Gln Ala Lys Lys Arg Val Leu Glu Pro
             115                 120                 125

Phe Gly Leu Val Glu Glu Gly Ala Lys Thr Ala Pro Thr Gly Lys Arg
 130                 135                 140

Ile Asp Asp His Phe Pro Lys Arg Lys Lys Ala Arg Thr Glu Glu Asp
 145                 150                 155                 160

Ser Lys Pro Ser Thr Ser Ser Asp Ala Glu Ala Gly Pro Ser Gly Ser
             165                 170                 175

Gln Gln Leu Gln Ile Pro Ala Gln Pro Ala Ser Ser Leu Gly Ala Asp
             180                 185                 190

Thr Met Ser Ala Gly Gly Gly Pro Leu Gly Asp Asn Asn Gln Gly
             195                 200                 205

Ala Asp Gly Val Gly Asn Ala Ser Gly Asp Trp His Cys Asp Ser Thr
 210                 215                 220

Trp Met Gly Asp Arg Val Val Thr Lys Ser Thr Arg Thr Trp Val Leu
 225                 230                 235                 240

Pro Ser Tyr Asn Asn His Gln Tyr Arg Glu Ile Lys Ser Gly Ser Val
             245                 250                 255

Asp Gly Ser Asn Ala Asn Ala Tyr Phe Gly Tyr Ser Thr Pro Trp Gly
             260                 265                 270

Tyr Phe Asp Phe Asn Arg Phe His Ser His Trp Ser Pro Arg Asp Trp
 275                 280                 285

Gln Arg Leu Ile Asn Asn Tyr Trp Gly Phe Arg Pro Arg Ser Leu Arg
 290                 295                 300

Val Lys Ile Phe Asn Ile Gln Val Lys Glu Val Thr Val Gln Asp Ser
 305                 310                 315                 320

Thr Thr Thr Ile Ala Asn Asn Leu Thr Ser Thr Val Gln Val Phe Thr
             325                 330                 335

Asp Asp Asp Tyr Gln Leu Pro Tyr Val Val Gly Asn Gly Thr Glu Gly
             340                 345                 350

Cys Leu Pro Ala Phe Pro Pro Gln Val Phe Thr Leu Pro Gln Tyr Gly
             355                 360                 365

Tyr Ala Thr Leu Asn Arg Asp Asn Thr Glu Asn Pro Thr Glu Arg Ser
             370                 375                 380

Ser Phe Phe Cys Leu Glu Tyr Phe Pro Ser Lys Met Leu Arg Thr Gly
 385                 390                 395                 400

Asn Asn Phe Glu Phe Thr Tyr Asn Phe Glu Glu Val Pro Phe His Ser
             405                 410                 415

Ser Phe Ala Pro Ser Gln Asn Leu Phe Lys Leu Ala Asn Pro Leu Val
             420                 425                 430

Asp Gln Tyr Leu Tyr Arg Phe Val Ser Thr Asn Asn Thr Gly Gly Val
             435                 440                 445

Gln Phe Asn Lys Asn Leu Ala Gly Arg Tyr Ala Asn Thr Tyr Lys Asn
```

```
                450             455             460
Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Gln Pro Asn Gly Met
            500                 505                 510

Thr Asn Asn Leu Gln Gly Ser Asn Thr Tyr Ala Leu Glu Asn Thr Met
                515                 520                 525

Ile Phe Asn Ser Gln Pro Ala Asn Pro Gly Thr Thr Ala Thr Tyr Leu
530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Ser
                565                 570                 575

Ser Thr Thr Ala Pro Thr Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
                660                 665                 670

Glu Trp Glu Leu Lys Lys Glu Asn Ser Lys Arg Trp Asn Pro Glu Ile
            675                 680                 685

Gln Tyr Thr Asn Asn Tyr Asn Asp Pro Gln Phe Val Asp Phe Ala Pro
        690                 695                 700

Asp Ser Thr Gly Glu Tyr Arg Thr Thr Arg Pro Ile Gly Thr Arg Tyr
705                 710                 715                 720

Leu Thr Arg Pro Leu
                725

<210> SEQ ID NO 6
<211> LENGTH: 724
<212> TYPE: PRT
<213> ORGANISM: Artificial Sequence
<220> FEATURE:
<223> OTHER INFORMATION: Synthetic Construct

<400> SEQUENCE: 6

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
```

```
                       85                  90                  95
Ala Glu Phe Gln Glu Lys Leu Ala Asp Asp Thr Ser Phe Gly Gly Asn
                100                 105                 110

Leu Gly Lys Ala Val Phe Gln Ala Lys Lys Arg Val Leu Glu Pro Phe
            115                 120                 125

Gly Leu Val Glu Glu Gly Ala Lys Thr Ala Pro Thr Gly Lys Arg Ile
        130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
        210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
        290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
        370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
        450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510
```

```
Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Leu Ala His Lys Phe Lys Ser
                565                 570                 575

Gly Asp Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
        610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
        690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 7
<211> LENGTH: 725
<212> TYPE: PRT
<213> ORGANISM: Artificial Sequence
<220> FEATURE:
<223> OTHER INFORMATION: Synthetic Construct

<400> SEQUENCE: 7

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
    130                 135                 140
```

-continued

```
Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
            165                 170                 175

Gln Gln Leu Gln Ile Pro Ala Gln Pro Ala Ser Ser Leu Gly Ala Asp
        180                 185                 190

Thr Met Ser Ala Gly Gly Gly Pro Leu Gly Asp Asn Asn Gln Gly
    195                 200                 205

Ala Asp Gly Val Gly Asn Ala Ser Gly Asp Trp His Cys Asp Ser Thr
210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
        355                 360                 365

Tyr Ala Thr Leu Asn Arg Asp Asn Thr Glu Asn Pro Thr Glu Arg Ser
    370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
    530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Leu Ala His Lys Phe Lys
```

```
                          565                 570                 575

Ser Gly Asp Ala Pro Thr Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
    610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
            660                 665                 670

Glu Trp Glu Leu Lys Lys Glu Asn Ser Lys Arg Trp Asn Pro Glu Ile
        675                 680                 685

Gln Tyr Thr Asn Asn Tyr Asn Asp Pro Gln Phe Val Asp Phe Ala Pro
    690                 695                 700

Asp Ser Thr Gly Glu Tyr Arg Thr Thr Arg Pro Ile Gly Thr Arg Tyr
705                 710                 715                 720

Leu Thr Arg Pro Leu
                725

<210> SEQ ID NO 8
<211> LENGTH: 118
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                  10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu
        115

<210> SEQ ID NO 9
<211> LENGTH: 110
<212> TYPE: PRT
<213> ORGANISM: Artificial Sequence
<220> FEATURE:
<223> OTHER INFORMATION: Synthetic Construct

<400> SEQUENCE: 9

Asp Ile Gln Met Thr Gln Ser Pro Ser Ser Leu Ser Ala Ser Val Gly
1               5                  10                  15
```

-continued

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val
            100                 105                 110

<210> SEQ ID NO 10
<211> LENGTH: 118
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu
        115

<210> SEQ ID NO 11
<211> LENGTH: 110
<212> TYPE: PRT
<213> ORGANISM: Artificial Sequence
<220> FEATURE:
<223> OTHER INFORMATION: Synthetic Construct

<400> SEQUENCE: 11

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

```
Thr Phe Gly Gln Gly Thr Lys Val Glu Ile Lys Arg Thr Val
                100                 105                 110
```

<210> SEQ ID NO 12
<211> LENGTH: 458
<212> TYPE: PRT
<213> ORGANISM: Artificial Sequence
<220> FEATURE:
<223> OTHER INFORMATION: Synthetic Construct

<400> SEQUENCE: 12

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350
```

```
Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro Gly Lys
            450                 455

<210> SEQ ID NO 13
<211> LENGTH: 450
<212> TYPE: PRT
<213> ORGANISM: Artificial Sequence
<220> FEATURE:
<223> OTHER INFORMATION: Synthetic Construct

<400> SEQUENCE: 13

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Ala Gly Gln Thr Leu His
            35                  40                  45

Leu Gln Cys Arg Gly Glu Ala Ala Met Gln His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255
```

```
Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
                355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln
    450

<210> SEQ ID NO 14
<211> LENGTH: 106
<212> TYPE: PRT
<213> ORGANISM: Artificial Sequence
<220> FEATURE:
<223> OTHER INFORMATION: Synthetic Construct

<400> SEQUENCE: 14

Ile Tyr Ile Phe Ile Ser Asp Thr Gly Arg Pro Phe Val Glu Met Tyr
1               5                   10                  15

Ser Glu Ile Pro Glu Ile Ile His Met Thr Glu Gly Arg Glu Leu Val
            20                  25                  30

Ile Pro Cys Arg Val Thr Ser Pro Asn Ile Thr Val Thr Leu Lys Lys
        35                  40                  45

Phe Pro Leu Asp Thr Leu Ile Pro Asp Gly Lys Arg Ile Ile Trp Asp
    50                  55                  60

Ser Arg Lys Gly Phe Ile Ile Ser Asn Ala Thr Tyr Lys Glu Ile Gly
65                  70                  75                  80

Leu Leu Thr Cys Glu Ala Thr Val Asn Gly His Leu Tyr Lys Thr Asn
                85                  90                  95

Tyr Leu Thr His Arg Gln Thr Asn Thr Ile
            100                 105

<210> SEQ ID NO 15
<211> LENGTH: 251
<212> TYPE: PRT
<213> ORGANISM: Artificial Sequence
<220> FEATURE:
<223> OTHER INFORMATION: Synthetic Construct
```

<400> SEQUENCE: 15

| Glu | Ile | Val | Met | Thr | Gln | Ser | Pro | Ser | Thr | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Ile | Ile | Thr | Cys | Gln | Ala | Ser | Glu | Ile | Ile | His | Ser | Trp |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | 35 | | | | | 40 | | | | | 45 | | | |

| Tyr | Leu | Ala | Ser | Thr | Leu | Ala | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Ala | Glu | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Asp | Asp | Phe | Ala | Thr | Tyr | Tyr | Cys | Gln | Asn | Val | Tyr | Leu | Ala | Ser | Thr |
|---|---|---|---|---|---|---|---|---|---|---|---|---|---|---|---|
| | | | | 85 | | | | | 90 | | | | | 95 | |

| Asn | Gly | Ala | Asn | Phe | Gly | Gln | Gly | Thr | Lys | Leu | Thr | Val | Leu | Gly | Gly |
|---|---|---|---|---|---|---|---|---|---|---|---|---|---|---|---|
| | | | 100 | | | | | 105 | | | | | 110 | | |

| Gly | Gly | Gly | Ser | Gly | Gly | Gly | Gly | Ser | Gly | Gly | Gly | Ser | Gly | Gly |
|---|---|---|---|---|---|---|---|---|---|---|---|---|---|---|
| | | 115 | | | | | 120 | | | | | 125 | | |

| Gly | Gly | Ser | Glu | Val | Gln | Leu | Val | Glu | Ser | Gly | Gly | Leu | Val | Gln |
|---|---|---|---|---|---|---|---|---|---|---|---|---|---|---|
| | 130 | | | | | 135 | | | | | 140 | | | |

| Pro | Gly | Gly | Ser | Leu | Arg | Leu | Ser | Cys | Thr | Ala | Ser | Gly | Phe | Ser | Leu |
|---|---|---|---|---|---|---|---|---|---|---|---|---|---|---|---|
| 145 | | | | | 150 | | | | | 155 | | | | | 160 |

| Thr | Asp | Tyr | Tyr | Met | Thr | Trp | Val | Arg | Gln | Ala | Pro | Gly | Lys | Gly |
|---|---|---|---|---|---|---|---|---|---|---|---|---|---|---|
| | | | 165 | | | | | 170 | | | | | 175 | |

| Leu | Glu | Trp | Val | Gly | Phe | Ile | Asp | Pro | Asp | Asp | Pro | Tyr | Tyr | Ala |
|---|---|---|---|---|---|---|---|---|---|---|---|---|---|---|
| | | | 180 | | | | | 185 | | | | | 190 | |

| Thr | Trp | Ala | Lys | Gly | Arg | Phe | Thr | Ile | Ser | Arg | Asp | Asn | Ser | Lys | Asn |
|---|---|---|---|---|---|---|---|---|---|---|---|---|---|---|---|
| | | | 195 | | | | | 200 | | | | | 205 | | |

| Thr | Leu | Tyr | Leu | Gln | Met | Asn | Ser | Leu | Arg | Ala | Glu | Asp | Thr | Ala | Val |
|---|---|---|---|---|---|---|---|---|---|---|---|---|---|---|---|
| | | 210 | | | | | 215 | | | | | 220 | | | |

| Tyr | Tyr | Cys | Ala | Gly | Gly | Asp | His | Asn | Ser | Gly | Trp | Gly | Leu | Asp | Ile |
|---|---|---|---|---|---|---|---|---|---|---|---|---|---|---|---|
| 225 | | | | | 230 | | | | | 235 | | | | | 240 |

| Trp | Gly | Gln | Gly | Thr | Leu | Val | Thr | Val | Ser | Ser |
|---|---|---|---|---|---|---|---|---|---|---|
| | | | | 245 | | | | | 250 | |

<210> SEQ ID NO 16
<211> LENGTH: 588
<212> TYPE: PRT
<213> ORGANISM: Artificial Sequence
<220> FEATURE:
<223> OTHER INFORMATION: Synthetic Construct

<400> SEQUENCE: 16

| Thr | Ala | Pro | Thr | Gly | Lys | Arg | Ile | Asp | Asp | His | Phe | Pro | Lys | Arg | Lys |
|---|---|---|---|---|---|---|---|---|---|---|---|---|---|---|---|
| 1 | | | | 5 | | | | | 10 | | | | | 15 | |

| Lys | Ala | Arg | Thr | Glu | Glu | Asp | Ser | Lys | Pro | Ser | Thr | Ser | Ser | Asp | Ala |
|---|---|---|---|---|---|---|---|---|---|---|---|---|---|---|---|
| | | | 20 | | | | | 25 | | | | | 30 | | |

| Glu | Ala | Gly | Pro | Ser | Gly | Ser | Gln | Gln | Leu | Gln | Ile | Pro | Ala | Gln | Pro |
|---|---|---|---|---|---|---|---|---|---|---|---|---|---|---|---|
| | | 35 | | | | | 40 | | | | | 45 | | | |

| Ala | Ser | Ser | Leu | Gly | Ala | Asp | Thr | Met | Ser | Ala | Gly | Gly | Gly | Pro |
|---|---|---|---|---|---|---|---|---|---|---|---|---|---|---|
| | 50 | | | | | 55 | | | | | 60 | | | |

| Leu | Gly | Asp | Asn | Asn | Gln | Gly | Ala | Asp | Gly | Gly | Asn | Ala | Ser | Gly |
|---|---|---|---|---|---|---|---|---|---|---|---|---|---|---|
| 65 | | | | | 70 | | | | | 75 | | | | | 80 |

| Asp | Trp | His | Cys | Asp | Ser | Thr | Trp | Met | Gly | Asp | Arg | Val | Val | Thr | Lys |
|---|---|---|---|---|---|---|---|---|---|---|---|---|---|---|---|
| | | | | 85 | | | | | 90 | | | | | 95 | |

| Ser | Thr | Arg | Thr | Trp | Val | Leu | Pro | Ser | Tyr | Asn | Asn | His | Gln | Tyr | Arg |

```
                100             105             110
Glu Ile Lys Ser Gly Ser Val Asp Gly Ser Asn Ala Asn Ala Tyr Phe
            115                 120             125

Gly Tyr Ser Thr Pro Trp Gly Tyr Phe Asp Phe Asn Arg Phe His Ser
        130             135             140

His Trp Ser Pro Arg Asp Trp Gln Arg Leu Ile Asn Asn Tyr Trp Gly
145             150              155                 160

Phe Arg Pro Arg Ser Leu Arg Val Lys Ile Phe Asn Ile Gln Val Lys
                165             170             175

Glu Val Thr Val Gln Asp Ser Thr Thr Ile Ala Asn Asn Leu Thr
            180             185             190

Ser Thr Val Gln Val Phe Thr Asp Asp Tyr Gln Leu Pro Tyr Val
        195             200             205

Val Gly Asn Gly Thr Glu Gly Cys Leu Pro Ala Phe Pro Pro Gln Val
        210             215             220

Phe Thr Leu Pro Gln Tyr Gly Tyr Ala Thr Leu Asn Arg Asp Asn Thr
225             230             235             240

Glu Asn Pro Thr Glu Arg Ser Ser Phe Phe Cys Leu Glu Tyr Phe Pro
            245             250             255

Ser Lys Met Leu Arg Thr Gly Asn Asn Phe Glu Phe Thr Tyr Asn Phe
            260             265             270

Glu Glu Val Pro Phe His Ser Ser Phe Ala Pro Ser Gln Asn Leu Phe
            275             280             285

Lys Leu Ala Asn Pro Leu Val Asp Gln Tyr Leu Tyr Arg Phe Val Ser
        290             295             300

Thr Asn Asn Thr Gly Gly Val Gln Phe Asn Lys Asn Leu Ala Gly Arg
305             310             315             320

Tyr Ala Asn Thr Tyr Lys Asn Trp Phe Pro Gly Pro Met Gly Arg Thr
                325             330             335

Gln Gly Trp Asn Leu Gly Ser Gly Val Asn Arg Ala Ser Val Ser Ala
            340             345             350

Phe Ala Thr Thr Asn Arg Met Glu Leu Glu Gly Ala Ser Tyr Gln Val
            355             360             365

Pro Pro Gln Pro Asn Gly Met Thr Asn Asn Leu Gln Gly Ser Asn Thr
370             375             380

Tyr Ala Leu Glu Asn Thr Met Ile Phe Asn Ser Gln Pro Ala Asn Pro
385             390             395             400

Gly Thr Thr Ala Thr Tyr Leu Glu Gly Asn Met Leu Ile Thr Ser Glu
                405             410             415

Ser Glu Thr Gln Pro Val Asn Arg Val Ala Tyr Asn Val Gly Gly Gln
            420             425             430

Met Leu Ala His Lys Phe Lys Ser Gly Asp Ala Pro Thr Thr Gly Thr
            435             440             445

Tyr Asn Leu Gln Glu Ile Val Pro Gly Ser Val Trp Met Glu Arg Asp
        450             455             460

Val Tyr Leu Gln Gly Pro Ile Trp Ala Lys Ile Pro Glu Thr Gly Ala
465             470             475             480

His Phe His Pro Ser Pro Ala Met Gly Gly Phe Gly Leu Lys His Pro
                485             490             495

Pro Pro Met Met Leu Ile Lys Asn Thr Pro Val Pro Gly Asn Ile Thr
            500             505             510

Ser Phe Ser Asp Val Pro Val Ser Ser Phe Ile Thr Gln Tyr Ser Thr
            515             520             525
```

-continued

```
Gly Gln Val Thr Val Glu Met Glu Trp Glu Leu Lys Lys Glu Asn Ser
            530                 535                 540

Lys Arg Trp Asn Pro Glu Ile Gln Tyr Thr Asn Asn Tyr Asn Asp Pro
545                 550                 555                 560

Gln Phe Val Asp Phe Ala Pro Asp Ser Thr Gly Glu Tyr Arg Thr Thr
                565                 570                 575

Arg Pro Ile Gly Thr Arg Tyr Leu Thr Arg Pro Leu
            580                 585

<210> SEQ ID NO 17
<211> LENGTH: 532
<212> TYPE: PRT
<213> ORGANISM: Artificial Sequence
<220> FEATURE:
<223> OTHER INFORMATION: Synthetic Construct

<400> SEQUENCE: 17

Met Ser Ala Gly Gly Gly Pro Leu Gly Asp Asn Asn Gln Gly Ala
1               5                   10                  15

Asp Gly Val Gly Asn Ala Ser Gly Asp Trp His Cys Asp Ser Thr Trp
            20                  25                  30

Met Gly Asp Arg Val Val Thr Lys Ser Thr Arg Thr Trp Val Leu Pro
        35                  40                  45

Ser Tyr Asn Asn His Gln Tyr Arg Glu Ile Lys Ser Gly Ser Val Asp
50                  55                  60

Gly Ser Asn Ala Asn Ala Tyr Phe Gly Tyr Ser Thr Pro Trp Gly Tyr
65                  70                  75                  80

Phe Asp Phe Asn Arg Phe His Ser His Trp Ser Pro Arg Asp Trp Gln
                85                  90                  95

Arg Leu Ile Asn Asn Tyr Trp Gly Phe Arg Pro Arg Ser Leu Arg Val
            100                 105                 110

Lys Ile Phe Asn Ile Gln Val Lys Glu Val Thr Val Gln Asp Ser Thr
        115                 120                 125

Thr Thr Ile Ala Asn Asn Leu Thr Ser Thr Val Gln Val Phe Thr Asp
130                 135                 140

Asp Asp Tyr Gln Leu Pro Tyr Val Val Gly Asn Gly Thr Glu Gly Cys
145                 150                 155                 160

Leu Pro Ala Phe Pro Pro Gln Val Phe Thr Leu Pro Gln Tyr Gly Tyr
                165                 170                 175

Ala Thr Leu Asn Arg Asp Asn Thr Glu Asn Pro Thr Glu Arg Ser Ser
            180                 185                 190

Phe Phe Cys Leu Glu Tyr Phe Pro Ser Lys Met Leu Arg Thr Gly Asn
        195                 200                 205

Asn Phe Glu Phe Thr Tyr Asn Phe Glu Glu Val Pro Phe His Ser Ser
210                 215                 220

Phe Ala Pro Ser Gln Asn Leu Phe Lys Leu Ala Asn Pro Leu Val Asp
225                 230                 235                 240

Gln Tyr Leu Tyr Arg Phe Val Ser Thr Asn Asn Thr Gly Gly Val Gln
                245                 250                 255

Phe Asn Lys Asn Leu Ala Gly Arg Tyr Ala Asn Thr Tyr Lys Asn Trp
            260                 265                 270

Phe Pro Gly Pro Met Gly Arg Thr Gln Gly Trp Asn Leu Gly Ser Gly
        275                 280                 285

Val Asn Arg Ala Ser Val Ser Ala Phe Ala Thr Thr Asn Arg Met Glu
290                 295                 300
```

```
Leu Glu Gly Ala Ser Tyr Gln Val Pro Pro Gln Pro Asn Gly Met Thr
305                 310                 315                 320

Asn Asn Leu Gln Gly Ser Asn Thr Tyr Ala Leu Glu Asn Thr Met Ile
            325                 330                 335

Phe Asn Ser Gln Pro Ala Asn Pro Gly Thr Thr Ala Thr Tyr Leu Glu
            340                 345                 350

Gly Asn Met Leu Ile Thr Ser Glu Ser Glu Thr Gln Pro Val Asn Arg
            355                 360                 365

Val Ala Tyr Asn Val Gly Gly Gln Met Leu Ala His Lys Phe Lys Ser
        370                 375                 380

Gly Asp Ala Pro Thr Thr Gly Thr Tyr Asn Leu Gln Glu Ile Val Pro
385                 390                 395                 400

Gly Ser Val Trp Met Glu Arg Asp Val Tyr Leu Gln Gly Pro Ile Trp
                405                 410                 415

Ala Lys Ile Pro Glu Thr Gly Ala His Phe His Pro Ser Pro Ala Met
            420                 425                 430

Gly Gly Phe Gly Leu Lys His Pro Pro Pro Met Met Leu Ile Lys Asn
        435                 440                 445

Thr Pro Val Pro Gly Asn Ile Thr Ser Phe Ser Asp Val Pro Val Ser
    450                 455                 460

Ser Phe Ile Thr Gln Tyr Ser Thr Gly Gln Val Thr Val Glu Met Glu
465                 470                 475                 480

Trp Glu Leu Lys Lys Glu Asn Ser Lys Arg Trp Asn Pro Glu Ile Gln
                485                 490                 495

Tyr Thr Asn Asn Tyr Asn Asp Pro Gln Phe Val Asp Phe Ala Pro Asp
            500                 505                 510

Ser Thr Gly Glu Tyr Arg Thr Thr Arg Pro Ile Gly Thr Arg Tyr Leu
            515                 520                 525

Thr Arg Pro Leu
    530
```

UNITED STATES PATENT AND TRADEMARK OFFICE
CERTIFICATE OF CORRECTION

| | | |
|---|---|---|
| PATENT NO. | : 11,510,950 B2 | Page 1 of 1 |
| APPLICATION NO. | : 16/858042 | |
| DATED | : November 29, 2022 | |
| INVENTOR(S) | : Keravala et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 325 days.

Signed and Sealed this
Fourteenth Day of January, 2025

Derrick Brent
*Acting Director of the United States Patent and Trademark Office*